(12) United States Patent
Chan-Hui et al.

(10) Patent No.: US 7,105,308 B2
(45) Date of Patent: Sep. 12, 2006

(54) DETECTING RECEPTOR OLIGOMERIZATION

(75) Inventors: Po-Ying Chan-Hui, Oakland, CA (US); Yining Shi, San Jose, CA (US); Sailaja Pidaparthi, Cupertino, CA (US); Rajiv Dua, Manteca, CA (US); Sharat Singh, San Jose, CA (US)

(73) Assignee: Monogram Biosciences, Inc., South San Francisco, CA (US)

( * ) Notice: Subject to any disclaimer, the term of this patent is extended or adjusted under 35 U.S.C. 154(b) by 111 days.

(21) Appl. No.: 10/623,057

(22) Filed: Jul. 17, 2003

(65) Prior Publication Data

US 2004/0126818 A1 Jul. 1, 2004

Related U.S. Application Data

(60) Provisional application No. 60/398,724, filed on Jul. 25, 2002.

(51) Int. Cl.
*G01N 33/53* (2006.01)

(52) U.S. Cl. .................. 435/7.2; 435/7.1; 436/514; 436/516; 436/535

(58) Field of Classification Search ............. 436/518, 436/514, 516, 535; 435/7.1, 535
See application file for complete search history.

(56) References Cited

U.S. PATENT DOCUMENTS

| | | | |
|---|---|---|---|
| 4,331,590 A | 5/1982 | Bocuslaski | 260/112 B |
| 4,650,750 A | 3/1987 | Giese | 435/7 |
| 4,709,016 A | 11/1987 | Giese | 530/389 |
| 4,780,421 A | 10/1988 | Kameda | 436/518 |
| 5,340,716 A | 8/1994 | Ullman et al. | 435/6 |
| 5,360,819 A | 11/1994 | Giese | 514/538 |
| 5,516,636 A | 5/1996 | McCapra | 435/6 |
| 5,516,931 A | 5/1996 | Giese | 560/59 |
| 5,536,834 A | 7/1996 | Singh | 544/98 |
| 5,578,498 A | 11/1996 | Singh | 436/518 |
| 5,602,273 A | 2/1997 | Giese | 560/60 |
| 5,604,104 A | 2/1997 | Giese | 435/7.1 |
| 5,610,020 A | 3/1997 | Giese | 435/7.1 |
| 5,616,719 A | 4/1997 | Davalian | 546/334 |
| 5,622,929 A | 4/1997 | Willner | 514/8 |
| 5,635,602 A | 6/1997 | Cantor | 530/391 |

(Continued)

FOREIGN PATENT DOCUMENTS

WO    WO 00/66607    11/2000

(Continued)

OTHER PUBLICATIONS

Giese, "Electrophoric Release Tags: Ultrasensitive Molecular Labels Providing Multiplicity", Trends in Analytical Chemistry, vol. 2, No. 7, 1983, pp. 166-168.

(Continued)

*Primary Examiner*—Long V. Le
*Assistant Examiner*—Deborah A. Davis
(74) *Attorney, Agent, or Firm*—Jones Day

(57) ABSTRACT

Methods are provided for detecting formation of oligomeric complexes of molecules on the surface of cell membranes. These methods employ pairs of tagged probes and cleaving probes, each of which binds specifically to a cell surface molecule. The tagged probe includes a molecular tag that is linked to a first binding compound through a cleavable linkage, and the cleaving probe includes a second binding agent and a cleavage-inducing moiety that can cleave the linkage when within a defined proximity thereto. Binding of the two probes to cell surface molecules that have formed an oligomeric complex results in release of the molecular tag from the binding compound, providing a measure of formation of the complex.

31 Claims, 35 Drawing Sheets

U.S. PATENT DOCUMENTS

| | | | | |
|---|---|---|---|---|
| 5,650,270 | A | 7/1997 | Giese | 435/6 |
| 5,677,171 | A | 10/1997 | Hudziak et al. | 435/240 |
| 5,705,622 | A | 1/1998 | McCapra | 536/23.1 |
| 5,709,994 | A | 1/1998 | Pease | 435/4 |
| 5,766,481 | A | 6/1998 | Zambias | 210/656 |
| 5,777,096 | A | 7/1998 | Grossman | 536/24.3 |
| 5,789,172 | A | 8/1998 | Still | 435/6 |
| 5,807,675 | A | 9/1998 | Davalian | 435/6 |
| 5,843,655 | A | 12/1998 | McGall | 435/6 |
| 5,843,666 | A | 12/1998 | Akhavan-Tafti | 435/6 |
| 5,846,839 | A | 12/1998 | Gallop | 436/518 |
| 5,849,878 | A | 12/1998 | Cantor | 530/391.9 |
| 5,898,005 | A | 4/1999 | Singh | 436/527 |
| 5,952,654 | A | 9/1999 | Giese | 250/288 |
| 5,958,202 | A | 9/1999 | Regnier | 204/451 |
| 6,027,890 | A | 2/2000 | Ness | 435/6 |
| 6,251,581 | B1 | 6/2001 | Ullman | 435/4 |
| 6,322,980 | B1 | 11/2001 | Singh | 435/6 |
| 6,331,530 | B1 | 12/2001 | Breslow | 514/58 |
| 6,346,384 | B1 | 2/2002 | Pollner | 435/6 |
| 6,545,102 | B1 * | 4/2003 | Akhavan-Tafti et al. | 525/340 |
| 6,558,928 | B1 | 5/2003 | Landegren | |
| 6,627,400 | B1 * | 9/2003 | Singh et al. | 435/6 |
| 2002/0064779 | A1 | 5/2002 | Landegren et al. | |

FOREIGN PATENT DOCUMENTS

WO     WO 01/90399     11/2001

OTHER PUBLICATIONS

Kochevar et al., "Photosensitized Production of Singlet Oxygen", Methods in Enzymology, vol. 319, 2000, pp. 20-29.

Ni et al., "Versatile Approach to Encoding Combinatorial Organic Synthesis Using Chemically Robust Secondary Amine Tags", J. Med. Chem., vol. 39, 1996, pp. 1601-1608.

Olejnik et al., "Photocleavable Affinity Tags for Isolation and Detection of Biomolecules", Methods in Enzymology, vol. 291, 1998, pp. 135-154.

Oseroff et al., "Antibody-Targeted Photolysis: Selective photodestruction of Human T-Cell Leukemia Cells Using Monoclonal Antibody-Chlorin $e_6$ Cojugates", Proc. Natl. Acad. Sci. USA, vol. 83, 1986, pp. 8744-8748.

Rakestraw et al., "Antibody-Targeted photolysis: In vitro Studies with Sn(IV) Chlorin e6 Covalently Bound to Monoclonal Antibodies Using a Modified Dextran Carrier", Proc. Natl. Acad. Sci USA, vol. 87, 1990, pp. 4217-4221.

Ullman et al., "Luminescent Oxygen Channeling Immunoassay: Measurement of Particle Binding Kinetics by Chemiluminescence", Proc. Natl. Acad. Sci. USA, vol. 91, 1994, pp. 5426-5430.

Beaudet et al, "Homogeneous Assays for Single-Nucleotide Polymorphism Typing Using AplhaScreen", Genome Research, 11-600-608.

Angers et al, "Dimerization: An Emerging Concept for G Protein-Coupled Receptor Ontogeny and Function", Annu. Rev. Parmacol. Toxicol, (2002) 42-409-435.

Overton et al, "G-protein-coupled Receptors Functions as Oligomers In Vivo", Current Biology, (2000) vol. 10, No. 6, 341-344.

Mellado et al, "Chemokine Signaling and Functional Responses: The Role of Receptor Dimerization and TK Pathway Activation" Annu. Rev. Immunol., 2001, 19,397-421.

Gomes et al, "G Protein Coupled Receptor Dimeraztion: Implications in Modulating Receptor Function", J. Mol. Med., 2001, 79,, 226-242.

Salim et al, "Oligomerization of G-protein-coupled Receptors Shown by Selective Co-immunoprecipitation", Journal of Bioligical Chemistry, 2002, vol. 277, No. 18, Issue of May 3, 2002, 15482-15485.

Angers et al, "Detection of β2-Adrenergic Receptor Dimerization in Living Cells Using Bioluminescence Resonance Energy Transfer (BRET)", PNAS, Mar. 28, 2000, vol. 97, No. 7, 3684-3689.

Jones et al., "Signal Transduction by $GABA_B$ Receptor Heterodimers", NeuroPsychopharmacology, 2000, ?vol. 23, No. S4, S41-S49.

Jordan et al., "G-protein-coupled Receptor heterodimerization Modulates Receptor Function"Nature, Jun. 17, 1999, vol. 399, 697-700.

McVey et al, "Monitoring Receptor Oligomeirzation Using Time-resolved Fluorescence Resonance Energy Transfer and Bioluminescence Resonance Energy Transfer", The Journal of Biological Chemistry, Apr. 27, 2001, vol. 276, No. 17, 14092-14099.

Devi, "Heterodimerization of G-protein-coupled Receptors: Pharmacology, Signaling and Trafficking", Trends in Pharmacological Science, Oct. 2001, vol. 22, No. 10, 532-537.

George et al, "G-protein-coupled Receptor Oligomerization and Its Potential for Durg Discovery", Nature Reviews/Drug Discoveries, Oct. 2002, vol. 1, 808-820.

Rios et al, "G-protein-coupled Receptor Dimerization: Modulatio of Receptor Function", Pharmacology & Therapeutics, 2001, vol. 92, 71-87.

Schlessinger, Ligan'induced, Receptor-mediated Dimerization and Activation, Cell, Sep. 20, 2002, vol. 110, 669-672.

Haff et al, "Multiplex Genotyping of PCR Products with Mass Tag-labeled Primers", Nucleic Acids Research, 1997, vol. 25, No. 18.

* cited by examiner

Thiazole cleavable linkage

Oxazole cleavable linkage

Olefin cleavable linkage

Thioether cleavable linkage

Synthesis of molecular tags labeled with fluorescein

Pro1-NHS

Pro2-NHS

Pro3-NHS

Pro4-NHS

Pro5-NHS

Pro6-NHS

Pro7-NHS

Pro8-NHS

Pro9-NHS

Pro10-NHS

Pro11-NHS

Pro12-NHS

Pro13-NHS

Pro14-NHS

Pro15-NHS

Pro16-NHS

Pro17-NHS

Pro18-NHS

Pro19-NHS

Pro20-NHS

Pro21-NHS

Pro22-NHS

Pro23-biotin

Pro24-biotin

Pro25-biotin

Pro26-biotin

Pro27-biotin

Pro28-NHS

Pro28-biotin

Pro29-NHS

Pro29-biotin

Pro30-NHS

Pro30-biotin

Pro31-NHS

Pro32-NHS

Pro32-biotin

Pro33-NHS

Pro33-biotin

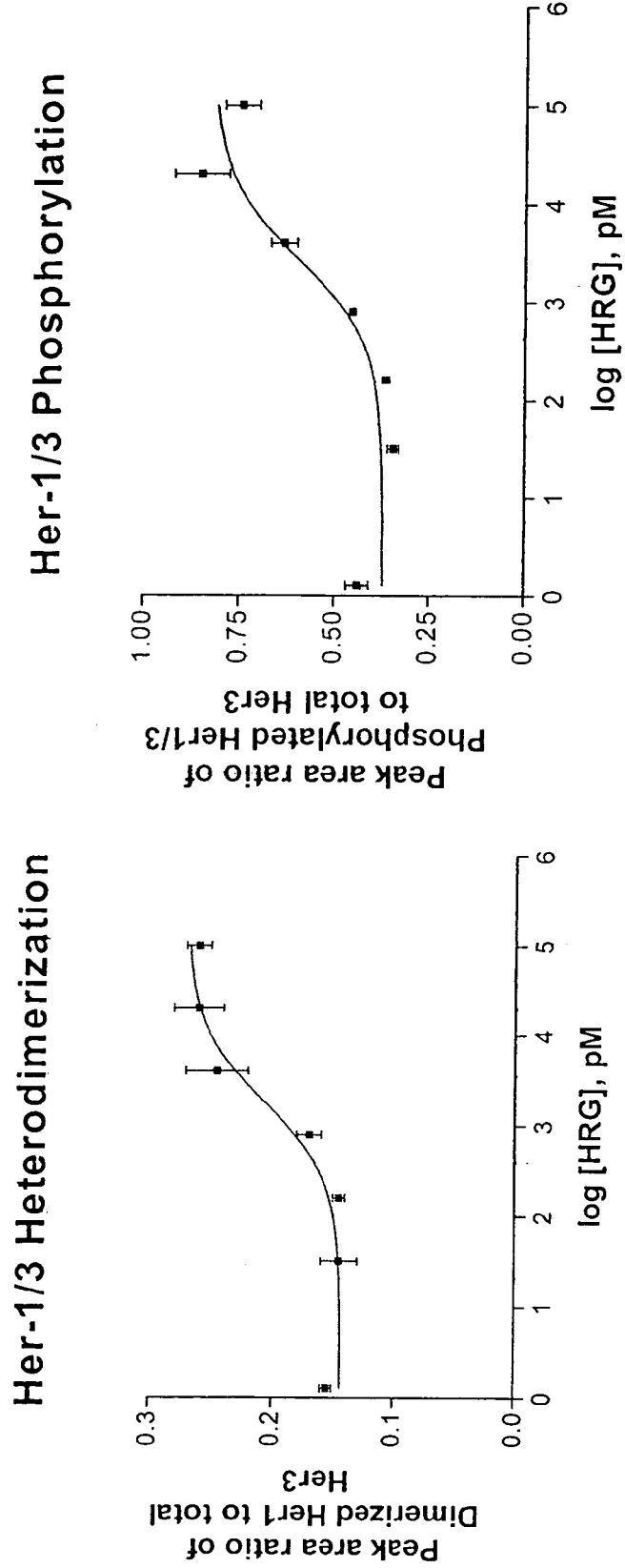
Fig. 13A Her-1/3 Heterodimerization
Fig. 13B Her-1/3 Phosphorylation

US 7,105,308 B2

DETECTING RECEPTOR OLIGOMERIZATION

This patent application claims priority from U.S. Provisional Application Ser. No. 60/398,724 filed Jul. 25, 2002, which is incorporated herein by reference in its entirety.

FIELD OF THE INVENTION

The present invention relates to methods for measuring oligomerization of cell surface molecules, particularly cell surface membrane receptors.

BACKGROUND OF THE INVENTION

The interactions of cell surface membrane components play crucial roles in transmitting extracellular signals to a cell in normal physiology, and in disease-conditions. In particular, many types of cell surface receptors undergo dimerization or oligomerization in connection with the transduction of an extracellular event or signal, e.g. ligand-receptor binding, into a cellular response, such as proliferation, increased or decreased gene expression, or the like, e.g. George et al, Nature Reviews Drug Discovery, 1: 808–820 (2002); Mellado et al, Ann. Rev. Immunol., 19: 397–421 (2001); Schlessinger, Cell, 103: 211–225 (2000); Yarden, Eur. J. Cancer, 37: S3–S8 (2001). The role of such signal transduction events in diseases, such as cancer, has been the object of intense research and has led to the development of several new drugs and drug candidates, e.g. Herbst and Shin, Cancer, 94: 1593–1611 (2002); Yarden and Sliwkowski, Nature Reviews Molecular Cell Biology, 2: 127–137 (2001).

A wide variety of techniques have been used to study dimerization and oligomerization of cell surface receptors, including immunoprecipitation, chemical cross-linking, bioluminescence resonance energy transfer (BRET), fluorescence resonance energy transfer (FRET), and the like, e.g. Price et al, Methods in Molecular Biology, 218: 255–267 (2003); McVey et al, J. Biol. Chem., 17: 14092–14099 (2001); Salim et al, J. Biol. Chem., 277: 15482–15485 (2002); Angers et al, Proc. Natl. Acad. Sci., 97: 3684–3689 (2000). Unfortunately, despite the importance of receptor dimerization and oligomerization in signal transduction processes, the techniques for measuring such interactions are difficult to apply, lack flexibility, and lack sensitivity. The lack of a convenient and sensitive technique for analyzing the oligomerization of cell surface molecules has greatly increased the difficulty of developing new therapeutics or diagnostic methods based on such phenomena.

In view of the above, the availability of a convenient, sensitive, and cost effective technique for detecting or measuring the dimerization or oligomerization of cell surface analytes would advance the art in many fields where such measurements are becoming increasingly important, including life science research, medical research and diagnostics, drug discovery, and the like.

SUMMARY OF THE INVENTION

The invention provides methods of detecting and/or measuring oligomers of membrane-bound molecules, and especially, dimers and oligomers of cell membrane receptors. In one aspect, the method of the invention uses at least two reagents that are specific for different members of a dimer or oligomer: one member, referred to herein as a cleaving probe, has a cleavage-inducing moiety that may be induced to cleave susceptible bonds within its immediate proximity; and the other member, referred to herein as a binding compound, has one or more molecular tags attach by linkages that are cleavable by the cleavage-inducing moiety. In accordance with the method, whenever such different members form a dimer or oligomer, the cleavable linkages are brought within the effective cleaving proximity of the cleavage-inducing moiety so that molecular tag can be released. The molecular tags are then separated from the reaction mixture and quantified to provide a measure of dimerization or oligomerization.

In another aspect, the method of the invention comprises the following steps: providing a cleaving probe specific for a first receptor type of a plurality of receptor types, the cleaving probe having a cleavage-inducing moiety with an effective proximity; providing one or more binding compounds each specific for a different second receptor type of the plurality, each binding compound having one or more molecular tags each attached thereto by a cleavable linkage, and the molecular tags of different binding compounds having different separation characteristics; mixing the cleaving probe, the one or more binding compounds, and a cell membrane containing the first and second receptor types such that the cleaving probe and the one or more binding compounds specifically bind to their respective receptors and the cleavable linkages of the one or more binding compounds are within the effective proximity of the cleavage-inducing moiety so that molecular tags are released; and separating and identifying the released molecular tags to determine the presence or absence or the amount of oligomerization of the receptor types in the cell membrane.

In another aspect, the invention provides a method of detecting dimers of membrane-associated analytes in a cell membrane, the method comprising the steps of: providing a binding compound specific for a first membrane-associated analyte of a dimer, the dimer comprising the first membrane-associated analyte and a second membrane-bound analyte, and the binding compound having one or more molecular tags each attached thereto by a cleavable linkage, the one or more molecular tags each having a separation characteristic; providing a cleaving probe specific for the second membrane-bound analyte, the cleaving probe having a cleavage-inducing moiety with an effective proximity; mixing the cleaving probe, the binding compound, and the cell membrane such that the cleaving probe specifically binds to the first membrane-associated analyte and the binding compound specifically binds to the second membrane-associated analyte and such that cleavable linkages of the binding compound are within the effective proximity of the cleavage-inducing moiety so that molecular tags are released; and separating and identifying the released molecular tags to determine the presence or absence or the amount of dimer in the cell membrane.

In another aspect, the invention provides a method for profiling the frequencies of dimers among a plurality of receptor types on the surfaces of cells.

In another aspect, the invention includes kits for carrying out the methods of the invention. In one embodiment, kits of the invention include one or more binding compounds and a cleaving probe. In another embodiment, such one or more binding compounds and cleaving probe are each specific for a different antigenic determinant of a dimer comprising receptors selected from the group consisting of Her1, Her2, Her3, and Her4. More particularly, such one or more binding compounds and cleaving probe are each specific for a different antigenic determinant of a dimer selected from the group consisting of a dimer of Her1, a dimer of Her2, a dimer comprising Her1 and Her2, a dimer comprising Her1 and Her3 and a dimer comprising Her2 and Her3.

The present invention provides a method of detecting or measuring the dimerization or oligomerization of membrane-associated analytes that has several advantages over current techniques including, but not limited to, (1) the detection and/or measurement of molecular tags that are separated from an assay mixture provide greatly reduced background and a significant gain in sensitivity; and (2) the use of molecular tags that are specially designed for ease of separation and detection thereby providing convenient multiplexing capability.

BRIEF DESCRIPTION OF THE DRAWINGS

FIGS. 13A–13B show data from assays of the invention that detect heterodimers of Her1 and Her3 on cells.

DEFINITIONS

Figure 1A:
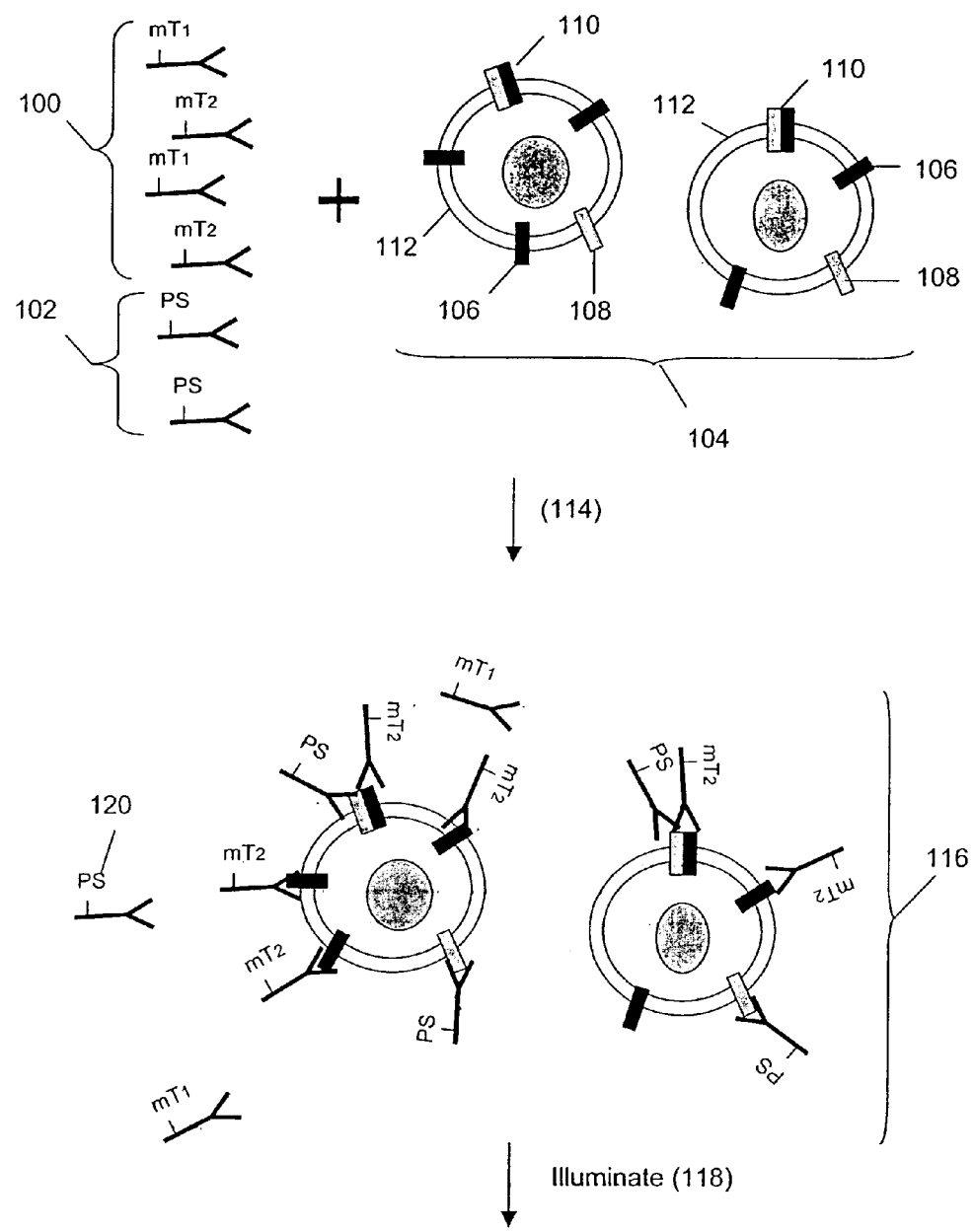
FIGS. 1A and 1B illustrate diagrammatically an embodiment of the method of the invention for measuring the presence of receptor dimers on the surfaces of biological cells.

"Antibody" means an immunoglobulin that specifically binds to, and is thereby defined as complementary with, a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgGG, IgG2a, IgG2b and IgG3, IgM, etc. Fragments thereof may include Fab, Fv and F(ab')2, Fab', and the like. In addition, aggregates, polymers, and conjugates of immunoglobulins or their fragments can be used where appropriate so long as binding affinity for a particular polypeptide is maintained.

"Antibody binding composition" means a molecule or a complex of molecules that comprise one or more antibodies and derives its binding specificity from an antibody. Antibody binding compositions include, but are not limited to, antibody pairs in which a fist antibody binds specifically to a target molecule and a second antibody binds specifically to a constant region of the first antibody; a biotinylated antibody that binds specifically to a target molecule and streptavidin derivatized with moieties such as molecular tags or photosensitizers; antibodies specific for a target molecule and conjugated to a polymer, such as dextran, which, in turn, is derivatized with moieties such as molecular tags or photosensitizers; antibodies specific for a target molecule and conjugated to a bead, or microbead, or other solid phase support, which, in turn, is derivatized with moieties such as molecular tags or photosensitizers, or polymers containing the latter.

"Antigenic determinant," or "epitope" means a site on the surface of a membrane-associated analyte to which a single antibody molecule binds; generally a membrane-associated analyte has several or many different antigenic determinants and reacts with antibodies of many different specificities. When membrane-associated analytes are cell surface receptors involved in signal transduction processes, a preferred antigenic determinant is a phosphorylation site of a receptor.

"Binding moiety" means any molecule to which molecular tags can be directly or indirectly attached that is capable of specifically binding to a membrane-associated analyte. Binding moieties include, but are not limited to, antibodies, antibody binding compositions, peptides, proteins, particularly secreted proteins and orphan secreted proteins, nucleic acids, and organic molecules having a molecular weight of up to 1000 daltons and consisting of atoms selected from the group consisting of hydrogen, carbon, oxygen, nitrogen, sulfur, and phosphorus.

"Capillary-sized" in reference to a separation column means a capillary tube or channel in a plate or microfluidics device, where the diameter or largest dimension of the separation column is between about 25–500 microns, allowing efficient heat dissipation throughout the separation medium, with consequently low thermal convection within the medium.

"Chromatography" or "chromatographic separation" as used herein means or refers to a method of analysis in which the flow of a mobile phase, usually a liquid, containing a mixture of compounds, e.g. molecular tags, promotes the separation of such compounds based on one or more physical or chemical properties by a differential distribution between the mobile phase and a stationary phase, usually a solid. The one or more physical characteristics that form the basis for chromatographic separation of analytes, such as molecular tags, include but are not limited to molecular weight, shape, solubility, pKa, hydrophobicity, charge, polarity, and the like. In one aspect, as used herein, "high pressure (or performance) liquid chromatography" ("HPLC") refers to a liquid phase chromatographic separation that (i) employs a rigid cylindrical separation column having a length of up to 300 mm and an inside diameter of up to 5 mm, (ii) has a solid phase comprising rigid spherical particles (e.g. silica, alumina, or the like) having the same diameter of up to 5 Wn packed into the separation column, (iii) takes place at a temperature in the range of from 35° C. to 80° C. and at column pressure up to 150 bars, and (iv) employs a flow rate in the range of from 1 μL/min to 4 mL/min. Preferably, solid phase particles for use in HPLC are further characterized in (i) having a narrow size distribution about the mean particle diameter, with substantially all particle diameters being within 10% of the mean, (ii) having the same pore size in the range of from 70 to 300 angstroms, (iii) having a surface area in the range of from 50 to 250 $m^2$/g, and (iv) having a bonding phase density (i.e. the number of retention ligands per unit area) in the range of from 1 to 5 per $nm^2$. Exemplary reversed phase chromatography media for separating molecular tags include particles, e.g. silica or alumina, having bonded to their surfaces retention ligands, such as phenyl groups, cyano groups, or aliphatic groups selected from the group including $C_8$ through $C_{18}$. Chromatography in reference to the invention includes "capillary electrochromatography" ("CEC"), and related techniques. CEC is a liquid phase chromatographic technique in which fluid is driven by electroosmotic flow through a capillary-sized column, e.g. with inside diameters in the range of from 30 to 100 Jim. CEC is disclosed in Svec, Adv. Biochem. Eng. Biotechnol. 76: 1–47 (2002); Vanhoenacker et al, Electrophoresis, 22: 4064–4103 (2001); and like references. CEC column may use the same solid phase materials as used in conventional reverse phase HPLC and additionally may use so-called "monolithic" non-particular packings. In some forms of CEC, pressure as well as electroosmosis drives an analyte-containing solvent through a column.

As used herein, the term "kit" refers to any delivery system for delivering materials. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

The term "ligand" is also used herein to refer to a secreted protein or protein thereof which binds to a given receptor, through a ligand-receptor interaction.

"Membrane-associated analyte" means a substance, compound, molecule, or component or part of any of the foregoing that is directly or indirectly attached to a membrane, especially a biological membrane such as the cell surface membrane of a mammalian cell or tissue. The attachment may be direct, for example, when a membrane-associated analyte has a lipophilic moiety, or is attached to another molecule that has a lipophilic moiety, capable of anchoring it in a membrane. The attachment may also be indirect, for example, when a membrane-associated analyte is a soluble ligand that binds to, and forms a stable complex with, a cell surface receptor. A membrane-associated analyte may be, but is not limited to, a peptide, protein, polynucleotide, polypeptide, oligonucleotide, organic molecule, hapten, epitope, part of a biological cell, a posttranslational modification of a protein, a receptor, a complex sugar attached to a membrane component such as a receptor, a soluble compound forming a stable complex with a membrane such as a vitamin, a hormone, a cytokine, or the like, forming and the like. There may be more than one analyte associated with a single molecular entity, e.g. different phosphorylation sites on the same protein. Membrane-associated analytes include cell surface molecules, such as cell membrane receptors. In one aspect of the invention, membrane-associated analytes are cell membrane receptors selected from the group consisting of epidermal growth factor receptors and G-protein coupled receptors. In particular, epidermal growth factor receptors include Her1, Her2, Her3, and Her4 receptors, e.g. Yarden (cited above); Yarden and Sliwkowski (cited above). "Dimer" in reference to membrane-associated analytes means a stable, usually non-covalent, association of two membrane-associated analytes. A dimer of membrane-associated analytes may form as the result of interaction with a ligand, i.e. ligand-induced dimerization, e.g. Schlessinger, Cell, 110: 669–672 (2002). "Oligomer" in reference to membrane-associated analytes means a stable, usually non-covalent, association of at least two membrane-associated analytes.

"Polypeptide" refers to a class of compounds composed of amino acid residues chemically bonded together by amide linkages with elimination of water between the carboxy group of one amino acid and the amino group of another amino acid. A polypeptide is a polymer of amino acid residues, which may contain a large number of such residues. Peptides are similar to polypeptides, except that, generally, they are comprised of a lesser number of amino acids. Peptides are sometimes referred to as oligopeptides. There is no clear-cut distinction between polypeptides and peptides. For convenience, in this disclosure and claims, the term "polypeptide" will be used to refer generally to peptides and polypeptides. The amino acid residues may be natural or synthetic.

"Protein" refers to a polypeptide, usually synthesized by a biological cell, folded into a defined three-dimensional structure. Proteins are generally from about 5,000 to about 5,000,000 or more in molecular weight, more usually from about 5,000 to about 1,000,000 molecular weight, and may include posttranslational modifications, such acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, phosphorylation, prenylation, racemization, selenoylation, sulfation, and ubiquitination, e.g. Wold, F., Post-translational Protein Modifications: Perspectives and Prospects, pgs. 1–12 in Post-translational Covalent Modification of Proteins, B. C. Johnson, Ed., Academic Press, New York, 1983. Proteins include, by way of illustration and not limitation, cytokines or interleukins, enzymes such as, e.g., kinases, proteases, galactosidases and so forth, protamines, histones, albumins, immunoglobulins, scleroproteins, phosphoproteins, mucoproteins, chromoproteins, lipoproteins, nucleoproteins, glycoproteins, T-cell receptors, proteoglycans, unclassified proteins, e.g., somatotropin, prolactin, insulin, pepsin, proteins found in human plasma, blood clotting factors, blood typing factors, protein hormones, cancer antigens, tissue specific antigens, peptide hormones, nutritional markers, tissue specific antigens, and synthetic peptides.

The term "sample" means a quantity of material that is suspected of containing membrane-associated analytes that are to be detected or measured. As used herein, the term includes a specimen (e.g., a biopsy or medical specimen) or a culture (e.g., microbiological culture). It also includes both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention. In particular, biological samples include fixed biological specimens, such as patient biopsy specimens treated with a fixative, biological specimens embedded in paraffin, frozen biological specimens, smears, and the like.

A "separation profile" in reference to the separation of molecular tags means a chart, graph, curve, bar graph, or other representation of signal intensity data versus a parameter related to the molecular tags, such as retention time, mass, or the like, that provides a readout, or measure, of the number of molecular tags of each type produced in an assay. A separation profile may be an electropherogram, a chromatogram, an electrochromatogram, a mass spectrogram, or like graphical representation of data depending on the separation technique employed. A "peak" or a "band" or a "zone" in reference to a separation profile means a region where a separated compound is concentrated. There may be multiple separation profiles for a single assay if, for example, different molecular tags have different fluorescent labels having distinct emission spectra and data is collected and recorded at multiple wavelengths. In one aspect, released molecular tags are separated by differences in electrophoretic mobility to form an electropherogram wherein different molecular tags correspond to distinct peaks on the electropherogram. A measure of the distinctness, or lack of overlap, of adjacent peaks in an electropherogram is "electrophoretic resolution," which may be taken as the distance between adjacent peak maximums divided by four times the larger of the two standard deviations of the peaks. Preferably, adjacent peaks have a resolution of at least 1.0, and more preferably, at least 1.5, and most preferably, at least 2.0. In a given separation and detection system, the desired resolution may be obtained by selecting a plurality of molecular tags whose members have electrophoretic mobilities that differ by at least a peak-resolving amount, such quantity depending on several factors well known to those of ordinary skill, including signal detection system, nature of the fluorescent moieties, the diffusion coefficients of the tags, the presence or absence of sieving matrices, nature of the electrophoretic apparatus, e.g. presence or absence of channels, length of separation channels, and the like.

"Specific" or "specificity" in reference to the binding of one molecule to another molecule, such as a binding compound, or probe, for a target analyte, means the recognition, contact, and formation of a stable complex between the probe and target, together with substantially less recognition, contact, or complex formation of the probe with other molecules. In one aspect, "specific" in reference to the binding of a first molecule to a second molecule means that to the extent the first molecule recognizes and forms a complex with another molecules in a reaction or sample, it forms the largest number of the complexes with the second molecule. In one aspect, this largest number is at least fifty percent of all such complexes form by the first molecule. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, ionic and hydrophobic interactions, and the like, dominate the interaction of the molecules. As used herein, "stable complex" in reference to two or more molecules means that such molecules form noncovalently linked aggregates, e.g. by specific binding, that under assay conditions are thermodynamically more favorable than a non-aggregated state.

As used herein, the term "spectrally resolvable" in reference to a plurality of fluorescent labels means that the fluorescent emission bands of the labels are sufficiently distinct, ie. sufficiently non-overlapping, that molecular tags to which the respective labels are attached can be distinguished on the basis of the fluorescent signal generated by the respective labels by standard photodetection systems, e.g. employing a system of band pass filters and photomultiplier tubes, or the like, as exemplified by the systems described in U.S. Pat. Nos. 4,230,558; 4,811,218, or the like, or in Wheeless et al, pgs. 21–76, in Flow Cytometry: Instrumentation and Data Analysis (Academic Press, New York, 1985).

The term "secreted protein," or "soluble protein," refers to proteins that are (i) expressed intracellularly, (ii) secreted from the cell into the extracellular medium, e.g., typically requiring a leader sequence that directs the expressed protein from the endoplasmic reticulum through the cell membrane, and (iii) act on a receptor, typically a cell-surface receptor, to effect or initiate some cellular event or activity, which may be an intracellular event, including cell proliferation or stimulation, a cell-surface event, or cell-cell interaction event.

As used herein, the term "tagged probe" refers to a probe for use in the present invention that binds to a target molecule on the surface of a cell membrane, i.e. membrane-associated analyte, and which comprises one or more molecular tags linked to a binding agent of the probe through a cleavable linkage. As used herein, "tagged probe" is used synonymously with "binding compound."

DETAILED DESCRIPTION OF THE INVENTION

In one aspect, the present invention is directed to methods for determining the presence and/or amount of dimers or oligomers of one or more membrane-associated analytes in a sample by selectively releasing molecular tags from binding compounds that form stable complexes together with the membrane-associated analytes and a cleaving probe. An important feature of this aspect of the invention includes the limited cleavage of molecular tags from binding compounds in such complexes that are in the immediate proximity of the cleaving probe, but substantially no cleavage of molecular tags of binding compounds that do not form such complexes. That is, cleaving probes comprise a cleavage-inducing moiety that may be induced to cleave certain linkages that are within its immediate proximity. As disclosed more fully below, such local cleavage is accomplished by using cleavage-inducing moieties referred to herein as "sensitizers" that may be induced to generate an active species, that is, a diffusible, short-lived, reactive chemical entity, that is capable of reacting with the cleavable linkages of molecular tags to bring about their release from a binding compound.

Figure 1B:
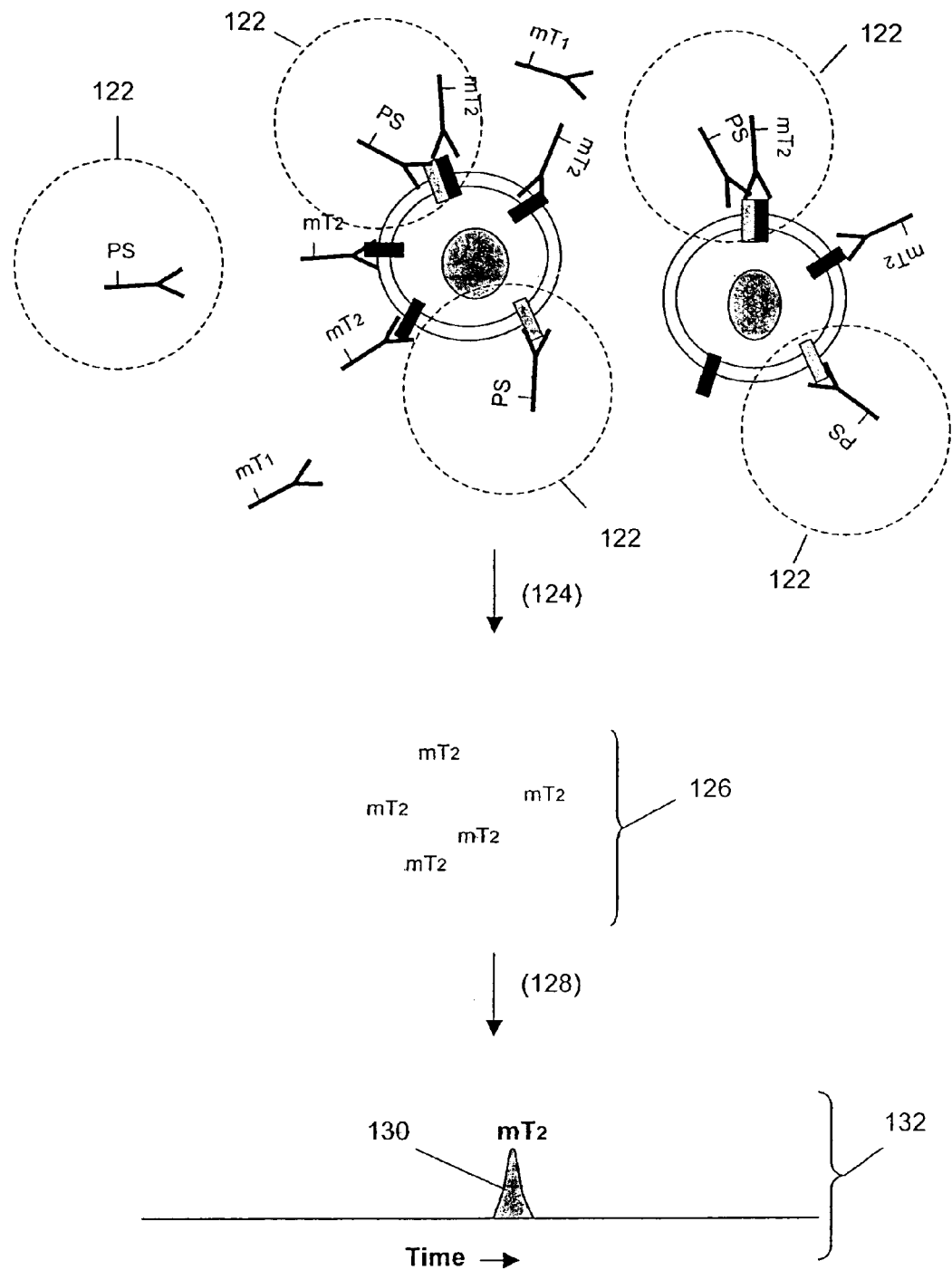

An illustration of one embodiment of the invention is presented diagrammatically in FIGS. 1A and 1B. Binding compounds (100) having molecular tags "$mT_1$" and "$mT_2$" and cleaving probe (102) having photosensitizer "PS" are combined with biological cells (104). Binding compounds having molecular tag "$mT_1$" are specific for cell surface receptors $R_1$ (106) and binding compounds having molecular tag "$mT_2$" are specific for cell surface receptors $R_2$ (108). Cell surface receptors $R_1$ and $R_2$ are present as monomers, e.g. (106) and (108), and as dimers (110) in cell surface membrane (112). After these assay components are incubated in a suitable binding buffer to permit the formation (114) of stable complexes between binding compounds and their respective receptor targets and between the cleaving probe and its receptor target. As illustrated, preferably binding compounds and cleaving probes each comprise an antibody binding composition, which permits the molecular tags and cleavage-inducing moiety to be specifically targeted to membrane components. In one aspect, such antibody binding compositions are monoclonal antibodies. In such embodiments, binding buffers may comprise buffers used in conventional ELISA techniques, or the like. After binding compounds and cleaving probes for stable complexes (116), the assay mixture is illuminated (118) to induce photosensitizers (120) to generate singlet oxygen. Singlet oxygen rapidly reacts with components of the assay mixture so that its effective proximity (122) for cleaving cleavable linkages of molecular tags is spatially limited so that only molecular tags that happen to be within the effective proximity are released (124). As illustrated, the only molecular tags released are those on binding compounds that form stable complexes with $RI-R_2$ dimers and a cleaving probe. Released molecular tags (126) are removed from the assay mixture and separated (128) in accordance with a separation characteristic so that a distinct peak (130) is formed in a separation profile (132). In accordance with the invention, such removal and separation may be the same step. Optionally, prior to illumination the binding buffer may be removed and replaced with a buffer more suitable for separation, i.e. a separation buffer. For example, binding buffers typically have salt concentrations that may degrade the performance of some separation techniques, such as capillary electrophoresis, for separating molecular tags into distinct peaks. In one embodiment, such exchange of buffers may be accomplished by membrane filtration.

Figure 2A:
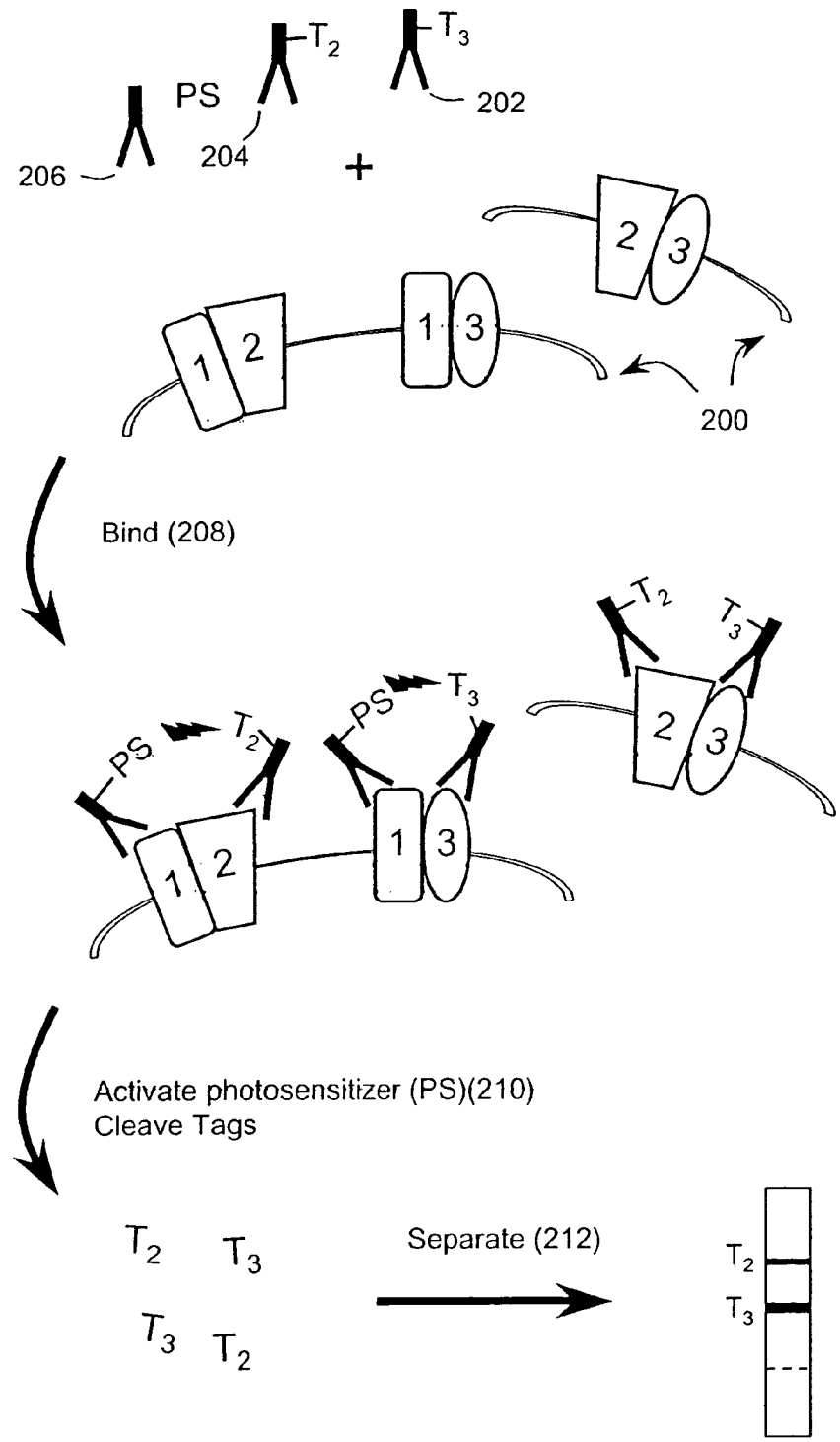
FIGS. 2A–2E illustrate diagrammatically an embodiment of the method of the invention for profiling frequencies of dimers of a plurality of receptor types.

FIGS. 2A–2E illustrate another embodiment of the invention for profiling dimerization among a plurality of receptor types. FIG. 2A outlines the basic steps of such an assay. Cell membranes (200) that are to be tested for dimers of cell surface receptors are combined with sets of binding compounds (202) and (204) and cleaving probe (206). Membrane fractions (200) contain three different types of monomer receptor molecules ("1," "2," and "3") in its cell membrane which associate to form three different heterodimers: 1-2, 1-3, and 2-3. Three antibody reagents (202) and (204) are combined with membrane fraction (200), each of the antibody reagents having binding specificity for one of the three receptor molecules, where antibody (206) is specific for receptor molecule 1, antibody (204) is specific for receptor molecule 2, and antibody (202) is specific for receptor molecule 3. The antibody for the first receptor molecule is covalently coupled to a photosensitizer molecule, labeled PS. The antibodies for the second and third receptor molecules are linked to two different tags, labeled $T_2$ and $T_3$, respectively, through a linkage that is cleavable by an active species generated by the photosensitizer moiety.

After mixing, the antibodies are allowed to bind (208) to molecules on the surface of the membranes. The photosensitizer is activated (210), cleaving the linkage between tags and antibodies that are within an actionable distance from a sensitizer molecule, thereby releasing tags into the assay medium. Material from the reaction is then separated (212), e.g., by capillary electrophoresis, as illustrated. As shown at the bottom of FIG. 2A, the tags $T_2$ and $T_3$ are released, and separation by electrophoresis will reveal two bands corresponding to these tags. Because the tags are designed to have a known electrophoretic mobility, each of the bands can be uniquely assigned to one of the tags used in the assay.

Figures 2B, 2C:
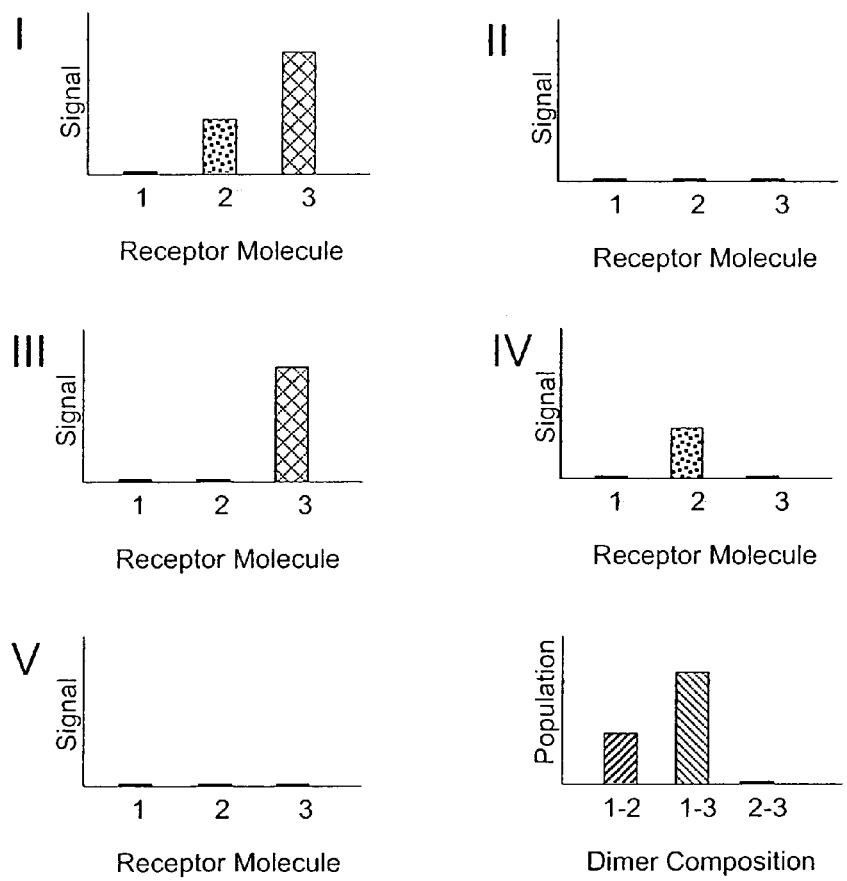

As shown in FIG. 2A, only two of the three different heterodimers that are present in the cell membrane will bind both a photosensitizer-containing antibody and a tag-containing antibody, and thus only these two species should give rise to released tags. However, multiple experiments are required to measure the relative amounts of the different dimers. FIG. 2B provides a table listing five different assay combinations. In FIG. 2C are the illustrative results for each assay composition. Assay I represents the results from the complete assay, as described in FIG. 2A. In Assay II, the antibody specific for receptor molecule 1, which is linked to the photosensitizer, is omitted. This assay yields no signal, indicating that the $T_2$ and $T_3$ signals obtained in Assay I require the photosensitizer reagent. Similarly, Assay V shows that the tag signals require the presence of the membranes. Assays III and IV show that each tagged reagent does not require the presence of the other to be cleaved. These results, when considered together, allow one to draw conclusions regarding the presence and composition of receptor heterodimers present in the membrane, as given in FIG. 2C, i.e., that both the 1-2 and the 1-3 heterodimer are present. Furthermore, the relative signal intensities from each tag allow one to estimate the relative abundance of each of the heterodimers.

Figure 2D:
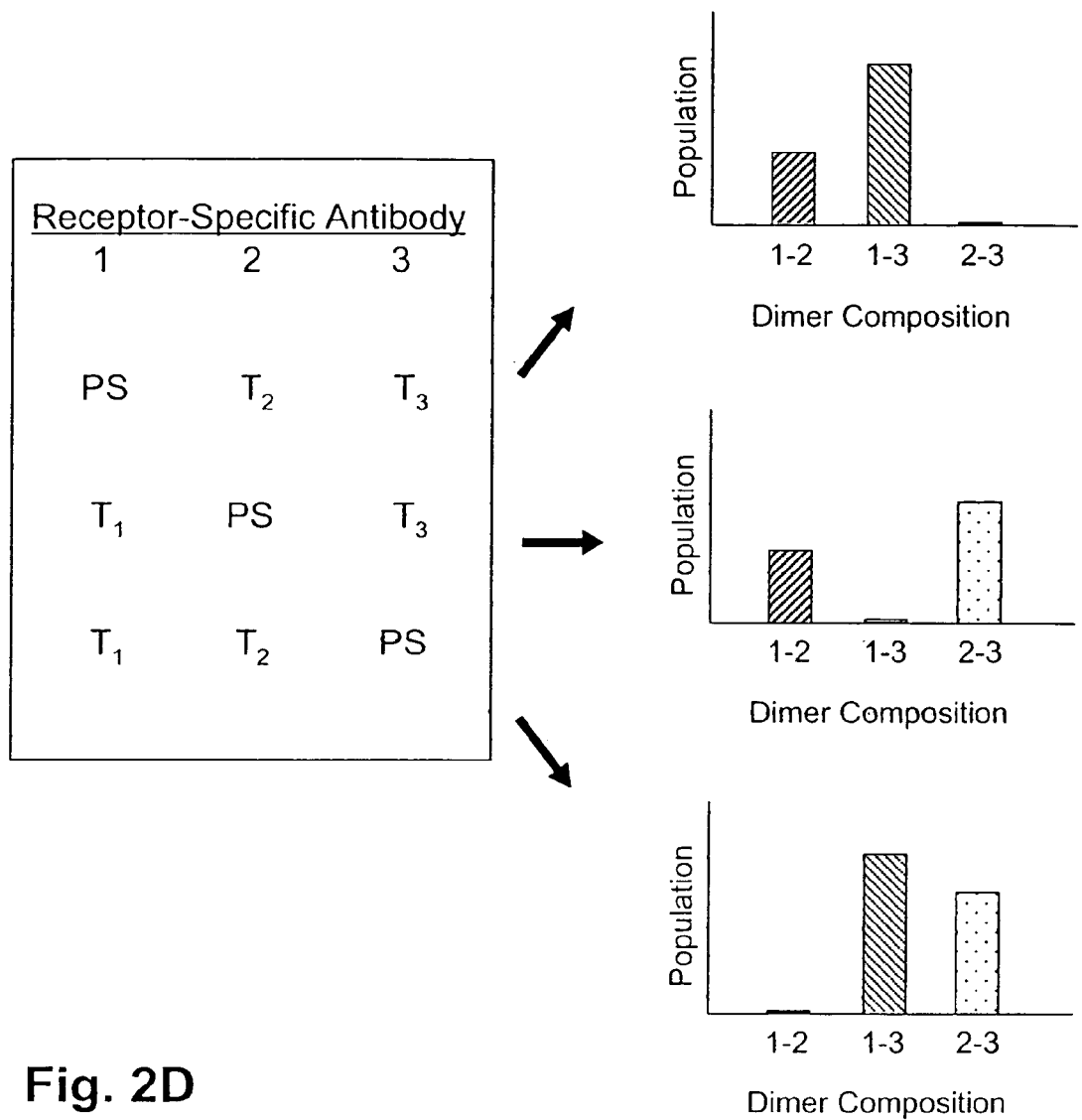
Figure 2E:
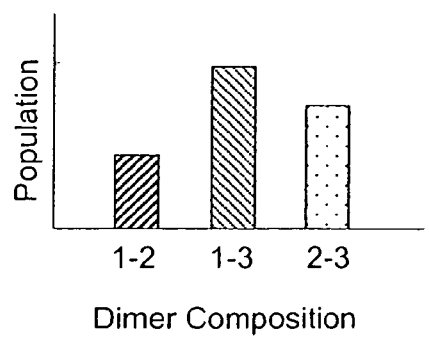

A conclusion regarding existence of the 2-3 heterodimer cannot be made with the combination of reagents used in this assay, however. No signal representing this complex will be obtained, whether or not the complex is present, because it will not have a photosensitizer reagent bound to it. In order to draw conclusions regarding every possible dimeric combination of the three monomers, either a fourth reagent must be used that can be localized to every possible oligomer comprising monomers 1, 2, and/or 3, or the three binding agents used in this experiment must be coupled in different combinations to tags and sensitizer molecules. The later strategy is illustrated in FIGS. 2D and 2E. Three possible combinations of photosensitizer and tag distribution among the three antibody reagents are listed in the table on the left of FIG. 2D. The first combination comprises a photosensitizer coupled to the antibody specific for monomer number 1, and is the same combination used in the illustration of FIGS. 2A–2C, and has the same dimer population as in FIG. 2C. The second combination comprises a photosensitizer coupled to the antibody specific for monomer number 2, and the population profile yields the same number for heterodimer 1-2, plus a value for heterodimer 2-3. The third combination comprises a photosensitizer coupled to the antibody specific for monomer number 3, and the population profile yields the same number for heterodimer 1-3 and 2-3 as obtained from the first two combinations. These results can be combined to yield the overall heterodimer population profile given in FIG. 2E.

As mentioned above, another aspect of the present invention is directed to determining formation of one or more oligomeric complexes of cell surface molecules in cell membranes. Complexes that may be determined include homo-oligomers comprising two or more molecules of a single molecular species, and hetero-oligomers comprising two or more different molecular species. Preferred classes of cell surface molecules include receptors, particularly members of the G-protein coupled receptor family and members of the epidermal growth factor receptor family.

The methods of the invention comprise contacting at least two cell surface molecules with two distinct binding agents, a first conjugated to a tag through a cleavable linkage, where the tag comprises a detection group, and a second conjugated to a cleaving agent that is capable of cleaving the cleavable linkage when the linkage is within a proximity of the cleaving agent that is effective for the reaction. This reactive region is referred to as the "effective proximity" of the cleaving agent. Release of the tag by the cleaving agent indicates localization of the tagged probe within the effective proximity of the cleaving probe. A preferred composition of first and second binding agents is antibody molecules, more preferably monoclonal antibodies. A preferred detection group is a fluorophore. A preferred embodiment of a cleaving agent is a sensitizer molecule that can be activated to produce an active cleaving species. More preferably, the cleaving agent comprises a photosensitizer that is activated by light to produce an oxidant that cleaves an oxidation-labile linkage conjugating the tag to the first binding agent of the tagged probe.

In another aspect of the invention where one desires to determine formation of a plurality of cell surface complexes or formation of a single cell surface complex comprising a plurality of different molecular species, the methods employ a plurality of first binding agents, each conjugated to a distinct tag, thereby forming a plurality of tagged probes. Each tag in the plurality of tags will comprise a detection group and a mobility modifier providing means for distinguishing each releasable tag from all other releasable tags in the plurality. One preferred means of distinguishing the released tags is physical separation by electrophoresis, wherein the mobility modifiers confer differences in electrophoretic mobility. Preferred modes of electrophoresis include capillary electrophoresis, including both conventional capillary electrophoresis and separations on microfluidic cards. Other preferred means of distinguishing include spectral resolution based on differences in the optical properties of the detection groups of the tags, and physical separation by mass spectrometry based on differences in the mass of the tags.

Another aspect of the present invention is directed to determining the effect of a compound on formation of an oligomeric complex at the surface of cell membranes. These methods comprise preparing two combinations of cell membranes, tagged probes, and cleaving probes, wherein a compound is added to one of the two combinations. After incubation to allow cleavage of the tagged probe, the amount of tag released in each combination is detected, and the two mixtures are compared. The invention further provides methods for determining the effect of a compound on formation of a plurality of cell surface complexes.

In another aspect, the invention includes a method for determining formation of an oligomeric complex comprising a first and second cell surface molecule in a cell membrane, the method comprising the steps: (a) mixing under binding conditions: (i) the cell membrane, (ii) a tagged probe comprising a first binding agent capable of binding specifically to the first cell surface molecule and at least one molecule of a tag comprising a detection group, the tag being conjugated through a cleavable linkage to the first binding agent, and (iii) a cleaving probe comprising a second binding agent capable of binding specifically to the second cell surface molecule and a cleaving agent capable of cleaving the cleavable linkage when within an effective proximity, wherein when the oligomeric complex is formed in the cell membrane and is bound by both the tagged probe and the cleaving probe, at least one cleavable linkage of the tagged probe is within the effective proximity of the cleaving agent; (b) incubating the mixture under conditions that allow cleavage of the cleavable linkage that is within the effective proximity of the cleaving agent, thereby releasing the tag from the tagged probe; and (c) detecting the released tag, thereby determining formation of the oligomeric complex.

In another aspect, the invention includes a method for determining formation of one or more oligomeric complexes, each oligomeric complex comprising a first and second cell surface molecule in a cell membrane, the method comprising the steps: (a) mixing under binding conditions: (i) the cell membrane, (ii) a plurality of tagged probes, each tagged probe comprising a first binding agent capable of binding specifically to one of a set of the first cell surface molecules, and at least one molecule of a tag from a set of tags, wherein the tag comprises a detection group and a mobility modifier providing means for distinguishing each tag from all other tags from the set, the tag being conjugated through a cleavable linkage to the first binding agent, and (iii) a cleaving probe comprising a second binding agent capable of binding specifically to the second cell surface molecule and a cleaving agent capable of cleaving the cleavable linkages when within an effective proximity, wherein when the oligomeric complex is formed in the cell membrane and is bound by both the tagged probe and the cleaving probe, at least one cleavable linkage of the tagged probe is within the effective proximity of the cleaving agent; (b) incubating the mixture under conditions that allow cleavage of the cleavable linkages that are within the effective proximity of the cleaving agent, to generate released tags from the tagged probes; (c) separating the released tags according to the means for distinguishing; and (d) detecting the separated tags, thereby determining formation of each of the oligomeric complexes.

In another aspect, the invention includes a method for determining the effect of a compound on formation of an oligomeric complex comprising a first and second cell surface molecule in a cell membrane, the method comprising the steps: (a) preparing two mixtures under binding conditions comprising: (i) the cell membrane, (ii) a tagged probe comprising a first binding agent capable of binding specifically to the first cell surface molecule and at least one molecule of a tag comprising a detection group, the tag being conjugated through a cleavable linkage to the first binding agent, and (iii) a cleaving probe comprising a second binding agent capable of binding specifically to the second cell surface molecule and a cleaving agent capable of cleaving the cleavable linkage when within an effective proximity, wherein when the oligomeric complex is formed in the cell membrane and is bound by both the tagged probe and the cleaving probe, at least one cleavable linkage of the tagged probe is within the effective proximity of the cleaving agent; (b) adding the compound to one of the two mixtures; (c) incubating the mixtures under conditions that allow cleavage of the cleavable linkage that is within the effective proximity of the cleaving agent, thereby releasing the tag from the tagged probe; (d) detecting and identifying the amount of the tag released in each of the two combinations in step (c); and (e) comparing the amount of tag released in the two mixtures, thereby determining the effect of the compound on formation of the oligomeric complex.

In another aspect, the invention includes a method for determining the effect of a compound on formation of any or all of a plurality of oligomeric complexes, each oligomeric complex comprising a first and second cell surface molecule in a cell membrane, the method comprising the steps: (a) preparing two mixtures under binding conditions comprising: (i) the cell membrane, (ii) a plurality of tagged probes, each tagged probe comprising a first binding agent capable of binding specifically to one of the first cell surface molecules of the plurality of oligomeric complexes, and at least one molecule of a tag from a set of tags, wherein the tag comprises a detection group and a mobility modifier providing means for distinguishing each tag from all other tags from the set, the tag being conjugated through a cleavable linkage to the first binding agent, and (iii) a cleaving probe comprising a second binding agent capable of binding specifically to one of the second cell surface molecules of the plurality of oligomeric complexes, and a cleaving agent capable of cleaving the cleavable linkages when within an effective proximity, wherein when the oligomeric complex is formed in the cell membrane and is bound by both the tagged probe and the cleaving probe, at least one cleavable linkage of the tagged probe is within the effective proximity of the cleaving agent; (b) adding the compound to one of the two mixtures; (c) incubating the mixtures under conditions that allow cleavage of the cleavable linkages that are within the effective proximity of the cleaving agent, thereby releasing the tags from the tagged probes; (d) separating the released tags according to the means for distinguishing; (e) detecting and identifying the amount of each of the separated tags released in each of the two mixtures in step (c); and (f) comparing the amount of each tag released in the two mixtures, thereby determining the effect of the compound on formation of the oligomeric complexes.

Samples containing target membrane-associated analytes may come from a wide variety of sources including cell cultures, animal or plant tissues, microorganisms, patient biopsies, or the like. Samples are prepared for assays of the invention using conventional techniques, which may depend on the source from which a sample is taken. Guidance for preparing cell membranes for analysis can be found in standard treatises, such as Sambrook et al, Molecular Cloning, Second Edition (Cold Spring Harbor Laboratory Press, New York, 1898); Innis et al, editors, PCR Protocols (Academic Press, New York, 1990); Berger and Kimmel, "Guide to Molecular Cloning Techniques ," Vol. 152, Methods in Enzymology (Academic Press, New York, 1987); Ohlendieck, K. (1996). Protein Purification Protocols; Methods in Molecular Biology, Humana Press Inc., Totowa, N.J. Vol 59: 293–304; Method Booklet 5, "Signal Transduction" (Biosource International, Camarillo, CA, 2002); or the like. For mammalian tissue culture cells, or like sources, samples of target membrane-associated analytes may be prepared by conventional cell lysis techniques (e.g. 0.14 M NaCl, 1.5 mM $MgCl_2$, 10 mM Tris-Cl (pH 8.6), 0.5% Nonidet P-40, and protease and/or phosphatase inhibitors as required). For biopsies and medical specimens: Bancroft J D & Stevens A, eds. Theory and Practice of Histological Techniques (Churchill Livingstone, Edinburgh, 1977); Pearse, Histochemistry. Theory and applied. $4^{th}$ ed. (Churchill Livingstone, Edinburgh, 1980)

As described more fully below, target membrane-associated analytes are determined by separation and identification of the released molecular tags. A wide variety of separation techniques may be employed that can distinguish molecules based on one or more physical, chemical, or optical differences among molecules being separated including but not limited to electrophoretic mobility, molecular weight, shape, solubility, pKa, hydrophobicity, charge, charge/mass ratio, polarity, or the like. In one aspect, molecular tags in a plurality differ in electrophoretic mobility and optical detection characteristics and are separated by electrophoresis. In another aspect, molecular tags in a plurality differ in molecular weight, shape, solubility, pKa, hydrophobicity, charge, polarity, and are separated by normal phase or reverse phase HPLC, ion exchange HPLC, capillary electrochromatography, mass spectroscopy, gas phase chromatography, or like technique.

Another aspect of the present invention is providing sets of molecular tags that may be separated into distinct bands or peaks by the separation technique employed after they are released from binding compounds. Molecular tags within a set may be chemically diverse; however, for convenience, sets of molecular tags are usually chemically related. For example, they may all be peptides, or they may consist of different combinations of the same basic building blocks or monomers, or they may be synthesized using the same basic scaffold with different substituent groups for imparting different separation characteristics, as described more fully below. The number of molecular tags in a plurality may vary depending on several factors including the mode of separation employed, the labels used on the molecular tags for detection, the sensitivity of the binding moieties, the efficiency with which the cleavable linkages are cleaved, and the like. In one aspect, the number of molecular tags in a plurality ranges from 2 to several tens, e.g. 30. In other aspects, the size of the plurality may be in the range of from 2 to 20, 2 to 10, 3 to 20, 3 to 10, 4 to 30, 4 to 10, 5 to 20,or 5 to 10.

Molecular Tags and Cleavable Linkages

In one embodiment, molecular tags are cleaved from a binding compound, or tagged probe, by reaction of a cleavable linkage with an active species, such as singlet oxygen, generated by a cleavage-inducing moiety, e.g. Singh et al, International patent publication WO 01/83502 and WO 02/95356.

An aspect of the invention includes providing mixtures of pluralities of different binding compounds, wherein each different binding compound has one or more molecular tags attached through cleavable linkages. The nature of the binding compound, cleavable linkage and molecular tag may vary widely. A binding compound may comprise an antibody binding composition, an antibody, a peptide, a peptide or non-peptide ligand for a cell surface receptor, a protein, an oligonucleotide, an oligonucleotide analog, such as a peptide nucleic acid, a lectin, or any other molecular entity that is capable of specific binding or complex formation with a membrane-associated analyte of interest. In one aspect, a binding compound, which can be represented by the formula below, comprises one or more molecular tags attached to an analyte-specific binding moiety.

$$B\text{-}(L\text{-}E)_k$$

wherein B is a binding moiety; L is a cleavable linkage; and E is a molecular tag. Preferably, in homogeneous assays for non-polynucleotide analytes, cleavable linkage, L, is an oxidation-labile linkage, and more preferably, it is a linkage that may be cleaved by singlet oxygen. The moiety "-(L-E)$_k$" indicates that a single binding compound may have multiple molecular tags attached via cleavable linkages. In one aspect, k is an integer greater than or equal to one, but in other embodiments, k may be greater than several hundred, e.g. 100 to 500, or k is greater than several hundred to as many as several thousand, e.g. 500 to 5000. Within a composition of the invention, usually each of the plurality of different types of binding compound has a different molecular tag, E. Cleavable linkages, e.g. oxidation-labile linkages, and molecular tags, E, are attached to B by way of conventional chemistries.

Preferably, B is an antibody binding composition. Such compositions are readily formed from a wide variety of commercially available antibodies, both monoclonal and polyclonal, specific for membrane-associated analytes. In particular, antibodies specific for epidermal growth factor receptors are disclosed in the following patents, which are incorporated by references: U.S. Pat. Nos. 5,677,171; 5,772,997; 5,968,511; 5,480,968; 5,811,098. U.S. Pat. No. 6,488,390, incorporated herein by reference, discloses antibodies specific for a G-protein coupled receptor, CCR4. U.S. Pat. No. 5,599,681, incorporated herein by reference, discloses antibodies specific for phosphorylation sites of proteins.

When L is oxidation labile, L is preferably a thioether or its selenium analog; or an olefin, which contains carbon-carbon double bonds, wherein cleavage of a double bond to an oxo group, releases the molecular tag, E. Illustrative thioether bonds are disclosed in Willner et al, U.S. Pat. No. 5,622,929 which is incorporated by reference. Illustrative olefms include vinyl sulfides, vinyl ethers, enamines, imines substituted at the carbon atoms with an α-methine (CH, a carbon atom having at least one hydrogen atom), where the vinyl group may be in a ring, the heteroatom may be in a ring, or substituted on the cyclic olefinic carbon atom, and there will be at least one and up to four heteroatoms bonded to the olefinic carbon atoms. The resulting dioxetane may decompose spontaneously, by heating above ambient temperature, usually below about 75° C., by reaction with acid or base, or by photo-activation in the absence or presence of a photosensitizer. Such reactions are described in the following exemplary references: Adam and Liu, J. Amer. Chem. Soc. 94, 1206–1209, 1972, Ando, et al., J. C. S. Chem. Comm. 1972, 477–8, Ando, et al., Tetrahedron 29, 1507–13, 1973, Ando, et al., J. Amer. Chem. Soc. 96, 6766–8, 1974, Ando and Migita, ibid. 97, 5028–9, 1975, Wasserman and Terao, Tetra. Lett. 21, 1735–38, 1975, Ando and Watanabe, ibid. 47, 4127–30, 1975, Zaklika, et al., Photochemistry and Photobiology 30, 3544, 1979, and Adam, et al., Tetra. Lett. 36, 7853–4, 1995. See also, U.S. Pat. No. 5,756,726.

The formation of dioxetanes is obtained by the reaction of singlet oxygen with an activated olefin substituted with an molecular tag at one carbon atom and the binding moiety at the other carbon atom of the olefin. See, for example, U.S. Pat. No. 5,807,675. These cleavable linkages may be depicted by the following formula:

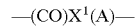
—W—(X)$_n$C$_\alpha$=C$_\beta$(y)(Z)— wherein:

W may be a bond, a heteroatom, e.g., O, S, N, P, M (intending a metal that forms a stable covalent bond), or a functionality, such as carbonyl, imino, etc., and may be bonded to X or C a at least one X will be aliphatic, aromatic, alicyclic or heterocyclic and bonded to C, (through a hetero atom, e.g., N, O, or S and the other X may be the same or different and may in addition be hydrogen, aliphatic, aromatic, alicyclic or heterocyclic, usually being aromatic or aromatic heterocyclic wherein one X may be taken together with Y to form a ring, usually a heterocyclic ring, with the carbon atoms to which they are attached, generally when other than hydrogen being from about 1 to 20, usually 1 to 12, more usually 1 to 8 carbon atoms and one X will have 0 to 6, usually 0 to 4 heteroatoms, while the other X will have at least one heteroatom and up to 6 heteroatoms, usually 1 to 4 heteroatoms;

Y will come within the definition of X, usually being bonded to C,6 through a heteroatom and as indicated may be taken together with X to form a heterocyclic ring;

Z will usually be aromatic, including heterocyclic aromatic, of from about 4 to 12, usually 4 to 10 carbon atoms and 0 to 4 heteroatoms, as described above, being bonded directly to C$_\beta$ or through a heteroatom, as described above;

n is 1 or 2, depending upon whether the molecular tag is bonded to C$_\alpha$ or X;

wherein one of Y and Z will have a functionality for binding to the binding moiety, or be bound to the binding moiety, e.g. by serving as, or including a linkage group, to a binding moiety, T.

Preferably, W, X, Y, and Z are selected so that upon cleavage molecular tag, E, is within the size limits described below.

Illustrative cleavable linkages include S(molecular tag)-3-thiolacrylic acid, N(molecular tag), N-methyl 4-amino-4-butenoic acid, 3-hydroxyacrolein, N-(4-carboxyphenyl)-2-(molecular tag)-imidazole, oxazole, and thiazole.

Also of interest are N-alkyl acridinyl derivatives, substituted at the 9 position with a divalent group of the formula:

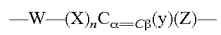
—(CO)X$^1$(A)— wherein:

X$^1$ is a heteroatom selected from the group consisting of O, S, N, and Se, usually one of the first three; and A is a chain of at least 2 carbon atoms and usually not more than 6 carbon atoms substituted with an molecular tag, where preferably the other valences of A are satisfied by hydrogen, although the chain may be substituted with other groups, such as alkyl, aryl, heterocyclic groups, etc., A generally being not more than 10 carbon atoms.

Also of interest are heterocyclic compounds, such as diheterocyclopentadienes, as exemplified by substituted imidazoles, thiazoles, oxazoles, etc., where the rings will usually be substituted with at least one aromatic group and in some instances hydrolysis will be necessary to release the molecular tag.

Also of interest are tellurium (Te) derivatives, where the Te is bonded to an ethylene group having a hydrogen atom )3 to the Te atom, wherein the ethylene group is part of an alicyclic or heterocyclic ring, that may have an oxo group, preferably fused to an aromatic ring and the other valence of the Te is bonded to the molecular tag. The rings may be coumarin, benzoxazine, tetralin, etc.

Several preferred cleavable linkages and their cleavage products are illustrated in FIGS. 3A–F. The thiazole cleavable linkage, "—CH$_2$-thiazole-(CH2)$_n$—C(=O)—NH—protein," shown in FIG. 3A, results in an molecular tag with the moiety "—CH$_2$—C(=O)—NH—CHO." Preferably, n is in the range of from 1 to 12, and more preferably, from 1 to 6. The oxazole cleavable linkage, "—CH$_2$—oxazole—

Figure 3A:
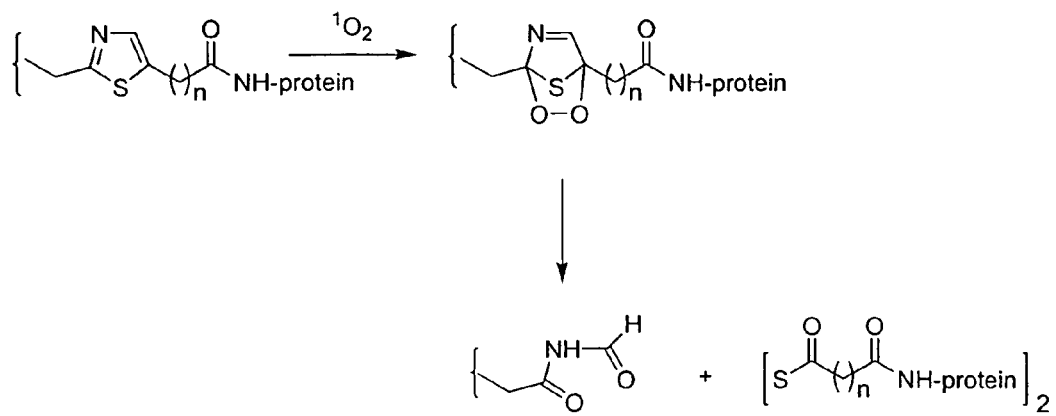
FIGS. 3A–3F illustrate oxidation-labile linkages and their respective cleavage reactions mediated by singlet oxygen.
Figure 3B:
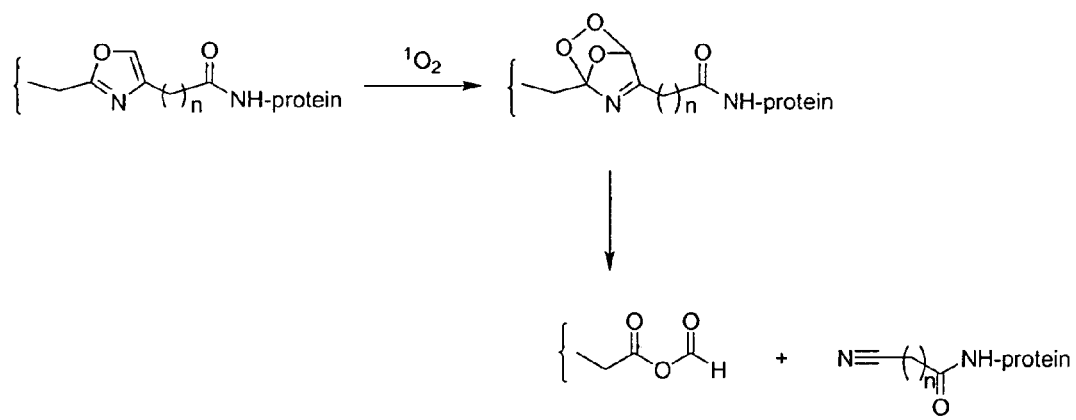
Figure 3C:
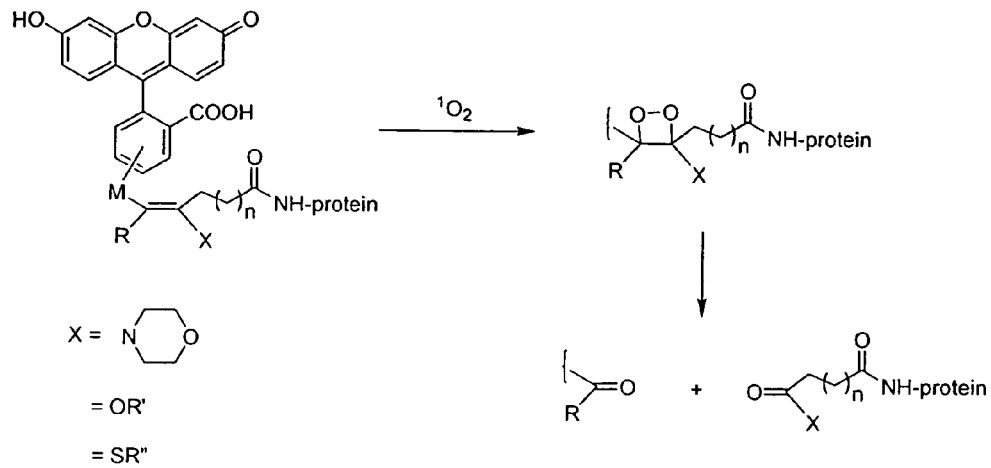
Figure 3D:
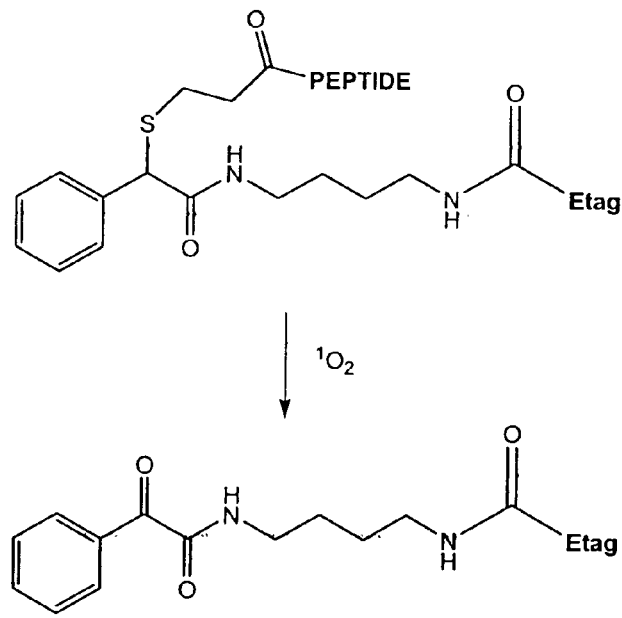
Figure 3E:
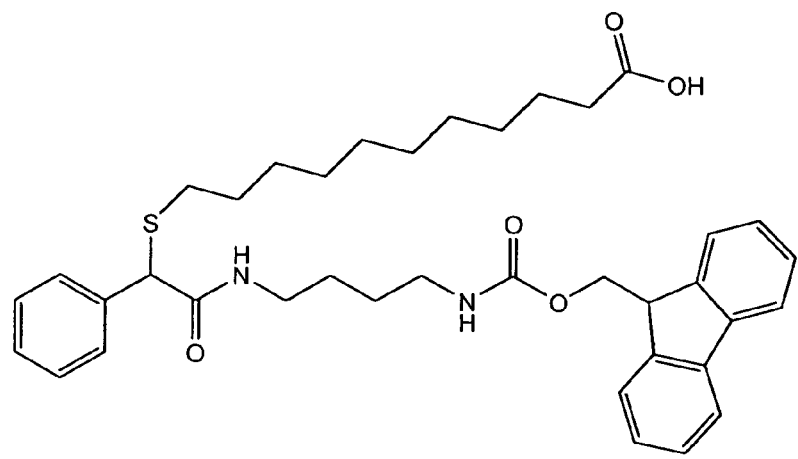
Figure 3F:
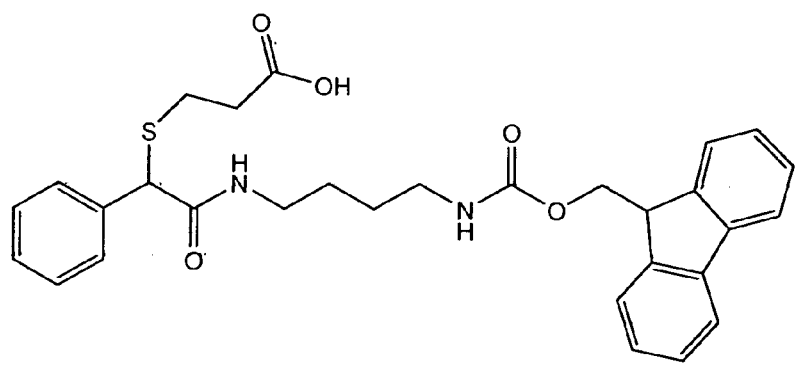

(CH2)$_n$—C(═O)—NH-protein," shown in FIG. 3B, results in an molecular tag with the moiety "—CH$_2$—C(═O)O—CHO." An olefm cleavable linkage (FIG. 3C) is shown in connection with the binding compound embodiment "B—L—M—D," described above and with D being a fluorescein dye. The olefin cleavable linkage may be employed in other embodiments also. Cleavage of the illustrated olefm linkage results in an molecular tag of the form: "R—(C═O)—M—D," where "R" may be any substituent within the general description of the molecular tags, E, provided above. Preferably, R is an electron-donating group, e.g. Ulhman et al, U.S. Pat. No. 6,251,581; Smith and March, March's Advanced Organic Chemistry: Reactions, Mechanisms, and Structure, 5b Edition (Wiley-Interscience, New York, 2001); and the like. More preferably, R is an electron-donating group having from 1–8 carbon atoms and from 0 to 4 heteroatoms selected from the group consisting of O, S, and N. In further preference, R is —N(Q)$_2$, —OQ, p-[C$_6$H$_4$N(Q)$_2$]furanyl, n-alkylpyrrolyl, 2-indolyl, or the like, where Q is alkyl or aryl. In further reference to the olefin cleavable linkage of FIG. 3C, substituents "X" and "R" are equivalent to substituents "X" and "Y" of the above formula describing cleavable linkage, L. In particular, X in FIG. 3C is preferably morpholino, —OR', or —SR", where R' and R" are aliphatic, aromatic, alicyclic or heterocyclic having from 1 to 8 carbon atoms and 0 to 4 heteroatoms selected from the group consisting of O, S. and N. A preferred thioether cleavable linkage is illustrated in FIG. 3D having the form "—(CH$_2$)$_2$—S—CH(C$_6$H$_5$)C(═O)NH—(CH$_2$)$_n$—NH—," wherein n is from 2 to 12, and more preferably, in the range of from 2 to 6. Thioether cleavable linkages of the type shown in FIG. 3D may be attached to binding moieties, T, and molecular tags, E, by way of precursor compounds shown in FIGS. 3E and 3F. To attach to an amino group of a binding moiety, T, the terminal hydroxyl is converted to an NHS ester by conventional chemistry. After reaction with the amino group and attachment, the Fmoc protection group is removed to produce a free amine which is then reacted with an NHS ester of the molecular tag.

Molecular tag, E, in the present invention may comprise an electrophoric tag as described in the following references when separation of pluralities of molecular tags are carried out by gas chromatography or mass spectrometry: Zhang et al, Bioconjugate Chem., 13: 1002–1012 (2002); Giese, Anal. Chem., 2: 165–168 (1983); and U.S. Pat. Nos. 4,650,750; 5,360,819; 5,516,931; 5,602,273; and the like.

Molecular tag, E, is preferably a water-soluble organic compound that is stable with respect to the active species, especially singlet oxygen, and that includes a detection or reporter group. Otherwise, E may vary widely in size and structure. In one aspect, E has a molecular weight in the range of from about 50 to about 2500 daltons, more preferably, from about 50 to about 1500 daltons. Preferred structures of E are described more fully below. E may comprise a detection group for generating an electrochemical, fluorescent, or chromogenic signal. In embodiments employing detection by mass, E may not have a separate moiety for detection purposes. Preferably, the detection group generates a fluorescent signal.

Molecular tags within a plurality are selected so that each has a unique separation characteristic and/or a unique optical property with respect to the other members of the same plurality. In one aspect, the chromatographic or electrophoretic separation characteristic is retention time under set of standard separation conditions conventional in the art, e.g. voltage, column pressure, column type, mobile phase, electrophoretic separation medium, or the like. In another aspect, the optical property is a fluorescence property, such as emission spectrum, fluorescence lifetime, fluorescence intensity at a given wavelength or band of wavelengths, or the like. Preferably, the fluorescence property is fluorescence intensity. For example, each molecular tag of a plurality may have the same fluorescent emission properties, but each will differ from one another by virtue of a unique retention time. On the other hand, or two or more of the molecular tags of a plurality may have identical retention times, but they will have unique fluorescent properties, e.g. spectrally resolvable emission spectra, so that all the members of the plurality are distinguishable by the combination of molecular separation and fluorescence measurement.

Preferably, released molecular tags are detected by electrophoretic separation and the fluorescence of a detection group. In such embodiments, molecular tags having substantially identical fluorescence properties have different electrophoretic mobilities so that distinct peaks in an electropherogram are formed under separation conditions. Preferably, pluralities of molecular tags of the invention are separated by conventional capillary electrophoresis apparatus, either in the presence or absence of a conventional sieving matrix. Exemplary capillary electrophoresis apparatus include Applied Biosystems (Foster City, Calif.) models 310, 3100 and 3700; Beckman (Fullerton, Calif.) model P/ACE MDQ; Amersham Biosciences (Sunnyvale, Calif.) MegaBACE 1000 or 4000; SpectruMedix genetic analysis system; and the like. Electrophoretic mobility is proportional to $q/M^{2/3}$, where q is the charge on the molecule and M is the mass of the molecule. Desirably, the difference in mobility under the conditions of the determination between the closest electrophoretic labels will be at least about 0.001, usually 0.002, more usually at least about 0.01, and may be 0.02 or more. Preferably, in such conventional apparatus, the electrophoretic mobilities of molecular tags of a plurality differ by at least one percent, and more preferably, by at least a percentage in the range of from 1 to 10 percent.

Figure 4A:
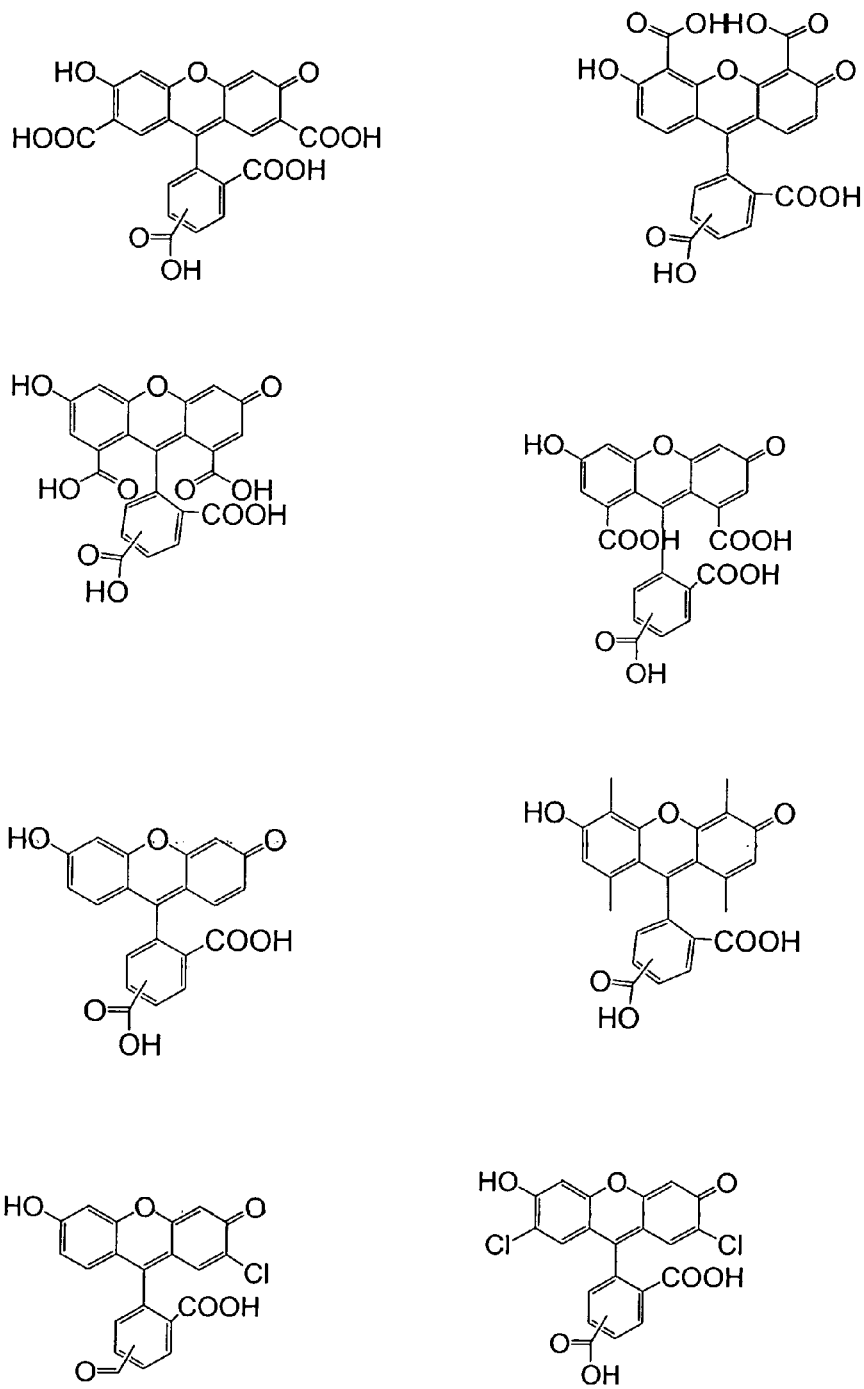
FIGS. 4A–4B illustrate fluorescein derivatives that may be used in constructing molecular tags of the invention.
Figure 4B:
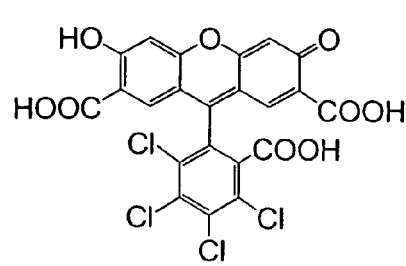
Figure 4B:
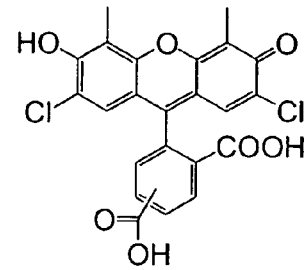
Figure 4B:
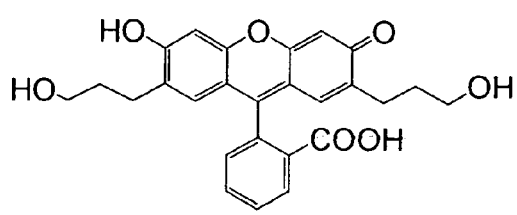
Figure 4B:
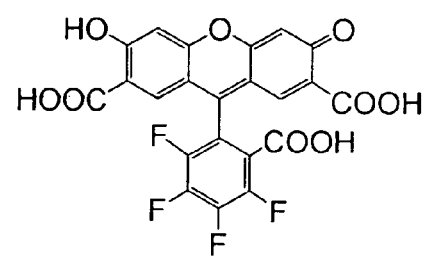
Figure 4B:
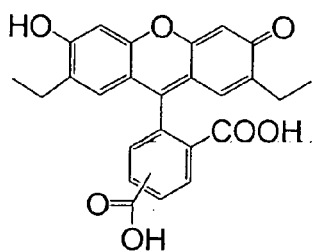
Figure 4B:
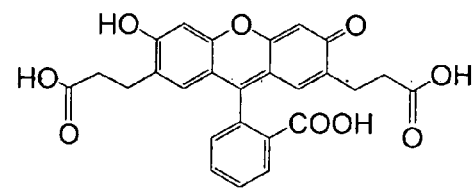
Figure 4B:
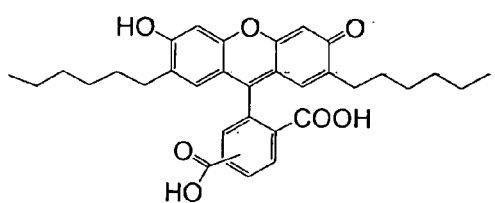
Figure 4B:
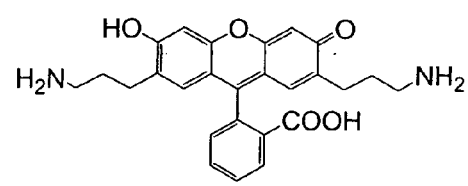

In one aspect, molecular tag, E, is (M, D), where M is a mobility-modifying moiety and D is a detection moiety. The notation "(M, D)" is used to indicate that the ordering of the M and D moieties may be such that either moiety can be adjacent to the cleavable linkage, L. That is, "B-L-(M, D)" designates binding compound of either of two forms: "B-L-M-D" or "B-L-D-M." Detection moiety, D, may be a fluorescent label or dye, a chromogenic label or dye, an electrochemical label, or the like. Preferably, D is a fluorescent dye. Exemplary fluorescent dyes for use with the invention include water-soluble rhodamnine dyes, fluoresceins, 4,7-dichlorofluoresceins, benzoxanthene dyes, and energy transfer dyes, disclosed in the following references: Handbook of Molecular Probes and Research Reagents, 8$^{th}$ ed., (Molecular Probes, Eugene, 2002); Lee et al, U.S. Pat. No. 6,191,278; Lee et al, U.S. Pat. No. 6,372,907; Menchen et al, U.S. Pat. No. 6,096,723; Lee et al, U.S. Pat. No. 5,945,526; Lee et al, Nucleic Acids Research, 25: 2816–2822 (1997); Hobb, Jr., U.S. Pat. No. 4,997,928; Khanna et al., U.S. Pat. No. 4,318,846; Reynolds, U.S. Pat. No. 3,932,415; Eckert et al, U.S. Pat. No. 2,153,059; Eckert et al, U.S. Pat. No. 2,242, 572; Taing et al, International patent publication WO 02/30944; and the like. Further specific exemplary fluorescent dyes include 5- and 6-carboxyrhodamine 6G; 5- and 6-carboxy-X-rhodamine, 5- and 6-carboxytetramethyl-rhodamine, 5- and 6-carboxyfluorescein, 5- and 6-carboxy-4,7-dichlorofluor 2',7'-irethoxy-5- and 6-carboxy4,7-dichlorofluorescein, 2',7'-dimethoxy-4',5'-dichloro-6-carboxy4,7-dichlorofluorescein, 1',2',7',8'-dibenzo-5- and 6-carboxy4,7- dichlorofluorescein, 1',2',7',8'-dibenzo4',5'-dichloro-5- and 6-carboxy-4,7-dichlorofluorescein, 2',7'-d 6-carboxy4,7-dichlorofluorescein, and 2',4',5',7'-tetrachloro-5- and 6-carboxy4,7-dichlorofluor Most preferably, D is a fluorescein or a fluorescein derivative. Exemplary fluorescein dyes that may be used with the invention are illustrated in FIGS. 4A–4B.

The size and composition of mobility-modifying moiety, M, can vary from a bond to about 100 atoms in a chain, usually not more than about 60 atoms, more usually not more than about 30 atoms, where the atoms are carbon, oxygen, nitrogen, phosphorous, boron and sulfur. Generally, when other than a bond, the mobility-modifing moiety has from about 0 to about 40, more usually from about 0 to about 30 heteroatoms, which in addition to the heteroatoms indicated above may include halogen or other heteroatom. The total number of atoms other than hydrogen is generally fewer than about 200 atoms, usually fewer than about 100 atoms. Where acid groups are present, depending upon the pH of the medium in which the mobility-modifying moiety is present, various cations may be associated with the acid group. The acids may be organic or inorganic, including carboxyl, thionocarboxyl, thiocarboxyl, hydroxamic, phosphate, phosphite, phosphonate, phosphinate, sulfonate, sulfinate, boronic, nitric, nitrous, etc. For positive charges, substituents include amino (includes ammonium), phosphonium, sulfonium, oxonium, etc., where substituents are generally aliphatic of from about 1–6 carbon atoms, the total number of carbon atoms per heteroatom, usually be less than about 12, usually less than about 9. The side chains include amines, ammonium salts, hydroxyl groups, including phenolic groups, carboxyl groups, esters, amides, phosphates, heterocycles. M may be a homo-oligomer or a hetero-oligomer, having different monomers of the same or different chemical characteristics, e.g., nucleotides and amino acids.

In another aspect, (M,D) moieties are constructed from chemical scaffolds used in the generation of combinatorial libraries. For example, the following references describe scaffold compound useful in generating diverse mobility modifying moieties: peptoids (PCT Publication No WO 91/19735, Dec. 26, 1991), encoded peptides (PCT Publication WO 93/20242, Oct. 14 1993), random bio-oligomers (PCT Publication WO 92/00091, Jan. 9, 1992), benzodiazepines (U.S. Pat. No. 5,288,514), diversomeres such as hydantoins, benzodiazepines and dipeptides (Hobbs DeWitt, S. et al., Proc. Nat. Acad. Sci. U.S.A. 90: 6909–6913 (1993), vinylogous polypeptides (Hagihara et aL J.Amer. Chem. Soc. 114: 6568 (1992)), nonpeptidal peptidomimetics with a Beta-D-Glucose scaffolding (Hirschmann, R. et al., J.Amer. Chem. Soc. 114: 9217–9218 (1992)), analogous organic syntheses of small compound libraries (Chen, C. et al. J.Amer. Chem. Soc. 116: 2661(1994)), oligocarbamates (Cho, C. Y. et aL Science 261: 1303(1993)), peptidyl phosphonates (Campbell, D. A. et al., J. Org. Chem. 59:658 (1994)); Cheng et al, U.S. Pat. No. 6,245,937; Heizmann et al, "Xanthines as a scaffold for molecular diversity," Mol. Divers. 2: 171–174 (1997); Pavia et al, Bioorg. Med. Chem., 4: 659–666 (1996); Ostresh et al, U.S. Pat. No. 5,856,107; Gordon, E. M. et al., J. Med. Chem. 37: 1385 (1994); and the like. Preferably, in this aspect, D is a substituent on a scaffold and M is the rest of the scaffold.

M may also comprise polymer chains prepared by known polymer subunit synthesis methods. Methods of forming selected-length polyethylene oxide-containing chains are well known, e.g. Grossman et al, U.S. Pat. No. 5,777,096. It can be appreciated that these methods, which involve coupling of defined-size, multi-subunit polymer units to one another, directly or via linking groups, are applicable to a wide variety of polymers, such as polyethers (e.g., polyethylene oxide and polypropylene oxide), polyesters (e.g., polyglycolic acid, polylactic acid), polypeptides, oligosaccharides, polyurethanes, polyamides, polysulfonamides, polysulfoxides, polyphosphonates, and block copolymers thereof, including polymers composed of units of multiple subunits linked by charged or uncharged linking groups. In addition to homopolymers, the polymer chains used in accordance with the invention include selected-length copolymers, e.g., copolymers of polyethylene oxide units alternating with polypropylene units. As another example, polypeptides of selected lengths and amino acid composition (ie., containing naturally occurring or man-made amino acid residues), as homopolymers or mixed polymers.

In another aspect, after release, molecular tag, E, is defined by the formula:

wherein:

A is —C(═O)R, where R is aliphatic, aromatic, alicyclic or heterocyclic having from 1 to 8 carbon atoms and 0 to 4 heteroatoms selected from the group consisting of O, S. and N; —CH$_2$— C(═O)—NH—CHO; —SO$_2$H; —CH$_2$—C(═O)O—CHO; —C(═O)NH—(CH$_2$)$_n$—NH—C(═O)C(═O)—where n is in the range of from 2 to 12;

D is a detection group, preferably a fluorescent dye; and

M is as described above, with the proviso that the total molecular weight of A-M-D be within the range of from about 100 to about 2500 daltons.

In another aspect, D is a fluorescein and the total molecular weight of A-M-D is in the range of from about 100 to about 1500 daltons.

In another aspect, M may be synthesized from smaller molecules that have functional groups that provide for linking of the molecules to one another, usually in a linear chain. Such functional groups include carboxylic acids, amines, and hydroxy- or thiol- groups. In accordance with the present invention the charge-imparting moiety may have one or more side groups pending from the core chain. The side groups have a functionality to provide for linking to a label or to another molecule of the charge-imparting moiety. Common functionalities resulting from the reaction of the functional groups employed are exemplified by forming a covalent bond between the molecules to be conjugated. Such functionalities are disulfide, amide, thioamide, dithiol, ether, urea, thiourea, guanidine, azo, thioether, carboxylate and esters and amides containing sulfur and phosphorus such as, e.g., sulfonate, phosphate esters, sulfonamides, thioesters, etc., and the like.

Attaching Molecular Tags to Binding Moieties

Extensive guidance can be found in the literature for covalently linking molecular tags to binding compounds, such as antibodies, e.g. Hermanson, Bioconjugate Techniques, (Academic Press, New York, 1996), and the like. In one aspect of the invention, one or more molecular tags are attached directly or indirectly to common reactive groups on a binding compound. Common reactive groups include amine, thiol, carboxylate, hydroxyl, aldehyde, ketone, and the like, and may be coupled to molecular tags by commercially available cross-linking agents, e.g. Hermanson (cited above); Haugland, Handbook of Fluorescent Probes and Research Products, Ninth Edition (Molecular Probes, Eugene, Oreg., 2002). In one embodiment, an NHS-ester of a molecular tag is reacted with a free amine on the binding compound.

In a preferred embodiment illustrated in FIG. 1C, binding compounds comprise a biotinylated antibody (140) as a binding moiety. Molecular tags (144) are attached to binding moiety (140) by way of avidin or streptavidin bridge (142). Preferably, in operation, binding moiety (140) is first reacted with membrane-bound analytes, after which avidin or streptavidin is added (146) to form complex (148). To complexes (148) are added (150) biotinylated molecular tags to form binding compound (152).

Once each of the binding compounds is separately derivatized by a different molecular tag, it is pooled with other binding compounds to form a plurality of binding compounds. Usually, each different kind of binding compound is present in a composition in the same proportion; however, proportions may be varied as a design choice so that one or a subset of particular binding compounds are present in greater or lower proportion depending on the desirability or requirements for a particular embodiment or assay. Factors that may affect such design choices include, but are not limited to, antibody affinity and avidity for a particular target, relative prevalence of a target, fluorescent characteristics of a detection moiety of a molecular tag, and the like.

Cleavage-Inducing Moiety Producing Active Species

A cleavage-inducing moiety, or cleaving agent, is a group that produces an active species that is capable of cleaving a cleavable linkage, preferably by oxidation. Preferably, the active species is a chemical species that exhibits short-lived activity so that its cleavage-inducing effects are only in the proximity of the site of its generation. Either the active species is inherently short lived, so that it will not create significant background because beyond the proximity of its creation, or a scavenger is employed that efficiently scavenges the active species, so that it is not available to react with cleavable linkages beyond a short distance from the site of its generation. Illustrative active species include singlet oxygen, hydrogen peroxide, NADH, and hydroxyl radicals, phenoxy radical, superoxide, and the like. Illustrative quenchers for active species that cause oxidation include polyenes, carotenoids, vitamin E, vitamin C, amino acid-pyrrole N-conjugates of tyrosine, histidine, and glutathione, and the like, e.g. Beutner et al, Meth. Enzymol., 319: 226–241 (2000).

An important consideration for the cleavage-inducing moiety and the cleavable linkage is that they not be so far removed from one another when bound to a target protein that the active species generated by the sensitizer diffises and loses its activity before it can interact with the cleavable linkage. Accordingly, a cleavable linkage preferably are within 1000 nm, preferably 20–200 nm of a bound cleavage-inducing moiety. This effective range of a cleavage-inducing moiety is referred to herein as its "effective proximity."

Generators of active species include enzymes, such as oxidases, such as glucose oxidase, xanthene oxidase, D-amino acid oxidase, NADH-FMN oxidoreductase, galactose oxidase, glyceryl phosphate oxidase, sarcosine oxidase, choline oxidase and alcohol oxidase, that produce hydrogen peroxide, horse radish peroxidase, that produces hydroxyl radical, various dehydrogenases that produce NADH or NADPH, urease that produces ammonia to create a high local pH.

A sensitizer is a compound that can be induced to generate a reactive intermediate, or species, usually singlet oxygen. Preferably, a sensitizer used in accordance with the invention is a photosensitizer. Other sensitizers included within the scope of the invention are compounds that on excitation by heat, light, ionizing radiation, or chemical activation will release a molecule of singlet oxygen. The best known members of this class of compounds include the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen. Further sensitizers are disclosed in the following references: Di Mascio et al, FEBS Lett., 355: 287 (1994)(peroxidases and oxygenases); Kanofsky, J.Biol. Chem. 258: 5991–5993 (1983)(lactoperoxidase); Pierlot et al, Meth. Enzymol., 319: 3–20 (2000)(thermal lysis of endoperoxides); and the like.

Attachment of a binding agent to the cleavage-inducing moiety may be direct or indirect, covalent or non-covalent and can be accomplished by well-known techniques, commonly available in the literature. See, for example, "Immobilized Enzymes," Ichiro Chibata, Halsted Press, New York (1978); Cuatrecasas, J. Biol. Chem., 245:3059 (1970). A wide variety of functional groups are available or can be incorporated. Functional groups include carboxylic acids, aldehydes, amino groups, cyano groups, ethylene groups, hydroxyl groups, mercapto groups, and the like. The manner of linking a wide variety of compounds is well known and is amply illustrated in the literature (see above). The length of a linking group to a binding agent may vary widely, depending upon the nature of the compound being linked, the effect of the distance on the specific binding properties and the like.

It may be desirable to have multiple cleavage-inducing moieties attached to a binding agent to increase, for example, the number of active species generated. This can be accomplished with a polyfunctional material, normally polymeric, having a plurality of functional groups, e.g., hydroxy, amino, mercapto, carboxy, ethylenic, aldehyde, etc., as sites for linking. Alternatively a support may be used. The support can have any of a number of shapes, such as particle including bead, film, membrane, tube, well, strip, rod, and the like. For supports in which photosensitizer is incorporated, the surface of the support is, preferably, hydrophilic or capable of being rendered hydrophilic and the body of the support is, preferably, hydrophobic. The support may be suspendable in the medium in which it is employed. Examples of suspendable supports, by way of illustration and not limitation, are polymeric materials such as latex, lipid bilayers, oil droplets, cells and hydrogels. Other support compositions include glass, metals, polymers, such as nitrocellulose, cellulose acetate, poly(vinyl chloride), polyacrylamide, polyacrylate, polyethylene, polypropylene, poly (4-methylbutene), polystyrene, polymethacrylate, poly(ethylene terephthalate), nylon, poly(vinyl butyrate), etc.; either used by themselves or in conjunction with other materials. Attachment of binding agents to the support may be direct or indirect, covalent or non-covalent and can be accomplished by well-known techniques, commonly available in the literature as discussed above. See, for example, "Immobilized Enzymes," Ichiro Chibata, supra. The surface of the support will usually be polyfunctional or be capable of being polyfunctionalized or be capable of binding to a target-binding moiety, or the like, through covalent or specific or non-specific non-covalent interactions.

The cleavage-inducing moiety may be associated with the support by being covalently or non-covalently attached to the surface of the support or incorporated into the body of the support. Linking to the surface may be accomplished as discussed above. The cleavage-inducing moiety may be incorporated into the body of the support either during or after the preparation of the support. In general, the cleavage-inducing moiety is associated with the support in an amount necessary to achieve the necessary amount of active species. Generally, the amount of cleavage-inducing moiety is determined empirically.

Photosensitizers as Cleavage-Inducing Moieties

As mentioned above, the preferred cleavage-inducing moiety in accordance with the present invention is a photosensitizer that produces singlet oxygen. As used herein, "photosensitizer" refers to a light-adsorbing molecule that when activated by light converts molecular oxygen into singlet oxygen. Photosensitizers may be attached directly or indirectly, via covalent or non-covalent linkages, to the binding agent of a class-specific reagent. Guidance for constructiing of such compositions, particularly for antibodies as binding agents, available in the literature, e.g. in the fields of photodynamic therapy, immunodiagnostics, and the like. The following are exemplary references: Ulhman, et al., Proc. Natl. Acad. Sci. USA 91, 5426–5430 (1994); Strong et al, Ann. New York Acad. Sci., 745: 297–320 (1994); Yarmush et al, Crit. Rev. Therapeutic Drug Carrier Syst., 10: 197–252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516, 636; and the like.

Likewise, there is guidance in the literature regarding the properties and selection of photosensitizers suitable for use in the present invention. The following are exemplary references: Wasserman and R.W. Murray. Singlet Oxygen. (Academic Press, New York, 1979); Baumstark, Singlet Oxygen, Vol. 2 (CRC Press Inc., Boca Raton, Fla. 1983); and Turro, Modem Molecular Photochemistry (University Science Books, 1991).

The photosensitizers are sensitizers for generation of singlet oxygen by excitation with light. The photosensitizers include dyes and aromatic compounds, and are usually compounds comprised of covalently bonded atoms, usually with multiple conjugated double or triple bonds. The compounds typically absorb light in the wavelength range of about 200 to about 1,100 nm, usually, about 300 to about 1,000 nm, preferably, about 450 to about 950 nm, with an extinction coefficient at its absorbance maximum greater than about 500 $M^{-1}$ $cm^{-1}$, preferably, about 5,000 $M^{-1}$ $cm^{-1}$, more preferably, about 50,000 $M^{-1}$ cmi', at the excitation wavelength. The lifetime of an excited state produced following absorption of light in the absence of oxygen will usually be at least about 100 nanoseconds, preferably, at least about 1 millisecond. In general, the lifetime must be sufficiently long to permit cleavage of a linkage in a reagent in accordance with the present invention. Such a reagent is normally present at concentrations as discussed below. The photosensitizer excited state usually has a different spin quantum number (S) than its ground state and is usually a triplet (S=1) when the ground state, as is usually the case, is a singlet (S=0). Preferably, the photosensitizer has a high intersystem crossing yield. That is, photoexcitation of a photosensitizer usually produces a triplet state with an efficiency of at least about 10%, desirably at least about 40%, preferably greater than about 80%.

Photosensitizers chosen are relatively photostable and, preferably, do not react efficiently with singlet oxygen. Several structural features are present in most useful photosensitizers. Most photosensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they may have extended aromatic structures.

A large variety of light sources are available to photoactivate photosensitizers to generate singlet oxygen. Both polychromatic and monchromatic sources may be used as long as the source is sufficiently intense to produce enough singlet oxygen in a practical time duration. The length of the irradiation is dependent on the nature of the photosensitizer, the nature of the cleavable linkage, the power of the source of irradiation, and its distance from the sample, and so forth. In general, the period for irradiation may be less than about a microsecond to as long as about 10 minutes, usually in the range of about one millisecond to about 60 seconds. The intensity and length of irradiation should be sufficient to excite at least about 0.1% of the photosensitizer molecules, usually at least about 30% of the photosensitizer molecules and preferably, substantially all of the photosensitizer molecules. Exemplary light sources include, by way of illustration and not limitation, lasers such as, e.g., helium-neon lasers, argon lasers, YAG lasers, He/Cd lasers, and ruby lasers; photodiodes; mercury, sodium and xenon vapor lamps; incandescent lamps such as, e.g., tungsten and tungsten/halogen; flashlamps; and the like.

Examples of photosensitizers that may be utilized in the present invention are those that have the above properties and are enumerated in the following references: Turro, Modem Molecular Photochemistry (cited above); Singh and Ullman, U.S. Pat. No. 5,536,834; Li et al, U.S. patent 5,763,602; Ullman, et al., Proc. Natl. Acad. Sci. USA 91, 5426–5430 (1994); Strong et al, Ann. New York Acad. Sci., 745: 297–320 (1994); Martin et al, Methods Enzymol., 186: 635–645 (1990);Yarmush et al, Crit. Rev. Therapeutic Drug Carrier Syst., 10: 197–252 (1993); Pease et al, U.S. Pat. No. 5,709,994; Ullman et al, U.S. Pat. No. 5,340,716; Ullman et al, U.S. Pat. No. 6,251,581; McCapra, U.S. Pat. No. 5,516, 636; Wohrle, Chimia,45: 307–310 (1991); Thetford, European patent publ. 0484027; Sessler et al, SPIE, 1426: 318–329 (1991); Madison et al, Brain Research, 522: 90–98 (1990); Polo et al, Inorganica Chimica Acta, 192: 1–3 (1992); Demas et al, J. Macromol. Sci., A25: 1189–1214 (1988); and the like. Exemplary photosensitizers are listed in Table 1a.

TABLE 1a

Exemplary Photosensitizers

| | |
|---|---|
| Hypocrellin A | Tetraphenylporphyrin |
| Hypocrellin B | Halogenated derivatives of rhodamine dyes |
| Hypericin | metallo-Porphyrins |
| Halogenated derivatives of fluorescein dyes | Phthalocyanines |
| Rose bengal | Naphthalocyanines |
| Merocyanine 540 | Texaphyrin-type macrocycles |
| Methylene blue | Hematophorphyrin |
| 9-Thioxanthone | 9,10-Dibromoanthracene |
| Chlorophylls | Benzophenone |
| Phenaleone | Chlorine 6 |
| Protoporphyrin | Perylene |
| Benzoporphryin A monacid | Benzoporphryin B monacid |

In certain embodiments the photosensitizer moiety comprises a support, as discussed above with respect to the cleavage-inducing moiety. The photosensitizer may be associated with the support by being covalently or non-covalently attached to the surface of the support or incorporated into the body of the support as discussed above. In general, the photosensitizer is associated with the support in an amount necessary to achieve the necessary amount of singlet oxygen. Generally, the amount of photosensitizer is determined empirically. Photosensitizers used as the photosensitizer are preferably relatively non-polar to assure dissolution into a lipophilic member when the photosensitizer is incorporated in, for example, a latex particle to form photosensitizer beads, e.g. as disclosed by Pease et al., U.S. Pat. No. 5,709,994. For example, the photosensitizer rose bengal is covalently attached to 0.5 micron latex beads by means of chloromethyl groups on the latex to provide an ester linking group, as described in J. Amer. Chem. Soc., 97: 3741 (1975).

In one aspect of the invention, a class-specific reagent comprises a first binding agent that is an antibody and a cleavage-inducing moiety that is a photosensitizer, such that the photosensitizer is covalently linked to the antibody, e.g. using well know techniques as disclosed in Strong et al (cited above); Yarmush et al (cited above); or the like. Alternatively, a class-specific reagent comprises a solid phase support, e.g. a bead, to which a photosensitizer is covalently or non-covalently attached and an antibody is attached, preferably convalently, either directly or by way of a functionalized polymer, such as amino-dextran, or the like.

Exemplary Cell Surface Molecules

Membrane-associated analytes include cell surface molecules that form dimeric or oligomeric complexes Cell surface receptors involved in signal transduction are of particular interest, including, but not limited to, enzyme-associated receptors and G-protein coupled receptors. Dimers or oligomers may comprise different cell surface receptors, that is, cell surface receptors that have different molecular structures, e.g. different primary amino acid sequences. As used herein, the term "receptor type" in reference to a dimer or an oligomer means one of a plurality of different cell surface molecules that participate in the formation of the dimer or oligomer. For example, a heterodimer, such as a Her2–Her3 heterodimer, consists of two different receptor types (Her2 and Her3) and a homodimer, such as a Her1-Her1 homodimer, consists of a single receptor type (Her1).

All enzyme-associated receptors are considlered within the scope of the present invention as subunits within a possible oligomeric cell surface complex. Enzyme-associated receptors of interest include several types having intrinsic enzymatic activities, including those with tyrosine kinase activity, tyrosine phosphatase activity, guanylate cyclase activity, and serine/threonine kinase activity. Additional enzyme-associated receptors of interest form protein-protein complexes with intracellular tyrosine kinases. Examples of tyrosine kinase-associated receptors include, but are not limited to, the Her receptor family, insulin receptor, IGF-1 receptor, PDGF receptors, FGF receptors, VEGF receptor, HGF and SC receptors, the neurotrophin receptor family, and NGF receptor. Examples of tyrosine phosphatase-associated receptors include, e.g., CD45 protein. Examples of guanylate cyclase-associated receptors include, e.g., the natriuretic peptide receptors. Examples of serine/threonine kinase -associated receptors include, e.g., activin receptor and transforming growth factor beta (TGF-β) receptors.

All GPCRs are considered within the scope of the present invention as subunits within a possible oligomeric cell surface complex. G-protein coupled receptors (GPCRs) of interest include those that modulate adenylate cyclase activity to generate cAMP as a second messenger, including, e.g., hormone receptors, adrenergic receptors, and odorant receptors, 2) those that activate phospholipase-Cγ (PLC-γ), and 3) photoreceptors. Families of GPCRs that may be studied using the methods of the present invention include, e.g., the Class A receptors (rhodopsin-like), including the acetylcholine, angiotensin, opiate, somatostatin, dopamine, and bradykinin receptors, the Class C receptors, including metabotropic glutamate, $Ca^{2+}$-sensing, and GABAb receptors, cAMP-coupled receptors, as well as many others. Examples of GPCR receptors that are known to form oligomers include, e.g., the muscarinic m3 receptor, angiotensin ATl receptor, GABAB, Membranes and Cells The membranes for use in the practice of the invention can be obtained from cells, such as a cellular membrane, nuclear membrane, mitochondrial membrane, or other intracellular membrane, or can be artificially created, as exemplified by micelles and liposomes. The cell(s) used in the methods described herein can be of any origin, including from prokaryotes, eukaryotes, or archeons, but preferably contain membranes that are lipophilic. The cell(s) may be living or dead. If obtained from a multicellular organism, the cell may be of any cell type. Thus, the cell(s) may be a cultured cell line or a primary isolate, the cell(s) may be mammalian, amphibian, reptilian, plant, yeast, bacterium, spirochetes, or protozoan. The cell(s) may be, for example, human, murine, rat, hamster, chicken, quail, goat or dog. The cell may be a norrnal cell, a mutated cell, a genetically manipulated cell, a tumor cell, hybridomas that are positive for secretion of selected antibodies, and the like. Of particular interest are membranes obtained from the type of cell that differentially expresses (over-expresses or under-expresses) a disease-causing gene. As is apparent to one skilled in the art, various cell lines, such as CHO, for example, may be obtained from public or private repositories. T he largest depository agent is American Type Culture Collection (http://www.atcc.org), which offers a diverse collection of well-characterized cell lines derived from a vast number of organisms and tissue samples.

Exemplary cell types from multicellular organisms include acidophils, acinar cells, pinealocytes, adipocytes, ameloblasts, astrocytes, basal (stem) cells, basophils, hepatocytes, neurons, bulging surface cells, C cells, cardiac muscle cells, centroacinar cells, chief cells, chondrocytes, Clara cells, columnar epithelial cells, corpus luteal cells, decidual cells, dendrites, endrocrine cells, endothelial cells, enteroendocrine cells, eosinophils, erythrocytes, extraglomerular mesangial cells, fetal fibroblasts, fetal red blood cells, fibroblasts, follicular cells, ganglion cells, giant Betz cells, goblet cells, hair cells, inner hair cells, type I hair cells, hepatocytes, endothelial cells, Leydig cells, lipocytes, liver parenchymal cells, lymphocytes, lysozyme-secreting cells, macrophages, mast cells, megakaryocytes, melanocytes, mesangial cells, monocytes, myoepithelial cells, myoid cells, neck mucous cells, nerve cells, neutrophils, oligodendrocytes, oocytes, osteoblasts, osteochondroclasts, osteoclasts, osteocytes, pillar cells, sulcal cells, parathyroid cells, parietal cells, pepsinogen-secreting cells, pericytes, pinealocytes, pituicytes, plasma cells, platelets, podocytes, spermatocytes, Purkinje cells, pyramidal cells, red blood cells, reticulocytes, Schwann cells, Sertoli cells, columnar cells, skeletal muscle cells, smooth muscle cells, somatostatin cells, enteroendocrine cells, spermatids, spermatogonias, spermatozoas, stellate cells, supporting Deiter cells, support Hansen cells, surface cells, surface epithelial cells, surface mucous cells, sweat gland cells, T lymphocytes, theca lutein cells, thymocytes, thymus epithelial cell, thyroid cells, transitional epithelial cells, type I pneumonocytes, and type II pneumonocytes.

Cell membranes can also be obtained from cell type that is associated with a particular disease or with a specific disease stage. The association with a particular disease or disease stage may be established by the cell=s aberrant behavior in one or more biological processes such as cell cycle regulation, cell differentiation, apoptosis, chemotaxsis, cell motility and cytoskeletal rearrangement. A disease cell may also be confirmed by the presence of a pathogen causing the disease of concern (e.g. HIV for AIDS and HBV for hepatitis B). The types of diseases involving abnormal functioning of specific types of cells may include but are not limited to autoimmune diseases, cancer, obesity, hypertension, diabetes, neuronal and/or muscular degenerative diseases, cardiac diseases, endocrine disorders, and any combinations thereof. Exemplary types of tumor cells include adenomas, carcinomas, adenocarcinomas, fibroadenomas, ameloblastomas, astrocytomas, mesotheliomas, cholangiocarcinomas, cholangiofibromas, cholangiomas, chondromas, chondrosarcomas, chordomas, choriocarcinomas, craniopharyngiomas, cystadenocarcinomas, cystadenomas, dysgerminomas, ependymomas, epitheliomas, erythroid leukemias, fibroadenomas, fibromas, fibrosarcomas, gangliogliomas, ganglioneuromas, ganglioneuroblastomas, gliomas, granulocytic leukemias, hemangiomas, hemangiopericytomas, hemangiosarcomas, hibemomas, histiocytomas, keratoacanthomas, leiomyomas, leiomyosarcomas, lipomas, liposarcomas, luteomas, lymphangiomas, lymphangiosarcomas, lymphomas, medulloblastomas, melanomas, meningiomas, mesotheliomas, myelolipomas, nephroblastomas, neuroblastomas, neuromyoblastomas, odontomas, oligodendrogliomas, osteochondromas, osteomas, osteosarcomas, papillomas, paragangliomas, pheochromocytomas, pinealomas, pituicytomas, retinoblastomas, rhabdomyosarcomas, sarcomas, schwannomas, seminomas, teratomas, thecomas and thymomas.

Cell lines may also be transfected with genes encoding cell surface molecules. Furthermore, cells that endogenously express cell surface molecules may also be transfected to study the interactions between endogenous and foreign surface molecules. Preferred cells for transfection are those that transfect well and yield high levels of the expressed transfected gene product. Some preferred cells lines containing endogenously expressed cell surface receptors, many of which are useful for transfection include, e.g., CHO-K1 (Chinese hamster ovary) cells, HEK-293 (human embryonic kidney) cells, K562 (human chronic myelogenous leukemia) cells, MDA MB-231 (human breast cancer) cells, MCR-7 cells, HeLa (human cervical cancer) cells and COS-7 monkey kidney cells. Methods for culture and maintenance of these cell lines are well known in the art.

In another aspect of the invention, the membrane comprises liposomes. "Liposomes" are self-assembling structures comprising one or more lipid bilayers. Liposomes are usually composed of phospholipid bilayers, although other molecules, such as cholesterol or fatty acids can also be included in the bilayer construction. The phospholipid constituents of liposomes includes a hydrophobic lipid tail connected to a head constructed of various glycerylphosphate or silicone derivatives. Liposomes are thus normally made from amphipathic lipids comprise a polar (hydrophilic) headgroup region covalently linked to one or two non-polar (hydrophobic) acyl chains. Energetically unfavorable contacts between the hydrophobic acyl chains and the aqueous medium are generally believed to induce lipid molecules to rearrange such that the polar headgroups are oriented towards the aqueous medium while the acyl chains reorient towards the interior of the bilayer. An energetically stable structure is formed in which the acyl chains are effectively shielded from coming into contact with the aqueous medium. The hydrophobic interaction between the fatty acid tails thus creates the liposomal bilayers in aqueous solutions. In more complicated liposomal structures, one or more of the lipid bilayers can surround an aqueous compartment and comprises two opposing monolayers of amphipathic lipid molecules. Liposomes are thus completely closed bilayer membranes containing an encapsulated aqueous phase. Thus, liposomes may be any variety of multilamellar vesicles (concentric membrane bilayers each separated by an aqueous layer) or unilamellar vesicles (possessing a single membrane bilayer).

The liposomes may be prepared according to the method of Bangham et aL (1965) J. Mol. Biol. 13: 238–252, in which phospholipids were suspended in an organic solvent which was then evaporated to dryness leaving a waxy deposit of phospholipid on the reaction vessel. Then an appropriate amount of aqueous phase was added, the mixture was allowed to swell, and the resulting liposomes which consisted of multilamellar vesicles were dispersed by mechanical means. The structure of the resulting membrane bilayer is such that the hydrophobic (non-polar) "tails" of the lipid orient toward the center of the bilayer while the hydrophilic (polar) "heads" orient towards the aqueous phase. This technique provided the basis for the development of the small sonicated unilamellar vesicles described by Papahadjopoulos and Miller (1967) Biochim. Biophys. Acta. 135: 624–638. Normally, mixtures of phospholipids in aqueous solution will spontaneously associated to form liposomal structures, although techniques for controlling the size and shape of the liposomes are known in the art.

Methods

The following general discussion of methods and specific conditions and materials are by way of illustration and not limitation. One of ordinary skill in the art will understand how the methods described herein can be adapted to other applications, particularly with using different cell types and cell surface molecules.

In conducting the methods of the invention, a combination of the assay components is made, including the cells being tested, the tagged probes, and the cleaving probe. Generally, assay components may be combined in any order. In certain applications, however, the order of addition may be relevant. For example, one may wish to monitor competitive binding, such as in a quantitative assay. Or one may wish to monitor the stability of an assembled complex. In such applications, reactions may be assembled in stages, and may require incubations before the complete mixture has been assembled, or before the cleaving reaction is initiated.

The amounts of each reagent are usually determined empirically. The number of cells used in an assay will be determined by the predicted number of target complexes at the surface of each cell and the means of separation and detection used to monitor the signal of the assay. In general, the amounts of the tagged probes and the cleaving probe are provided in molar excess relative to the expected amount of the target molecules in the cells of the sample, generally at a molar excess of at least 1.5, more desirably about 10-fold excess, or more. In specific applications, the concentration used may be higher or lower, depending on the affinity of the binding agents and the expected number of target molecules present on a single cell. Where one is determining the effect of a chemical compound on formation of oligomeric cell surface complexes, the compound may be added to the cells prior to, simultaneously with, or after addition of the probes, depending on the effect being monitored.

The assay mixture is combined and incubated under conditions that provide for binding of the probes to the cell surface molecules, usually in an aqueous medium, generally at a physiological pH (comparable to the pH at which the cells are cultures), maintained by a buffer at a concentration in the range of about 10 to 200 mM. Conventional buffers may be used, as well as other conventional additives as necessary, such as salts, growth medium, stabilizers, etc. Physiological and constant temperatures are normally employed. Incubation temperatures normally range from about 4° to 70° C., usually from about 15° to 45° C., more usually 25°

After assembly of the assay mixture and incubation to allow the probes to bind to cell surface molecules, the mixture is treated to activate the cleaving agent to cleave the tags from the tagged probes that are within the effective proximity of the cleaving agent, releasing the corresponding tag from the cell surface into solution. The nature of this treatment will depend on the mechanism of action of the cleaving agent. For example, where a photosensitizer is employed as the cleaving agent, activation of cleavage will comprise irradiation of the mixture at the wavelength of light appropriate to the particular sensitizer used.

Following cleavage, the sample is then analyzed to determine the identity of tags that have been released. Where an assay employing a plurality of tagged probes is employed, separation of the released tags will generally precede their detection. The methods for both separation and detection are determined in the process of designing the tags for the assay. A preferred mode of separation employs electrophoresis, in which the various tags are separated based on known differences in their electrophoretic mobilities.

Separation of Released Molecular Tags

As mentioned above, molecular tags are designed for separation by a separation technique that can distinguish molecular tags based on one or more physical, chemical, and/or optical characteristics (referred to herein as "separation characteristics"). As also mentioned above, separation techniques that may be used with the various embodiments of the invention include normal phase or reverse phase HPLC, ion exchange HPLC, capillary electrochromatography, mass spectroscopy, gas phase chromatography, and the like. Preferably, the separation technique selected is capable of providing quantitative information as well as qualitative information about the presence or absence of molecular tags (and therefore, corresponding analytes). In one aspect, a liquid phase separation technique is employed so that a solution, e.g. buffer solution, reaction solvent, or the like, containing a mixture of molecular tags is processed to bring about separation of individual kinds of molecular tags. Usually, such separation is accompanied by the differential movement of molecular tags from such a starting mixture along a path until discernable peaks or bands form that correspond to regions of increased concentration of the respective molecular tags. Such a path may be defined by a fluid flow, electric field, magnetic field, or the like. The selection of a particular separation technique depends on several factors including the expense and convenience of using the technique, the resolving power of the technique given the chemical nature of the molecular tags, the number of molecular tags to be separated, the type of detection mode employed, and the like. Preferably, molecular tags are electrophoretically separated to form an electropherogram in which the separated molecular tags are represented by distinct peaks.

A. Electrophoretic Separation

Methods for electrophoresis of are well known and there is abundant guidance for one of ordinary skill in the art to make design choices for forming and separating particular pluralities of molecular tags. The following are exemplary references on electrophoresis: Krylov et al, Anal. Chem., 72: 111 R-128R (2000); P. D. Grossman and J. C. Colbum, Capillary Electrophoresis: Theory and Practice, Academic Press, Inc., NY (1992); U.S. Pat. Nos. 5,374,527; 5,624,800; 5,552,028; ABI PRISM 377 DNA Sequencer User's Manual, Rev. A, January 1995, Chapter 2 (Applied Biosystems, Foster City, Calif.); and the like. In one aspect, molecular tags are separated by capillary electrophoresis. Design choices within the purview of those of ordinary skill include but are not limited to selection of instrumentation from several commercially available models, selection of operating conditions including separation media type and concentration, pH, desired separation time, temperature, voltage, capillary type and dimensions, detection mode, the number of molecular tags to be separated, and the like.

In one aspect of the invention, during or after electrophoretic separation, the molecular tags are detected or identified by recording fluorescence signals and migration times (or migration distances) of the separated compounds, or by constructing a chart of relative fluorescent and order of migration of the molecular tags (e.g., as an electropherogram). To perform such detection, the molecular tags can be illuminated by standard means, e.g. a high intensity mercury vapor lamp, a laser, or the like. Typically, the molecular tags are illuminated by laser light generated by a He—Ne gas laser or a solid-state diode laser. The fluorescence signals can then be detected by a light-sensitive detector, e.g., a photomultipliet tube, a charged-coupled device, or the like. Exemplary electrophoresis detection systems are described elsewhere, e.g., U.S. Pat. Nos. 5,543,026; 5,274,240; 4,879, 012; 5,091,652; 6,142,162; or the like. In another aspect, molecular tags may be detected electrochemically detected, e.g. as described in U.S. Pat. No. 6,045,676.

Electrophoretic separation involves the migration and separation of molecules in an electric field based on differences in mobility. Various forms of electrophoretic separation include, by way of example and not limitation, free zone electrophoresis, gel electrophoresis, isoelectric focusing, isotachophoresis, capillary electrochromatography, and micellar electrokinetic chromatography. Capillary electrophoresis involves electroseparation, preferably by electrokinetic flow, including electrophoretic, dielectrophoretic and/or electroosmotic flow, conducted in a tube or channel of from about 1 to about 200 micrometers, usually, from about 10 to about 100 micrometers cross-sectional dimensions. The capillary may be a long independent capillary tube or a channel in a wafer or film comprised of silicon, quartz, glass or plastic.

In capillary electroseparation, an aliquot of the reaction mixture containing the molecular tags is subjected to electroseparation by introducing the aliquot into an electroseparation channel that may be part of, or linked to, a capillary device in which the amplification and other reactions are performed. An electric potential is then applied to the electrically conductive medium contained within the channel to effectuate migration of the components within the combination. Generally, the electric potential applied is sufficient to achieve electroseparation of the desired components according to practices well known in the art. One skilled in the art will be capable of determining the suitable electric potentials for a given set of reagents used in the present invention and/or the nature of the cleaved labels, the nature of the reaction medium and so forth. The parameters for the electroseparation including those for the medium and the electric potential are usually optimized to achieve maximum separation of the desired components. This may be achieved empirically and is well within the purview of the skilled artisan.

Detection may be by any of the known methods associated with the analysis of capillary electrophoresis columns including the methods shown in U.S. Pat. Nos. 5,560,811 (column 11, lines 19–30), 4,675,300, 4,274,240 and 5,324,401, the relevant disclosures of which are incorporated herein by reference. Those skilled in the electrophoresis arts will recognize a wide range of electric potentials or field strengths may be used, for example, fields of 10 to 1000 V/cm are used with about 200 to about 600 V/cm being more typical. The upper voltage limit for commercial systems is about 30 kV, with a capillary length of about 40 to about 60 cm, giving a maximum field of about 600 V/cm. For DNA, typically the capillary is coated to reduce electroosmotic flow, and the injection end of the capillary is maintained at a negative potential.

For ease of detection, the entire apparatus may be fabricated from a plastic material that is optically transparent, which generally allows light of wavelengths ranging from about 180 to about 1500 nm, usually about 220 to about 800 nm, more usually about 450 to about 700 nm, to have low transmission losses. Suitable materials include fused silica, plastics, quartz, glass, and so forth.

In one aspect of the invention, molecular tags are separated by electrophoresis in a microfluidics device, as illustrated diagrammatically in FIGS. 16A–16C. Microfluidics devices are described in a number of domestic and foreign Letters Patent and published patent applications. See, for example, U.S. Pat. Nos. 5,750,015; 5,900,130; 6,007,690; and WO 98/45693; WO 99/19717 and WO 99/15876. Conveniently, an aliquot, generally not more than about 5 μl, is transferred to the sample reservoir of a microfluidics device, either directly through electrophoretic or pneumatic injection into an integrated system or by syringe, capillary or the like. The conditions under which the separation is performed are conventional and will vary with the nature of the products.

Figure 8A:
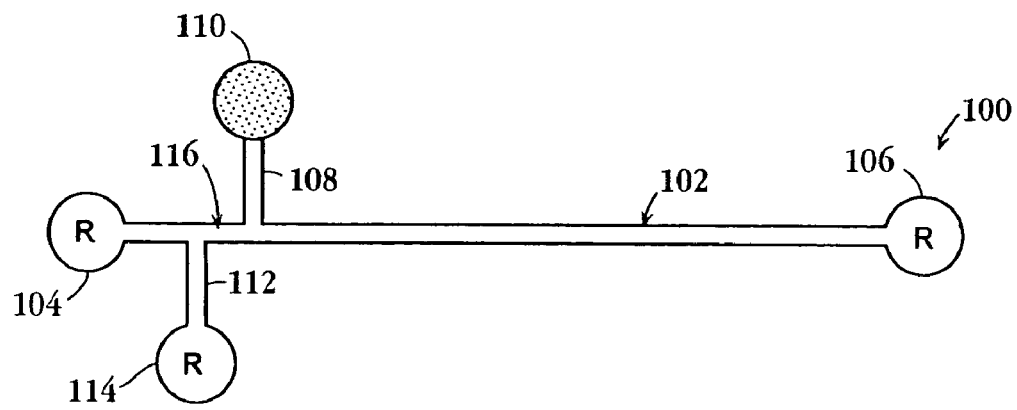
FIGS. 8A–8C diagrammatically illustrate a microfluidics device for implementing a step of electrophoretically separating molecular tags.
Figure 8B:
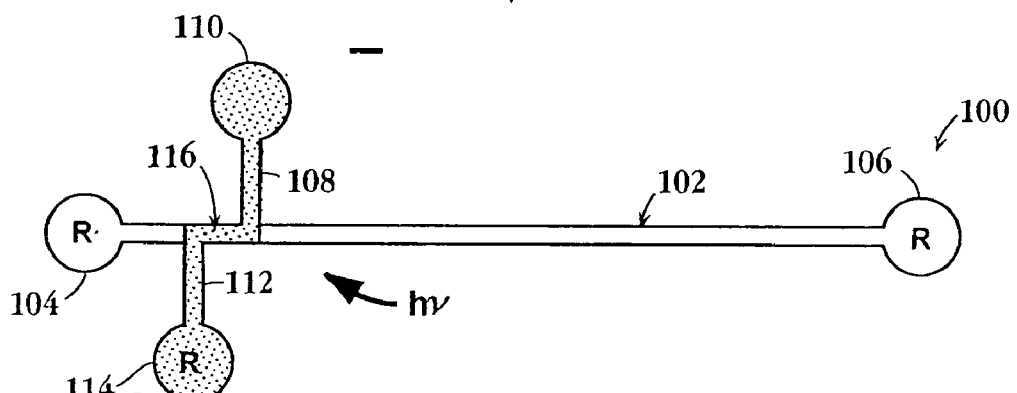
Figure 8C:
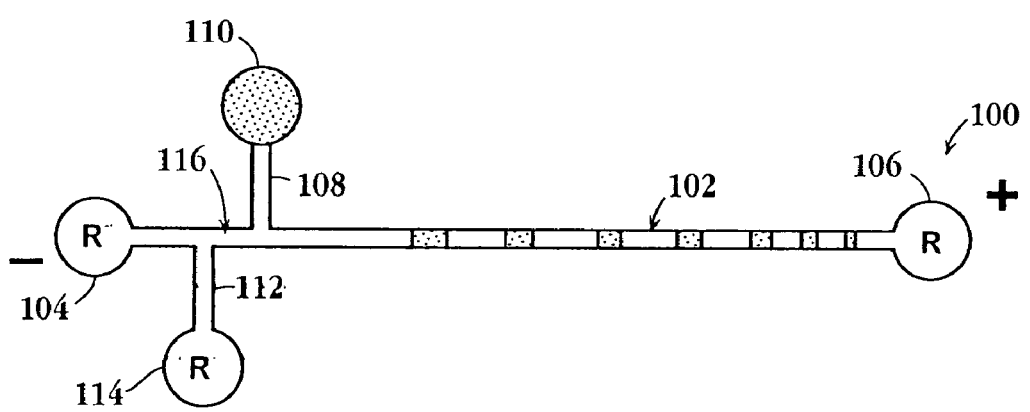

By way of illustration, FIGS. 8A–8C show a microchannel network 100 in a microfluidics device of the type detailed in the application noted above, for sample loading and electrophoretic separation of a sample of probes and tags produced in the assay above. Briefly, the network includes a main separation channel 102 terminating at upstream and downstream reservoirs 104, 106, respectively. The main channel is intersected at offset axial positions by a side channel 108 that terminates at a reservoir 110, and a side channel 112 that terminates at a reservoir 114. The offset between the two-side channels forms a sample loading zone 116 within the main channel.

In operation, an assay mixture is placed in sample reservoir 110, illustrated in FIG. 8A. As noted, the assay mixture contains one or more target cells with surface-bound cleaving agent, one or more protein probes, and optionally, molecular tag standard. The assay reaction, involving initial probe binding to target cell(s), followed by cleavage of probe linkers in probe-bound cells, may be carried out in sample reservoir 110, or alternatively, the assay reactions can be carried out in another reaction vessel, with the reacted sample components the added to the sample reservoir.

To load released molecular tags into the sample-loading zone, an electric field is applied across reservoirs 110, 114, in the direction indicated in FIG. 8B, wherein negatively charged released molecular tags are drawn from reservoir 110 into loading zone 116, while uncharged or positively charged sample components remain in the sample reservoir. The released tags in the loading zone can now be separated by conventional capillary electrophoresis, by applying an electric filed across reservoirs 104, 106, in the direction indicated in FIG. 8C.

From the resulting electrophoretic pattern, the molecular tags, and corresponding analytes, can be identified. This is typically done by placing a fluorescence detector near the downstream end of the separation channel, and constructing a electropherogram of the separated molecular tags, first to determine the separation characteristic (in this case, electrophoretic mobility) as above, and secondly, to measure signal intensity, e.g., peak height or peak area, as a measure of the relative amount of tag associated with each probe. Methods for detecting and quantifying levels of a detectable probe are well known. In one preferred method, the molecular tags are fluorescent labeled. A standard fluorescence-emission source is directed against a detection zone in a downstream portion of the separation medium, and fluorescence emission of the zone is measured by a standard light detector. The signal height or area recorded provides a measure of product and substrate concentration in the sample.

With the above detection information, it is now possible to assign each detected molecular tag to a particular probe in the probe set, and to compare the relative levels of each detectable probe, as a measure of its relatively substrate conversion or ligand binding.

B. Chromatographic Separation

In one aspect of the invention, pluralities of molecular tags are designed for separation by chromatography based on one or more physical characteristics that include but are not limited to molecular weight, shape, solubility, pKa, hydrophobicity, charge, polarity, or the like. A chromatographic separation technique is selected based on parameters such as column type, solid phase, mobile phase, and the like, followed by selection of a plurality of molecular tags that may be separated to form distinct peaks or bands in a single operation. Several factors determine which HPLC technique is selected for use in the invention, including the number of molecular tags to be detected (i.e. the size of the plurality), the estimated quantities of each molecular tag that will be generated in the assays, the availability and ease of synthesizing molecular tags that are candidates for a set to be used in multiplexed assays, the detection modality employed, and the availability, robustness, cost, and ease of operation of HPLC instrumentation, columns, and solvents. Generally, columns and techniques are favored that are suitable for analyzing limited amounts of sample and that provide the highest resolution separations. Guidance for making such selections can be found in the literature, e.g. Snyder et al, Practical HPLC Method Development, (John Wiley & Sons, New York, 1988); Millner, "High Resolution Chromatography: A Practical Approach", Oxford University Press, New York (1999), Chi-San Wu, "Column Handbook for Size Exclusion Chromatography", Academic Press, San Diego (1999), and Oliver, "HPLC of Macromolecules: A Practical Approach, Oxford University Press", Oxford, England (1989). In particular, procedures are available for systematic development and optimization of chromatographic separations given conditions, such as column type, solid phase, and the like, e.g. Haber et al, J. Chromatogr. Sci., 38: 386–392

(2000); Outinen et al, Eur. J. Pharm. Sci., 6: 197–205 (1998); Lewis et al, J. Chromatogr., 592: 183–195 and 197–208 (1992); and the like.

In one aspect, initial selections of molecular tag candidates are governed by the physiochemical properties of molecules typically separated by the selected column and stationary phase. The initial selections are then improved empirically by following conventional optimization procedure, as described in the above reference, and by substituting more suitable candidate molecular tags for the separation objectives of a particular embodiment. In one aspect, separation objectives of the invention include (i) separation of the molecular tags of a plurality into distinguishable peaks or bands in a separation time of less than 60 minutes, and more preferably in less than 40 minutes, and still more preferably in a range of between 10 to 40 minutes, (ii) the formation of peaks or bands such that any pair has a resolution of at least 1.0, more preferably at least 1.25, and still more preferably, at least 1.50, (iii) column pressure during separation of less than 150 bar, (iv) separation temperature in the range of from 25° C. to 90° C., preferably in the range of from 35° C. to 80° C., and (v) the plurality of distinguishable peaks is in the range of from 5 to 30 and all of the peaks in the same chromatogram. As used herein, "resolution" in reference to two peaks or bands is the distance between the two peak or band centers divided by the average base width of the peaks, e.g. Snyder et al (cited above). A chromatographic method is used to separate molecular tags based on their chromatographic properties. A chromatographic property can be, for example, a retention time of a molecular tag on a specific chromatographic medium under defined conditions, or a specific condition under which a molecular tag is eluted from a specific chromatographic medium. A chromatographic property of a molecular tag can also be an order of elution, or pattern of elution, of a molecular tag contained in a group or set of molecular tags being chromatographically separated using a specific chromatographic medium under defined conditions. A chromatographic property of a molecular tag is determined by the physical properties of the molecular tag and its interactions with a chromatographic medium and mobile phase. Defined conditions for chromatography include particular mobile phase solutions, column geometry, including column diameter and length, pH, flow rate, pressure and temperature of column operation, and other parameters that can be varied to obtain the desired separation of molecular tags. A molecular tag, or chromatographic property of a molecular tag, can be detected using a variety of chromatography methods.

Sets of molecular tags detected in a single experiment generally are a group of chemically related molecules that differ by mass, charge, mass-charge ratio, detectable tag, such as differing fluorophores or isotopic labels, or other unique characteristic. Therefore, both the chemical nature of the molecular tag and the particular differences among molecular tags in a group of molecular tags can be considered when selecting a suitable chromatographic medium for separating molecular tags in a sample.

Separation of molecular tags by liquid chromatography can be based on physical characteristics of molecular tags such as charge, size and hydrophobicity of molecular tags, or functional characteristics such as the ability of molecular tags to bind to molecules such as dyes, lectins, drugs, peptides and other ligands on an affinity matrix. A wide variety of chromatographic media are suitable for separation of molecular tag based on charge, size, hydrophobicity and other chromatographic properties of molecular tags. Selection of a particular chromatographic medium will depend upon the properties of molecular tags employed.

Separated molecular tags can be detected using a variety of analytical methods, including detection of intrinsic properties of molecular tags, such as absorbance, fluorescence or electrochemical properties, as well as detection of a detection group or moiety attached to a molecular tag. Although not required, a variety of detection groups or moieties can be attached to molecular tags to facilitate detection after chromatographic separation.

Detection methods for use with liquid chromatography are well known, commercially available, and adaptable to automated and high-throughput sampling. The detection method selected for analysis of molecular tags will depend upon whether the molecular tags contain a detectable group or moiety, the type of detectable group used, and the physicochemical properties of the molecular tag and detectable group, if used. Detection methods based on fluorescence, electrolytic conductivity, refractive index, and evaporative light scattering can be used to detect various types of molecular tags.

A variety of optical detectors can be used to detect a molecular tag separated by liquid chromatography. Methods for detecting nucleic acids, polypeptides, peptides, and other macromolecules and small molecules using ultraviolet (UV)/visible spectroscopic detectors are well known, making UV/visible detection the most widely used detection method for HPLC analysis. Infrared spectrophotometers also can be used to detect macromolecules and small molecules when used with a mobile phase that is a transparent polar liquid.

Variable wavelength and diode-array detectors represent two commercially available types of UV/visible spectrophotometers. A useful feature of some variable wavelength UV detectors is the ability to perform spectroscopic scanning and precise absorbance readings at a variety of wavelengths while the peak is passing through the flowcell. Diode array technology provides the additional advantage of allowing absorbance measurements at two or more wavelengths, which permits the calculation of ratios of such absorbance measurements. Such absorbance rationing at multiple wavelengths is particularly helpful in determining whether a peak represents one or more than one molecular tag.

Fluorescence detectors can also be used to detect fluorescent molecular tags, such as those containing a fluorescent detection group and those that are intrinsically fluorescent. Typically, fluorescence sensitivity is relatively high, providing an advantage over other spectroscopic detection methods when molecular tags contain a fluorophore. Although molecular tags can have detectable intrinsic fluorescence, when a molecular tag contains a suitable fluorescent detection group, it can be possible to detect a single molecular tag in a sample.

Electrochemical detection methods are also useful for detecting molecular tags separated by HPLC. Electrochemical detection is based on the measurement of current resulting from oxidation or reduction reaction of the molecular tags at a suitable electrode. Since the level of current is directly proportional to molecular tag concentration, electrochemical detection can be used quantitatively, if desired.

Evaporative light scattering detection is based on the ability of particles to cause photon scattering when they traverse the path of a polychromatic beam of light. The liquid effluent from an HPLC is first nebulized and the resultant aerosol mist, containing the molecular tags, is directed through a light beam. A signal is generated that is proportional to the amount of the molecular tag present in a sample, and is independent of the presence or absence of detectable groups such as chromophores, fluorophores or electroactive groups. Therefore, the presence of a detection group or moiety on a molecular tag is not required for evaporative light scattering detection.

Mass spectrometry methods also can be used to detect molecular tags separated by HPLC. Mass spectrometers can resolve ions with small mass differences and measure the mass of ions with a high degree of accuracy and sensitivity. Mass spectrometry methods are well known in the art (see Burlingame et al. *Anal. Chem.* 70:647R-716R (1998); Kinter and Sherman, Protein Sequencing and Identification Using Tandem Mass Spectrometry Wiley-Interscience, New York (2000)).

Analysis of data obtained using any detection method, such as spectral deconvolution and quantitative analysis can be manual or computer-assisted, and can be performed using automated methods. A variety of computer programs can be used to determine peak integration, peak area, height and retention time. Such computer programs can be used for convenience to determine the presence of a molecular tag qualitatively or quantitatively. Computer programs for use with HPLC and corresponding detectors are well known to those skilled in the art and generally are provided with commercially available HPLC and detector systems.

A variety of commercially available systems are well-suited for high throughput analysis of molecular tags. Those skilled in the art can determine appropriate equipment, such as automated sample preparation systems and autoinjection systems, useful for automating HPLC analysis of molecular tags. Automated methods can be used for high-throughput analysis of molecular tags, for example, when a large number of samples are being processes or for multiplexed application of the methods of the invention for detecting target analytes. An exemplary HPLC instrumentation system suitable for use with the present invention is the Agilent 1100 Series HPLC system (Agilent Technologies, Palo Alto, Calif.).

Those skilled in the art will be aware of quality control measures useful for obtaining reliable analysis of molecular tags, particular when analysis is performed in a high-throughput format. Such quality control measures include the use of external and internal reference standards, analysis of chromatograph peak shape, assessment of instrument performance, validation of the experimental method, for example, by determining a range of linearity, recovery of sample, solution stability of sample, and accuracy of measurement.

C. Separation by Mass Spectrometry

Mass spectrometry methods are well known in the art (see Burlingame et al. Anal. Chem. 70:647R-716R (1998); Kinter and Sherman, Protein Sequencing and Identification Using Tandem Mass Spectrometry Wiley-Interscience, New York (2000)). The basic processes associated with a mass spectrometry method are the generation of gas-phase ions derived from the sample, and the measurement of their mass.

The movement of gas-phase ions can be precisely controlled using electromagnetic fields generated in the mass spectrometer. The movement of ions in these electromagnetic fields is proportional to the m/z of the ion and this forms the basis of measuring the m/z and therefore the mass of a sample. The movement of ions in these electromagnetic fields allows the ions to be contained and focused which accounts for the high sensitivity of mass spectrometry. During the course of m/z measurement, ions are transmitted with high efficiency to particle detectors that record the arrival of these ions. The quantity of ions at each m/z is demonstrated by peaks on a graph where the x axis is m/z and the y axis is relative abundance. Different mass spectrometers have different levels of resolution, that is, the ability to resolve peaks between ions closely related in mass. The resolution is defined as R-midelta m, where m is the ion mass and delta m is the difference in mass between two peaks in a mass spectrum. For example, a mass spectrometer with a resolution of 1000 can resolve an ion with a ni/z of 100.0 from an ion with a m/z of 100.1.

Several types of mass spectrometers are available or can be produced with various configurations. In general, a mass spectrometer has the following major components: a sample inlet, an ion source, a mass analyzer, a detector, a vacuum system, and instrument-control system, and a data system. Difference in the sample inlet, ion source, and mass analyzer generally define the type of instrument and its capabilities. For example, an inlet can be a capillary-coluin liquid chromatography source or can be a direct probe or stage such as used in matrix-assisted laser desorption. Common ion sources are, for example, electrospray, including nanospray and microspray or matrix-assisted laser desorption. Exemplary mass analyzers include a quadrupole mass filter, ion trap mass analyzer and time-of-flight mass analyzer.

The ion formation process is a starting point for mass spectrum analysis. Several ionization methods are available and the choice of ionization method depends on the sample to be analyzed. For example, for the analysis of polypeptides a relatively gentle ionization procedure such as electrospray ionization (ESI) can be desirable. For ESI, a solution containing the sample is passed through a fine needle at high potential, which creates a strong electrical field resulting in a fine spray of highly charged droplets that is directed into the mass spectrometer. Other ionization procedures include, for example, fast-atom bombardment (FAB), which uses a high-energy beam of neutral atoms to strike a solid sample causing desorption and ionization. Matrix-assisted laser desorption ionization (MALDI) is a method in which a laser pulse is used to strike a sample that has been crystallized in an UV-absorbing compound matrix. Other ionization procedures known in the art include, for example, plasma and glow discharge, plasma desorption ionization, resonance ionization, and secondary ionization. A tag reporter can become ionized prior to, during, or after cleavage from the tagged probe.

Electrospray ionization (ESI) has several properties that are usefuil for the invention described herein. For example, ESI can be used for biological molecules such as polypeptides that are difficult to ionize or vaporize. In addition, the efficiency of ESI can be very high which provides the basis for highly sensitive measurements. Furthermore, ESI produces charged molecules from solution, which is convenient for analyzing tag reporters that are in solution. In contrast, ionization procedures such as MALDI require crystallization of the sample prior to ionization.

Since ESI can produce charged molecules directly from solution, it is compatible with samples from liquid chromatography systems. For example, a mass spectrometer can have an inlet for a liquid chromatography system, such as an HPLC, so that fractions flow from the chromatography column into the mass spectrometer. This in-line arrangement of a liquid chromatography system and mass spectrometer is sometimes referred to as LC-MS. A LC-MS system can be used, for example, to separate un-cleaved or partially cleaved tag reporters from cleaved tag reporters before mass spectrometry analysis. In addition, chromatography can be used to remove salts or other buffer components from the tag reporter sample before mass spectrometry analysis. For example, desalting of a sample using a reversed-phase HPLC column, in-line or off-line, can be used to increase the efficiency of the ionization process and thus improve sensitivity of detection by mass spectrometry.

A variety of mass analyzers are available that can be paired with different ion sources. Different mass analyzers have different advantages as known to one skilled in the art and as described herein. The mass spectrometer and methods chosen for detection depends on the particular assay, for example, a more sensitive mass analyzer can be used when a small amount of ions are generated for detection. Several types of mass analyzers and mass spectrometry methods are described below.

Quadrupole mass spectrometry utilizes a quadrupole mass filter or analyzer. This type of mass analyzer is composed of four rods arranged as two sets of two electrically connected rods. A combination of rf and dc voltages are applied to each pair of rods which produces fields that cause an oscillating movement of the ions as they move from the beginning of the mass filter to the end. The result of these fields is the production of a high-pass mass filter in one pair of rods and a low-pass filter in the other pair of rods. Overlap between the high-pass and low-pass filter leaves a defined m/z that can pass both filters and traverse the length of the quadrupole. This m/z is selected and remains stable in the quadrupole mass filter while all other m/z have unstable trajectories and do not remain in the mass filter. A mass spectrum results by ramping the applied fields such that an increasing m/z is selected to pass through the mass filter and reach the detector. In addition, quadrupoles can also be set up to contain and transmit ions of all m/z by applying a rf-only field. This allows quadrupoles to fuinction as a lens or focusing system in regions of the mass spectrometer where ion transmission is needed without mass filtering. This will be of use in tandem mass spectrometry as described further below.

A quadrupole mass analyzer, as well as the other mass analyzers described herein, can be programmed to analyze a defined m/z or mass range. This property of mass spectrometers is useful for the invention described herein. Since the mass range of cleaved tag reporters will be known prior to an assay, a mass spectrometer can be programmed to transmit ions of the projected correct mass range while excluding ions of a higher or lower mass range. The ability to select a mass range can decrease the background noise in the assay and thus increase the signal-to-noise ratio. In addition, a defined mass range can be used to exclude analysis of any un-cleaved or partially-cleaved tagged probes, which would be of higher mass than the mass of the fuilly-cleaved tagged probes (tag reporters). Therfore, the mass spectrometer can accomplish an inherent separation step as well as detection and identification of the tag reporters.

Ion trap mass spectrometry utilizes an ion trap mass analyzer. In these mass analyzers, fields are applied so that ions of all In/z are initially trapped and oscillate in the mass analyzer. Ions enter the ion trap from the ion source through a focusing device such as an octapole lens system. Ion trapping takes place in the trapping region before excitation and ejection through an electrode to the detector. Mass analysis is accomplished by sequentially applying voltages that increase the amplitude of the oscillations in a way that ejects ions of increasing m/z out of the trap and into the detector. In contrast to quadrupole mass spectrometry, all ions are retained in the fields of the mass analyzer except those with the selected nlz. One advantage to ion traps is that they have very high sensitivity, as long as one is careful to limit the number of ions being tapped at one time. Control of the number of ions can be accomplished by varying the time over which ions are injected into the trap. The mass resolution of ion traps is similar to that of quadrupole mass filters, although ion traps do have low nlz limitations.

Time-of-flight mass spectrometry utilizes a time-of-flight mass analyzer. For this method of m/z analysis, an ion is fust given a fixed amount of kinetic energy by acceleration in an electric field (generated by high voltage). Following acceleration, the ion enters a field-free or "drift" region where it travels at a velocity that is inversely proportional to its m/z. Therefore, ions with low m/z travel more rapidly than ions with high m/z. The time required for ions to travel the length of the field-free region is measured and used to calculate the m/z of the ion.

One consideration in this type of mass analysis is that the set of ions being studied be introduced into the analyzer at the same time. For example, this type of mass analysis is well suited to ionization techniques like MALDI which produces ions in short well-defined pulses. Another consideration is to control velocity spread produced by ions that have variations in their amounts of kinetic energy. The use of longer flight tubes, ion reflectors, or higher accelerating voltages can help minimize the effects of velocity spread. Time-of-flight mass analyzers have a high level of sensitivity and a wider m/z range than quadrupole or ion trap mass analyzers. Also data can be acquired quickly with this type of mass analyzer because no scanning of the mass analyzer is necessary.

Synthesis of Assay Reagents

Figure 5A:
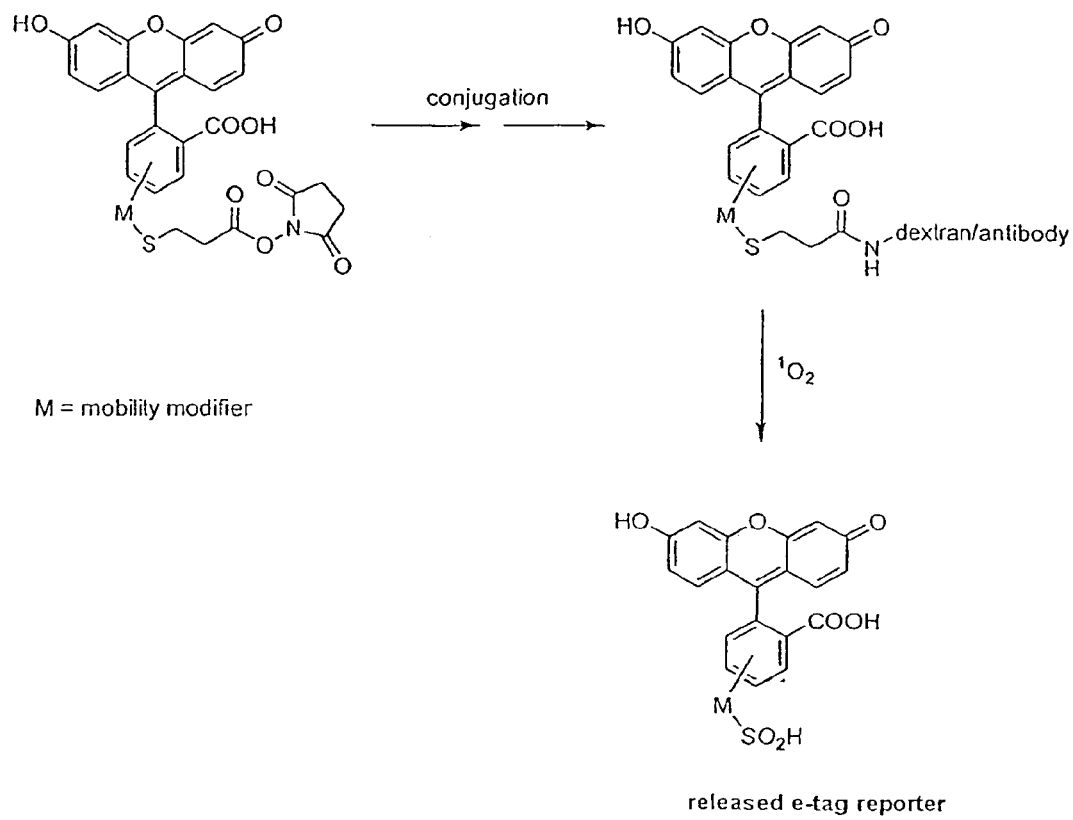
FIG. 5A illustrates a general methodology for conjugation of a tag to an antibody to form a tagged probe, and the reaction of the resulting tagged probe with singlet oxygen to produce a sulfinic acid moiety as the released tag.
Figure 5B:
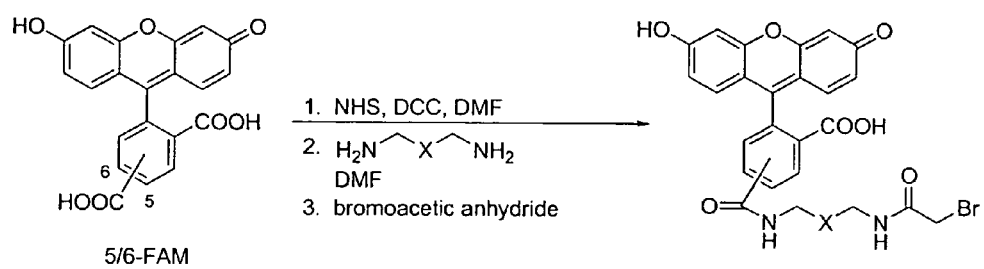
FIG. 5B outlines the chemistry of synthesis of fluorescein-labeled molecular tags.
Figure 5B:
Figure 5B:
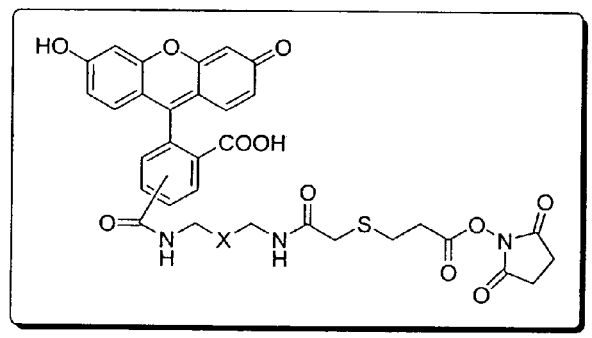
Figure 6A:
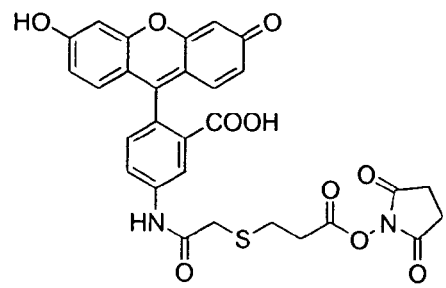
FIGS. 6A–J show the structures of tags that have been designed and synthesized.
Figure 6A:
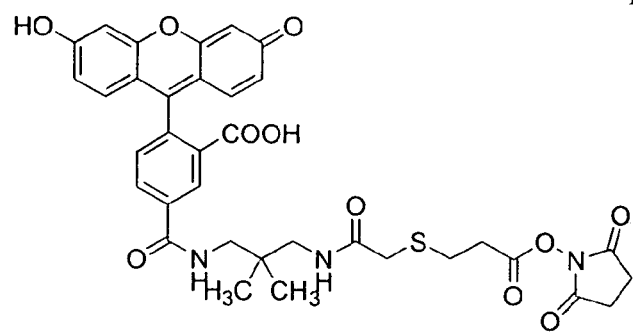
Figure 6A:
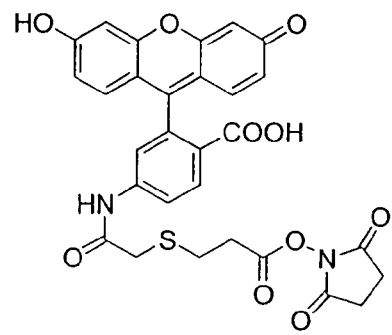
Figure 6A:
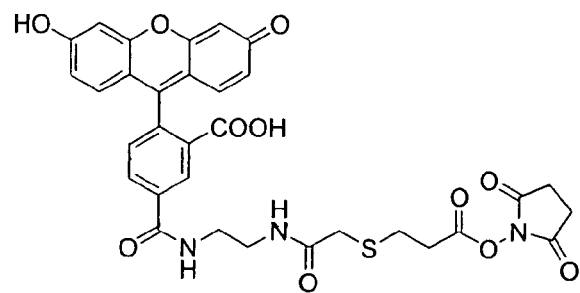
Figure 6B:
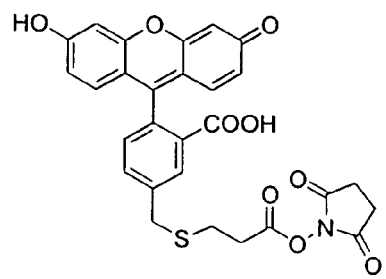
Figure 6B:
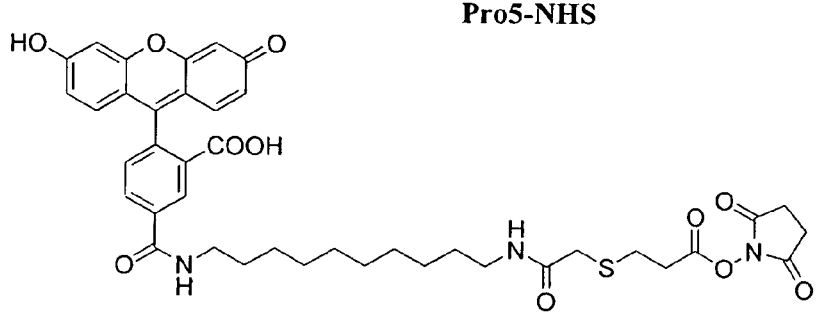
Figure 6B:
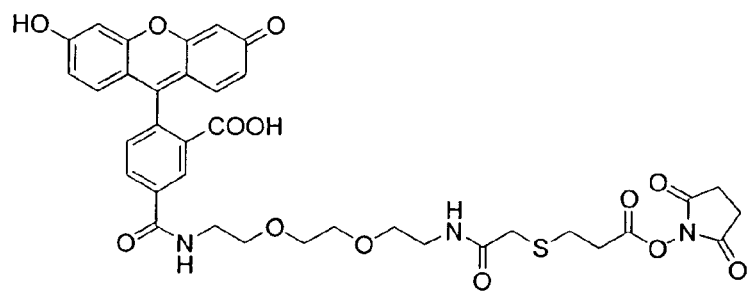
Figure 6B:
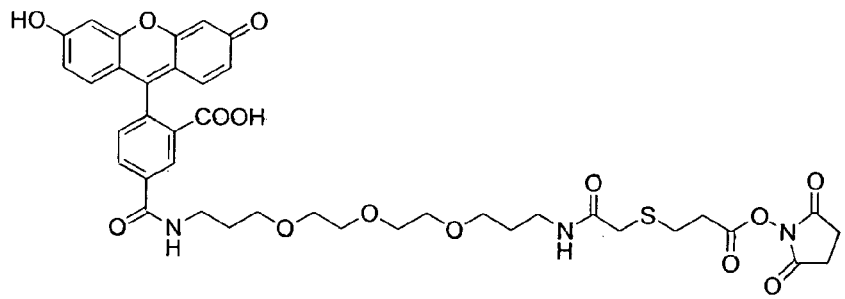
Figure 6C:
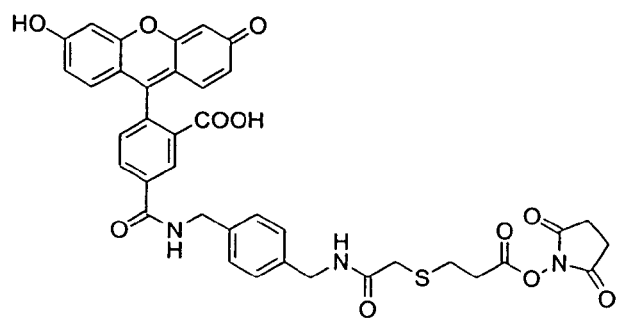
Figure 6C:
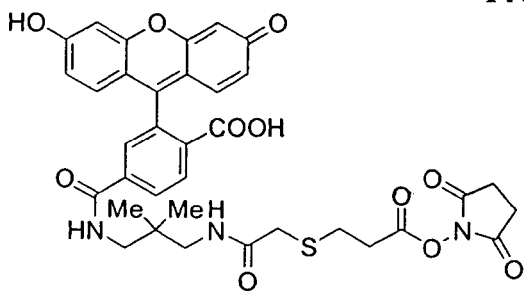
Figure 6C:
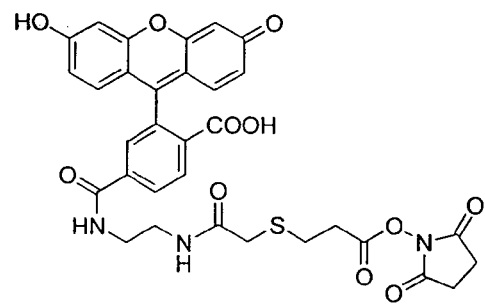
Figure 6C:
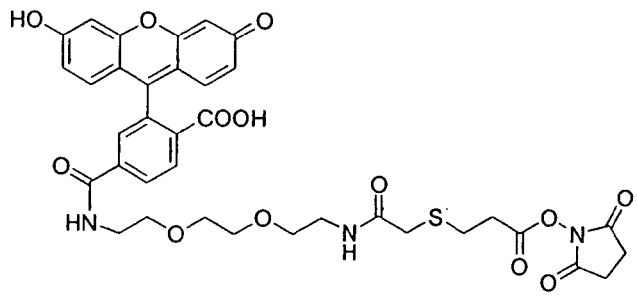
Figure 6D:
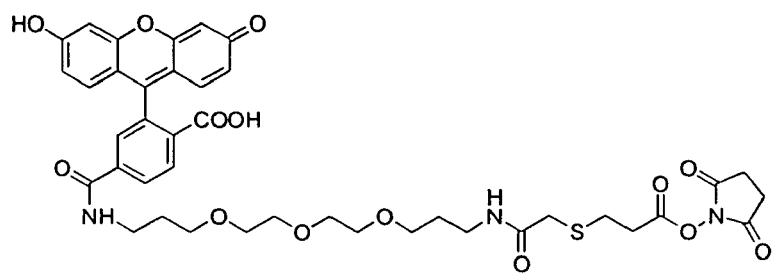
Figure 6D:
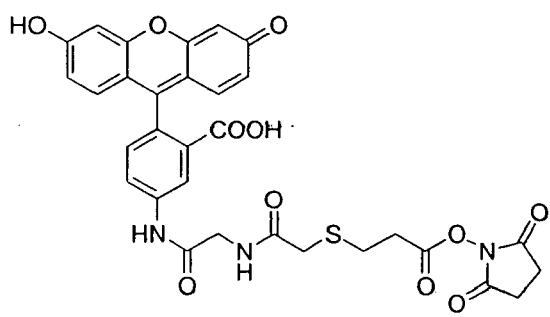
Figure 6D:
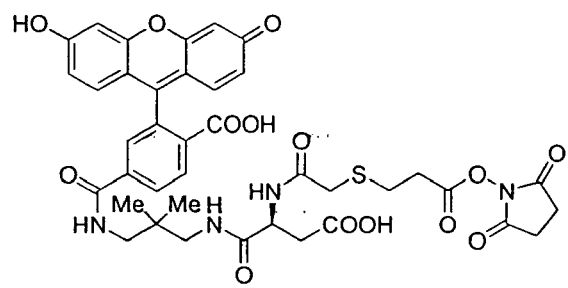
Figure 6D:
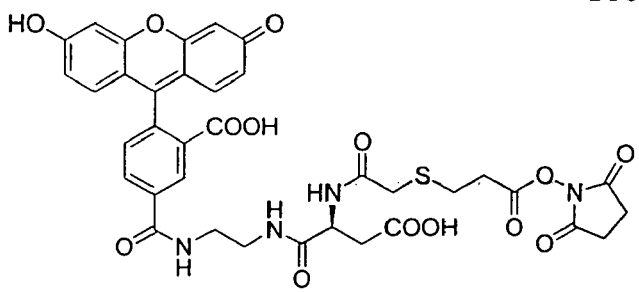
Figure 6E:
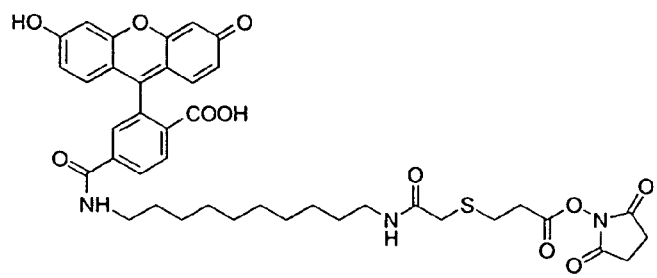
Figure 6E:
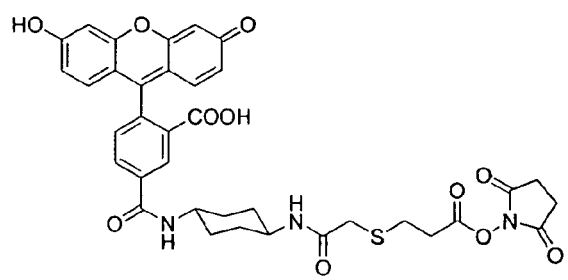
Figure 6E:
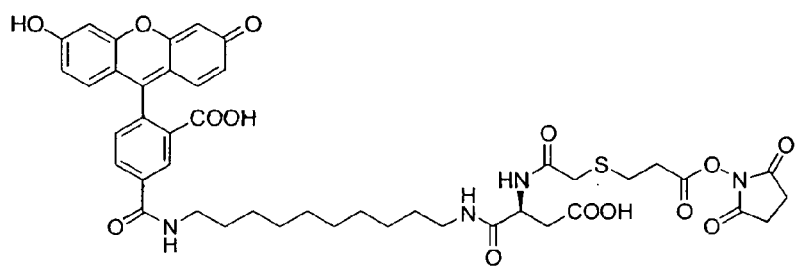
Figure 6E:
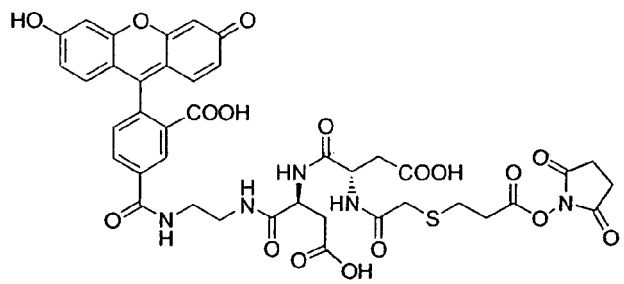
Figure 6F:
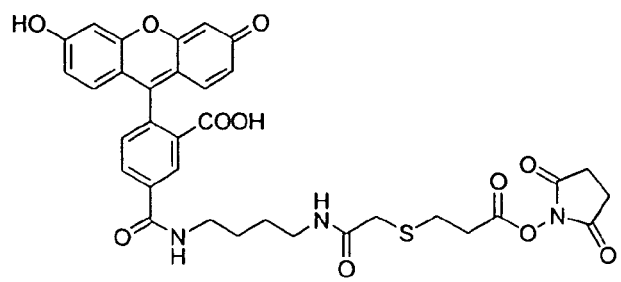
Figure 6F:
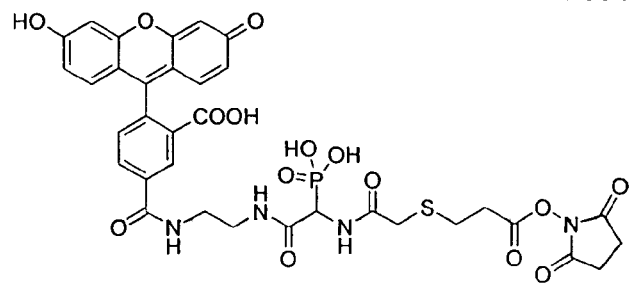
Figure 6F:
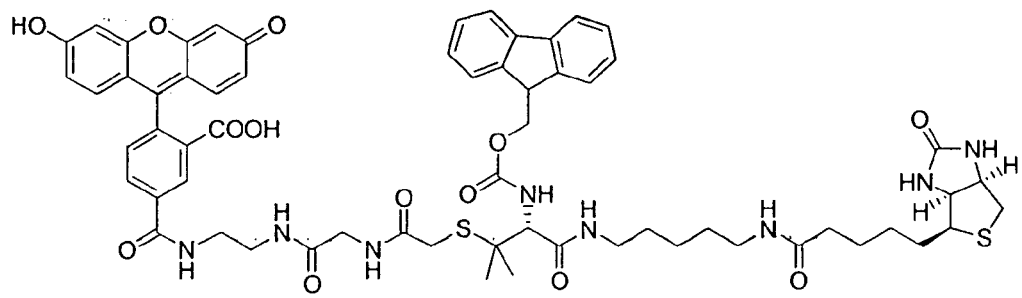
Figure 6F:
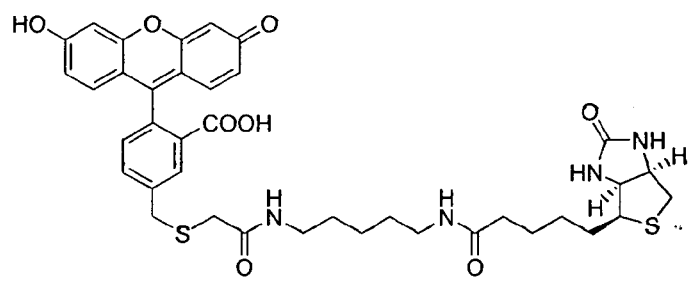
Figure 6G:
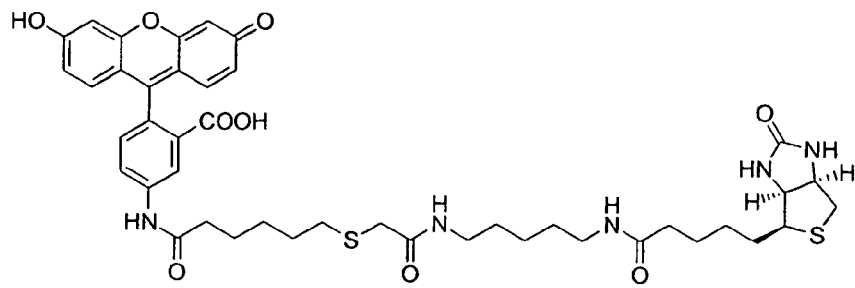
Figure 6G:
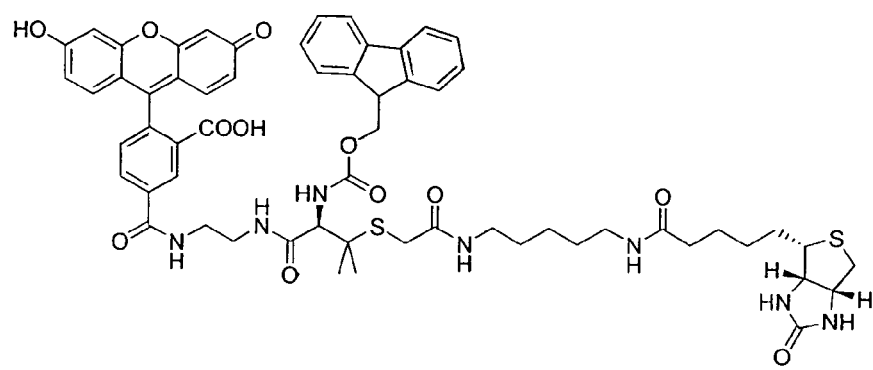
Figure 6G:
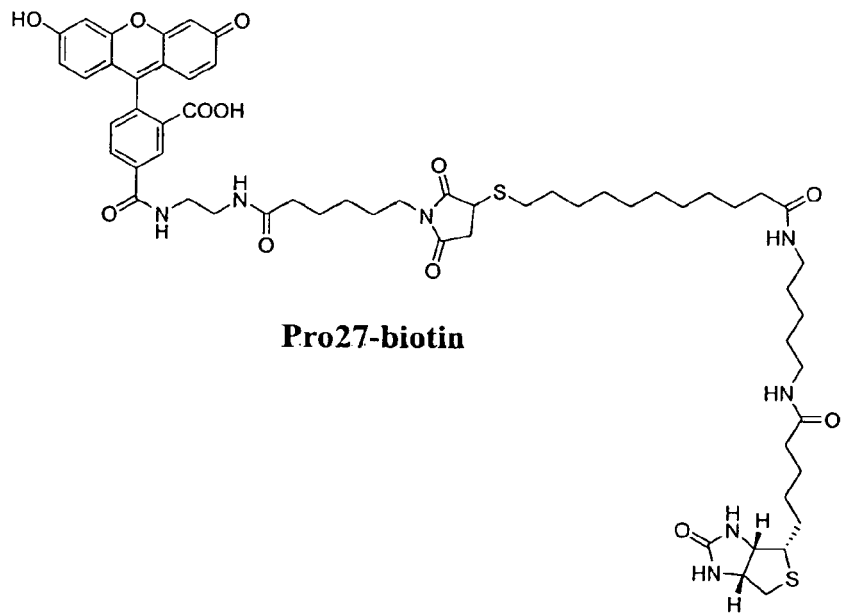
Figure 6H:
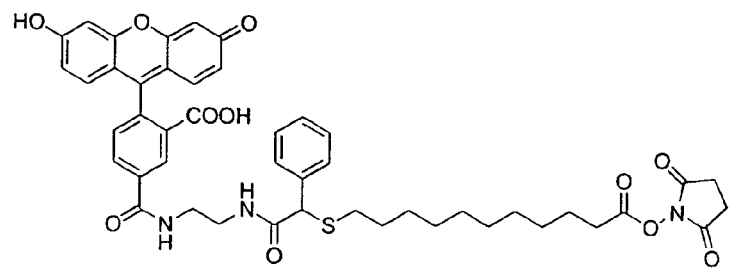
Figure 6H:
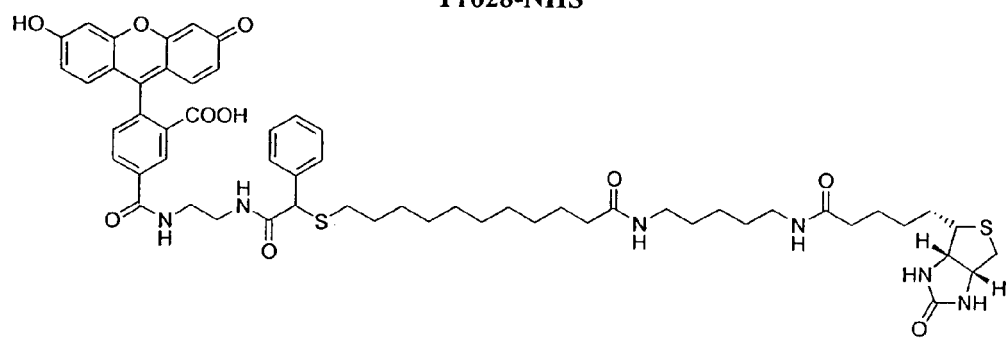
Figure 6H:
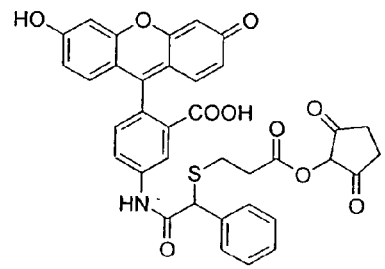
Figure 6H:
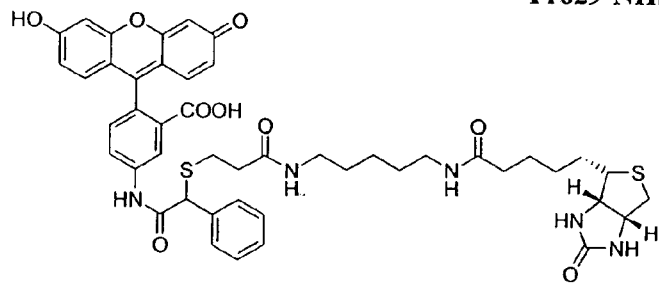
Figure 6I:
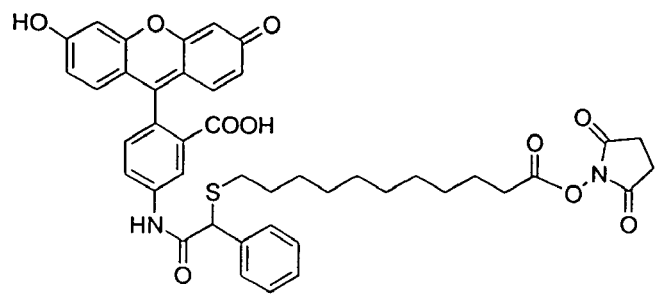
Figure 6I:
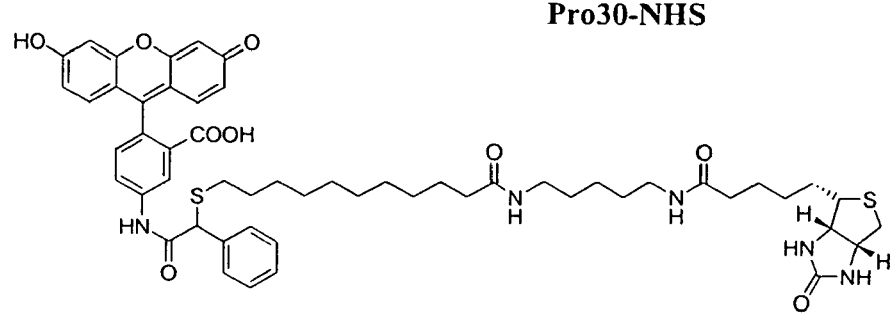
Figure 6I:
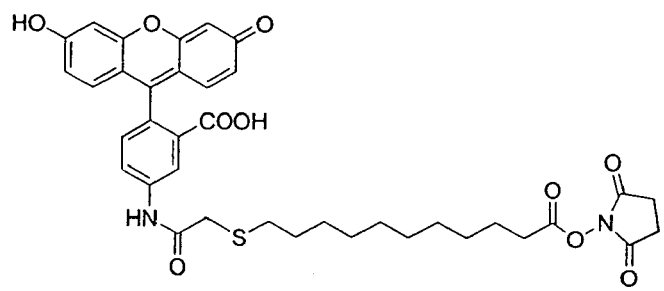
Figure 6I:
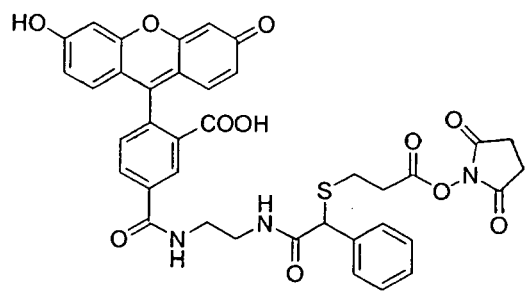
Figure 6J:
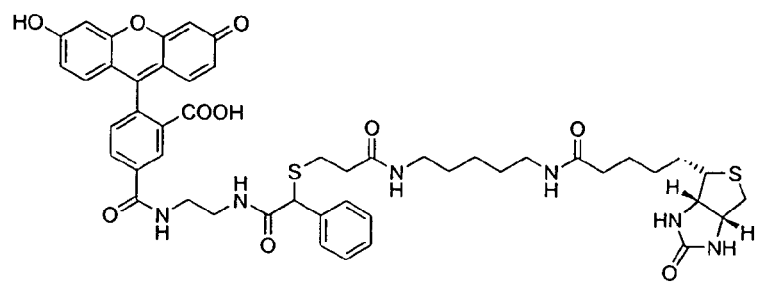
Figure 6J:
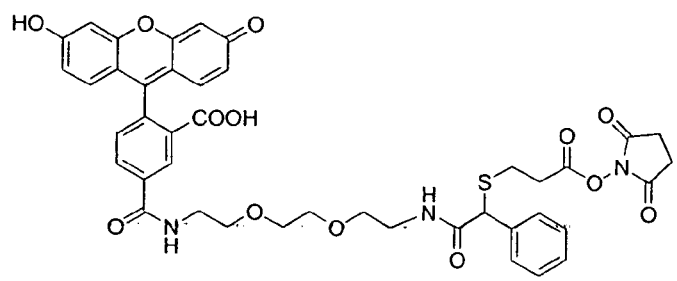
Figure 6J:
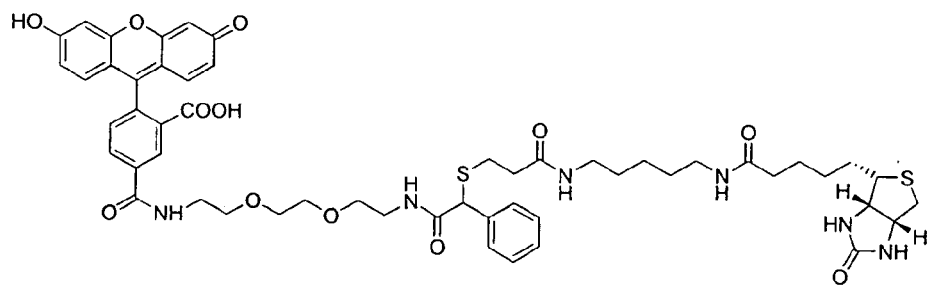
Figure 7A:
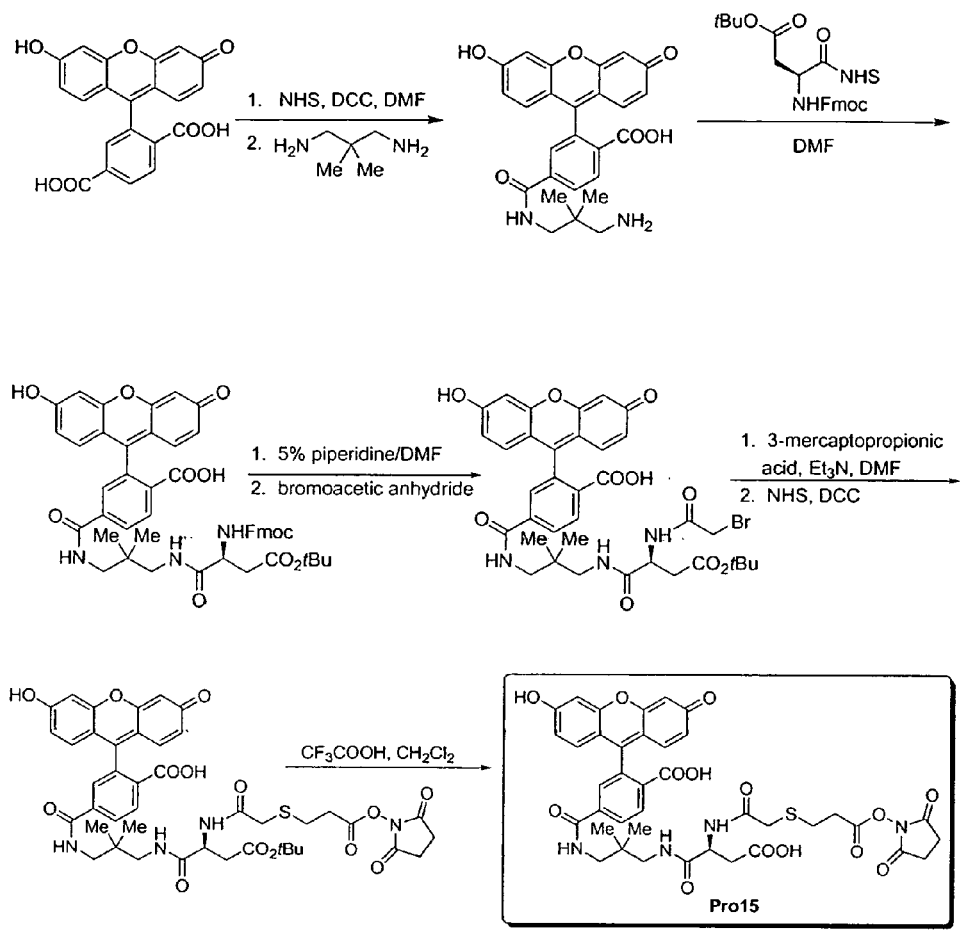
FIGS. 7A–D illustrate the chemistries of synthesis of the tag moieties illustrated in FIG. 6.
Figure 7B:
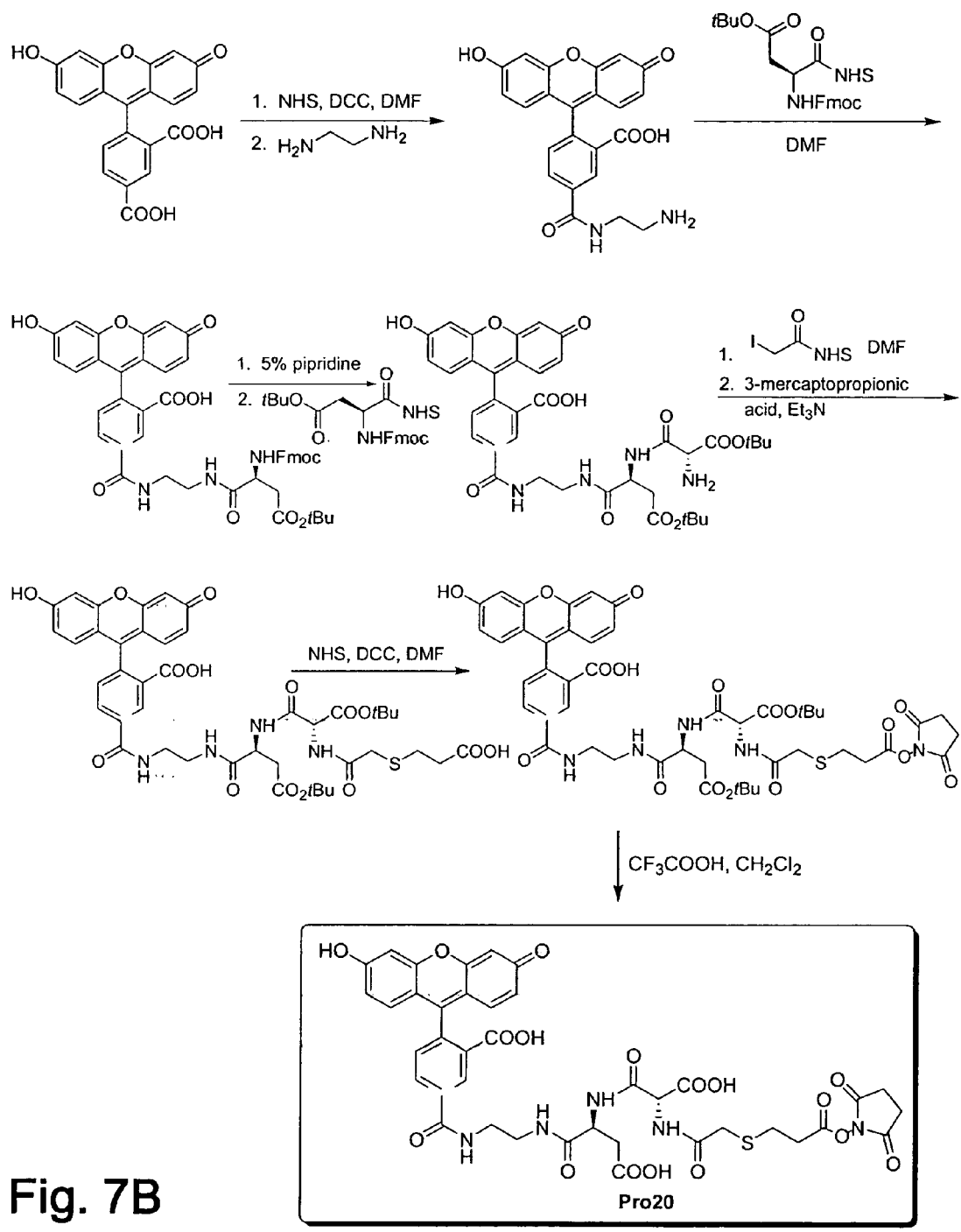
Figure 7C:
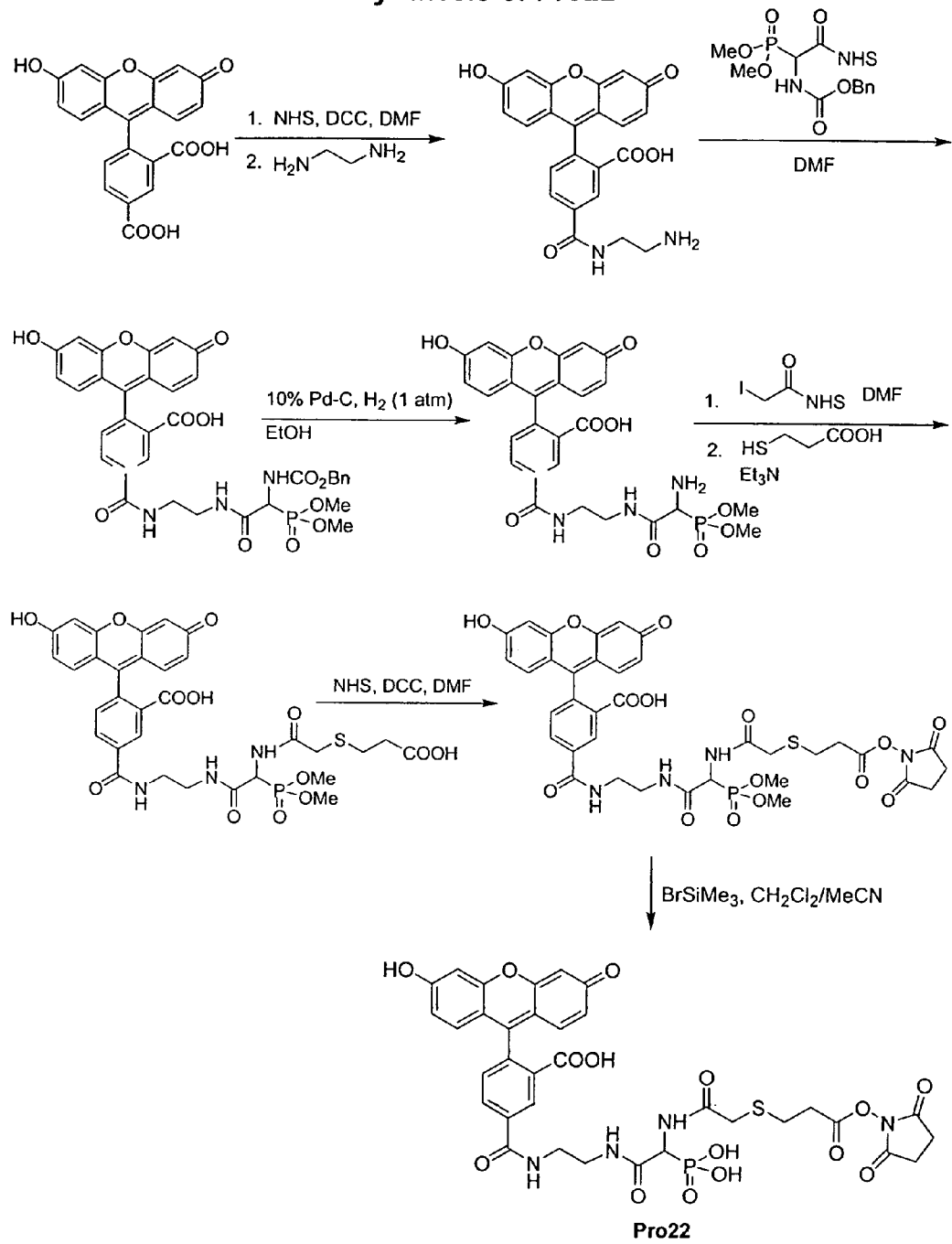
Figure 7D:
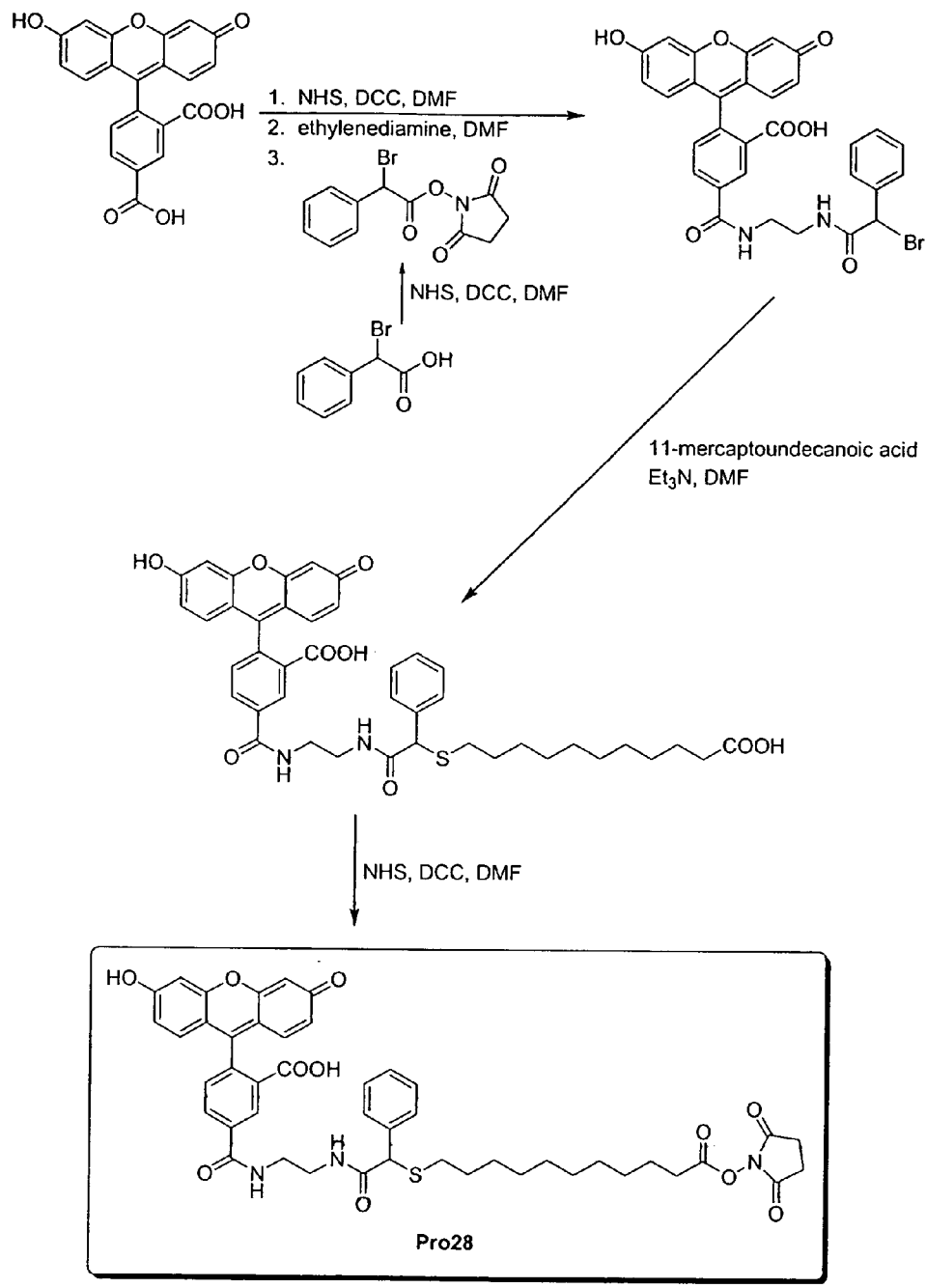

Reagents used in the methods of the invention are synthesized using conventional chemistries well known to those of ordinary skill in the art. The following references provide guidance for synthesizing reagents of the invention: International patent publications WO 00/66607; WO 01/83502; WO 02/95356; WO 03/06947; and U.S. Pat. Nos. 6,322,980 and 6,514,700. More particularly, FIG. 5SA summarizes a methodology for conjugation of a tag to an antibody or other binding agent with a free amino group, and the reaction of the resulting conjugate with singlet oxygen to produce a sulfmic acid moiety as the released tag. FIG. 5B outlines the chemistry of synthesis of FAM-derived tag reagents. FIGS. 6 A–J show several tag reagents, most of which utilize 5- or 6-carboxyfluorescein (FAM) as starting material. Methods for preparation of these tag molecules are as follows.

1. Preparation of Pro2, Pro4, and Pro6 through Pro13

A five-step procedure is used for the preparation of the carboxyfluorescein-derived tag moieties, namely, Pro2, Pro4, Pro6, Pro7, Pro8, Pro9, Pro10, Pro11, Pro12, and Pro13first step involves the reaction of a 5- or 6-FAM with N-hydroxysuccinimide (NHS) and 1,3-dicylcohexylcarbodiimide (DCC) in DMF (dimethylformnamide) to give the corresponding ester, which was then treated with a variety of diamines to yield the desired amide, compound 1. Treatment of compound 1 with N-succinimidyl iodoacetate provided the expected iodoacetamide derivative, which was not isolated but was further reacted with 3-mercaptopropionic acid in the presence of triethylamine. Finally, the resulting fl-thioacid (compound 2) was converted, as described above, to its NHS ester. The various tag moieties were synthesized starting with 5- or 6-FAM, and one of various diamines. The regioisomer of FAM and the chemical entity of "X" within the diamine are indicated in the table below for each of the tag moieties synthesized. Clearly, the diamine, X, can have a wide range of additional forms, as described above in the discussion of the mobility modifier moiety.

| Tag moiety | FAM | X |
|---|---|---|
| Pro2 | 5-FAM | C(CH$_3$)$_2$ |
| Pro4 | 5-FAM | no carbon |
| Pro6 | 5-FAM | (CH$_2$)$_8$ |
| Pro7 | 5-FAM | CH$_2$OCH$_2$CH$_2$OCH$_2$ |
| Pro8 | 5-FAM | CH$_2$CH$_2$OCH$_2$CH$_2$OCH$_2$CH$_2$OCH$_2$CH$_2$ |
| Pro9 | 5-FAM | 1,4-phenyl |
| Pro10 | 6-FAM | C(CH$_3$)$_2$ |
| Pro11 | 6-FAM | no carbon |
| Pro12 | 6-FAM | CH$_2$OCH$_2$CH$_2$OCH$_2$ |
| Pro13 | 6-FAM | CH$_2$CH$_2$OCH$_2$CH$_2$OCH$_2$CH$_2$OCH$_2$CH$_2$ |

Synthesis of compound 1

To a stirred solution of 5- or 6-carboxyfluorescein (0.5 mmol) in dry DMF (5 mL) were added N-hydroxysuccinimide (1.1 equiv.) and 1,3-dicylcohexylcarbodiimide (1.1 equiv.). After about 10 minutes, a white solid (dicyclohexylurea) started forming. The reaction mixture was stirred under nitrogen at room temperature overnight. TLC (thin layer chromatography; 9:1 CH$_2$Cl$_2$-MeOH) indicated complete disappearance of the starting material.

The supernatant from the above mixture was added dropwise to a stirred solution of diamine (2–5 equiv.) in DMF (10 mL). As evident from TLC (40:9:1 CH$_2$Cl$_2$—MeOH—H$_2$O), the reaction was complete instantaneously. The solvent was removed under reduced pressure. Flash chromatography of the resulting residue on latrobeads silica provided the desired amine (compound 1) in 58–89% yield. The $^1$H NMR (300 MHz, DMSOd6) of compound 1 was in agreement with the assigned structure.

Synthesis of compound 2

To the amine (compound 1) (0.3 mmol) were sequentially added dry DMF (10 mL) and N-succinimidyl iodoacetate (1.1 equiv.). The resulting mixture was stirred at room temperature until a clear solution was obtained. TLC (40:9:1 CH$_2$Cl$_2$—MeOH—H$_2$O) revealed completion of the reaction.

The above reaction solution was then treated with triethylamine (1.2 equiv.) and 3-mercaptopropionic acid (3.2 equiv.). The mixture was stirred at room temperature overnight. Removal of the solvent under reduced pressure followed by flash chromatography afforded the β-thioacid (compound 2) in 62–91% yield. The structure of compound 2 was assigned on the basis of its $^1$NMR (300 MHz, DMSO-d$_6$).

Synthesis of Pro2, Pro4. and Pro6 through Pro13

To a stirred solution of the -thioacid (compound 2) (0.05 mmol) in dry DMF (2 mL) were added N-hydroxysuccinimide (1.5 equiv.) and 1,3-dicylcohexylcarbodiimide (1.5 equiv.). The mixture was stirred at room temperature under nitrogen for 24–48 h (until all of the starting material had reacted). The reaction mixture was concentrated under reduced pressure and then purified by flash chromatography to give the target molecule in 41–92% yield.

2. Preparation of Pro1

To a stirred solution of 5-iodoacetamidofluorescein (compound 4) (24 mg, 0.047 mmol) in dry DMF (2 mL) were added triethylamine (8 μL, 0.057 mmol) and 3-mercaptopropionic acid (5 μL, 0.057 mmol). The resulting solution was stirred at room temperature for 1.5 h. TLC (40:9:1 CH$_2$Cl$_2$—MeOH—H$_2$O) indicated completion of the reaction. Subsequently, N-hydroxysuccinimide (9 mg, 0.078 mmol) and 1,3-dicylcohexylcarbodiimide (18 mg, 0.087 mmol) were added. The reaction mixture was stirred at room temperature under nitrogen for 19 h at which time TLC showed complete disappearance of the starting material. Removal of the solvent under reduced pressure and subsequent flash chromatography using 25:1 and 15:1 CH$_2$Cl$_2$—MeOH as eluant afforded Pro1 (23 mg, 83%).

3. Preparation of Pro3

To a stirred solution of 6-iodoacetamidofluorescein (compound 5) (26 mg, 0.050 mmol) in dry DMF (2 mL) were added triethylamine (8 μL, 0.057 mmol) and 3-mercaptopropionic acid (5 μL, 0.057 mmol). The resulting solution was stirred at room temperature for 1.5 h. TLC (40:9:1 CH$_2$Cl$_2$—MeOH—H$_2$O) indicated completion of the reaction. Subsequently, N-hydroxysuccinimide (11 mg, 0.096 mmol) and 1,3-dicylcohexylcarbodiimide (18 mg, 0.087 mmol) were added. The reaction mixture was stirred at room temperature under nitrogen for 19 h at which time TLC showed complete disappearance of the starting material. Removal of the solvent under reduced pressure and subsequent flash chromatography using 30:1 and 20:1 CH$_2$Cl$_2$—MeOH as eluant provided Pro3 (18 mg, 61%).

4. Synthesis of Pro5

To a stirred solution of 5-(bromomethyl)fluorescein (compound 6) (40 mg, 0.095 mmol) in dry DMF (5 mL) were added triethylamine (15 liL, 0.108 mmol) and 3-mercaptopropionic acid (10 μL, 0.115 mmol). The resulting solution was stirred at room temperature for 2 days. TLC (40:9:1 CH$_2$Cl$_2$—MeOH—H$_2$O) indicated completion of the reaction. The reaction solution was evaporated under reduced pressure. Finally, flash chromatography employing 30:1 and 25:1 CH$_2$Cl$_2$—MeOH as eluant provided the )3-thioacid (compound 7) (28 mg, 66%).

To a solution of the acid (compound 7) (27 mg, 0.060 nmmol) in dry DMF (2 mL) were added N-hydroxysuccinimide (11 mg, 0.096 mmol) and 1,3-dicylcohexylcarbodiimide (20 mg, 0.097 mmol). The reaction mixture was stirred at room temperature under nitrogen for 2 days at which time TLC (9:1 CH$_2$Cl$_2$—MeOH) showed complete disappearance of the starting material. Removal of the solvent under reduced pressure and subsequent flash chromatography with 30:1 CH$_2$Cl$_2$—MeOH afforded Pro5 (24 mg, 73%).

5. Synthesis of Pro14

To 5-aminoacetamidofluorescein (compound 8) (49 mg, 0.121 mmol) were sequentially added dry DMF (4 mL) and N-succinimidyl iodoacetate (52 mg, 0.184). A clear solution resulted and TLC (40:9:1 CH$_2$Cl$_2$—MeOH—H$_2$O) indicated complete disappearance of the starting material.

The above reaction solution was then treated with triethylamine (30 μL, 0.215 mmol) and 3-mercaptopropionic acid (30 μL, 0.344 mmol). The resulting mixture was stirred for 2 h. Removal of the solvent under reduced pressure followed by flash chromatography using 20:1 and 15:1 CH$_2$Cl$_2$—MeOH as eluant gave the β-thioacid (compound 9) (41 mg, 62%). The structural assignment was made on the basis of $^1$NMR (300 MHz, DMSO-d6).

To a stirred solution of compound 9 (22 mg, 0.04 mmol) in dry DMF (2 mL) were added N-hydroxysuccinimide (9 mg, 0.078 mmol) and 1,3-dicylcohexylcarbodiimide (16 mg, 0.078 mmol). The resulting solution was stirred at room temperature under nitrogen for about 24 h. The reaction mixture was concentrated under reduced pressure and the residue purified by flash chromatography using 30:1 and 20:1 CH$_2$Cl$_2$—MeOH as eluant to give Pro14 (18 mg, 70%).

6. Synthesis of Pro15, Pro20, Pro22, and Pro28

The synthesis schemes for producing NHS esters of tags Pro15, Pro20, Pro22, and Pro28 are shown in FIGS. 7 A–D, respectively. All of the reagent and reaction conditions are conventional in the art and proceed similarly as the reactions described above.

Conjugation of Tag Molecules to Antibodies

Two different approaches for conjugation are generally employed. The first involves the direct attachment of tag molecules to the antibody, and the second approach involves attachment of tag molecules to dextran, which is then attached to the antibody. The second approach provides means for signal amplification, generating a tagged antibody reagent containing multiple tag molecules, which may all be released by a single sensitizer molecule.

1. Direct Conjugation of Pro1 Tag Molecules to Antibodies

Tag molecules are synthesized with an NHS ester end that reacts with primary amines of the antibody to form a stable amide linkage, resulting in a random attachment of tag molecules over the surface of the antibody. Previously conjugated tag-antibodies have demonstrated that modification with up to 6 to 12 NHS ester-containing molecules per antibody molecule typically results in no decrease in antigen binding activity. Even higher ratios of NHS ester to antibody are possible with only slight loss of activity.

Protocol

1. Purified mouse monoclonal antibody 9E10 (which recognizes the amino acid sequence EQKLISEEDL, specific for c-myc, from Roche Diagnostics, Indianapolis, IN) is diluted to 2 mg/mL in 1× PBS (0.1 M sodium phosphate, 0.15 M NaCl, pH 7.2).
2. NHS ester-containing Pro1 molecules are dissolved in DMF (dimethylformamide) to a final concentration between 10 to 20 rmols/lL DMF.
3. 500 µL of diluted 9E10 antibody (6.5 nmol) is mixed with either 1, 5, 25, or 50 µL of Pro1 tag reagent (14, 68, 340, and 680 nmols respectively). (See FIG. 6A.)
4. The solution is allowed to react for 2 hours on ice in the dark.
5. The Pro1-conjugated mouse anti-c-myc is purified by dialysis against 0.1×PBS (10 mM sodium phosphate, 15 mM NaCl, pH 7.2) for 20 hours at 4° C.

2. Conjugation of Pro-dextran to antibodies

In this second method, tag molecules are first attached to amine-containing dextran via an amide linkage essentially as described above. Polyclonal and some monoclonal antibodies contain carbohydrates in the Fc portion of the antibody. These polysaccharides can be periodate-oxidized to form reactive aldehyde residues. The aminodextran-containing tag is then conjugated to the aldehyde residues of the oxidized antibodies through the formation of a Schiff base. This linkage is further stabilized by reduction to a secondary amine linkage with sodium cyanoborohydride.

The extremely large size of the aminodextran (molecular weight of 500,000) containing 50 to 500 available amino-groups for conjugation to tag molecules allows for a significant increase in the number of tags linked to an antibody, providing for signal amplification. Since the dextran is coupled through a carbohydrate on the Fc portion of the antibody, it is sufficiently removed from the antigen-binding site such that it will not comprise binding activity.

Protocol for conjugation of Pro1 tag molecules to aminodextran

1. Amino-dextran (500,000 mw with 500 amines/mole dextran) is dissolved in 90% DMF to a final concentration of 2 mg/nl (2 nmol amine/µL).
2. NHS ester containing tag molecules are dissolved in DMF (dimethylformamide) to a final concentration between 10 to 20 nmols/µL DMF.
3. 500 µL of amino-dextran (1000 nmol of amine) is mixed with either 500, 1000, or 2000 nmol Pro1 tag reagent.
4. The solution is allowed to react for 2 hours on ice in the dark.
5. The tag-conjugated amino-dextran is purified by dialysis against 0.1× PBS (10 mM sodium phosphate, 15 mM NaCl, pH 7.2) for 20 hours at 4° C.
6. Precipitate is removed by centrifugation at 14,000×g for 5 minutes.

Protocol for oxidation of antibodies with sodium periodate 1. 500 µL (2.8 nmol) of purified mouse monoclonal antibody 9E10 (which recognizes the amino acid sequence EQKLISEEDL, specific for c-myc, from Roche Diagnostics, Indianapolis, IN) is oxidized in the presence of 10 mM sodium periodate (Aldrich).
2. The solution is allowed to react for 30 minutes at room temperature in the dark.
3. Ethylene glycol is added to a final concentration of 100 mM and allowed to incubate for 10 minutes at room temperature. p1 4. The oxidized antibody is then purified by dialysis against 0.1× PBS (10 mM sodium phosphate, 15 mM NaCl, pH 7.2) for 2 hours at 4° C.

Protocol for conjugation of periodate-oxidized antibody to Pro I-conjugated aminodextran 1. 54 µL (300 pmol) of oxidized mouse monoclonal antibody 9E10 is mixed with 300 pmol of Pro 1-conjugated aminodextran in the presence of 200 mM sodium carbonate, pH 9.5.
2. The solution is allowed to react for 2 hours at room temperature in the dark.
3. Sodium cyanoborohydride (made fresh in 1 N NaOH) is added to a final concentration of 50 mM and allowed to react for 30 minutes at room temperature.
4. Unreacted aldehydes are blocked by the addition of 50 mM ethanolamine, pH 9.6 and allowed to react for 30 minutes at room temperature.
5. The Pro1-conjugated mouse anti-c-myc is then purified by dialysis against 0.1× PBS (10 mM sodium phosphate, 15 mM NaCl, pH 7.2) for 20 hours at 4° C.

Conjuiation of Photosensitizer Molecules to Binding Agents

Sensitzer molecules can be conjugated to an antibody by various methods and configurations. For example, an activated sensitizer, such as e.g., methyene blue or phthalocyanine, activated with e.g., NHS ester, aldehyde, or sulfonyl chloride, can be reacted with the amino groups in antibodies. These conjugates can then be used directly in various assays. Also, multiple activated sensitizer molecules can be coupled with antibody, e.g. by using an aminodextran-sensitizer conjugate containing 20–200 sensitizers and 200–500 amino-groups, coupled to periodate-oxidized antibody molecules, generating an antibody-dextran-sensitizer conjugate. Protocols for generating these reagents are as described above for the tag-antibody reagents.

For the present example, the sensitizer conjugates will be generated using purified mouse monoclonal antibody 12CA5, which recognizes the amino acid sequence YPYDVPDYA, specific for hemagglutinin, from Roche Diagnostics, Indianapolis, IN, coupled to methyene blue activated with NHS ester, to generate methyene blue-conjugated mouse anti-HA.

Sources of Materials Used in Examples
Antibodies:

| | | |
|---|---|---|
| Her-1 | EGFR. 1 | Labvision, Ab-3 |
| | H11 | Labvision, Ab-5 |
| | H9B4 | Labvision, Ab-15 |
| Her-2 | N12 | Labvision, Ab-4 |
| | N29 | Labvision, Ab-7 |
| | 3B5 | Labvision, Ab-15 |
| Her-3 | H3.90.6 | Labvision, Ab-4 |
| | SGP1 | Labvision, Ab-8 |
| | Rabbit Ab | Labvision, Ab-11 |
| Her-4 | H4.77.16 | Labvision, Ab-1 |
| | HFK-1 | Labvision, Ab-4 |
| | Mouse MAb | Santa Cruz, C-7 |
| | Rabbit Ab | Santa Cruz, C-18 |
| Phospho-Tyr | PY20 | BD Biosciences |
| | PT-100 | Cell Signaling |
| | PY69 | BD Biosciences |
| Anti-Her-1(Y1068) | 1H12 | Cell Signaling |
| Anti-Her-2(Y1248) | PN2A | Labvision, Ab-18 |

Cell Lines: All cell lines were purchased from ATCC.

Human Tissues: All human snap-frozen tissue samples were purchased from either William Bainbridge Genome Foundation (Seattle, WA) or Bio Research Support (Boca Raton, FL) and were approved by Institutional Research Board (IRB) at the supplier.

EXAMPLE 1

Assay for Monitoring $GABA_BR1/GABA_BR2$ Hetero-oligomerization

The $\gamma$-aminobutyric acid$_B$ $(GABA)_B$ receptor, a G-protein coupled receptor (GPCR), mediates stimulation of high-affinity GTPase activity in brain membranes by GABA to regulate potassium and calcium channels. The active form of this receptor, localized to the cell surface, has been shown to be a hetero-oligomer comprising the two receptors $GABA_BR1$ and $GABA_BR2$, which are both class III GPCRs and share 35% sequence identity (Jones, et al., 1998, Kaupmann, et al., 1998, White, et al., 1998, Milligan, 2001).

$GABA_B$ receptor hetero-oligomerization can be monitored using the methods of the present invention. First, epitope-tagged $GABA_BR1$ and $GABA_BR2$ receptors are generated and transfected into HEK293T cells as described by White, et al. (1998).

Protocol for transfection of HEK293T cells with $GABA_BR1$ and $GABA_BR2$ coding sequence
1. cDNA encoding a Myc epitope (used with monoclonal antibody 9E10) is fused in-frame to the 5' end of the cDNA encoding $GABA_BR1$, and the native signal sequence is removed and replaced with that of CD33.
2. cDNA encoding the HA epitope (used with monoclonal antibody 12CA5) is fused in-frame to the 5' end of cDNA encoding $GABA_BR2$, and the native signal sequence is removed and replaced with that of T8.
3. HEK293T cells are maintained in DMEM medium containing 10% fetal calf serum and 2 mM glutamine. The cells are grown to 60–80% confluency in 60 mm dishes, and transfected with 1.5 µg of each GABAB cDNA chimera using 10 µL lipofectamine reagent (Life Technologies). Cells are collected 48–72 hours after transfection.

Protocol for monitoring oligomerization
1. $GABA_BR1$ and $GABA_BR2$-transfected HEK293T cells ($10^5$ cells) in 50 mM Tris-HCl, pH 7.4, are combined with 5–20 nM of each of Prol-conjugated mouse anti-c-myc antibody and methyene blue-conjugated mouse anti-HA antibody in the dark. Three control samples are generated that omit one of the cells, the anti-c-myc antibody, or the anti-HA antibody.
2. The mixture is incubated for 30 min. at 37° C. in the dark, to allow binding.
3. Unbound antibody is removed by centriftigation of the sample and removal of the supernatant, followed by resuspension of the cells in the pellet with an exchange buffer comprising 50 mM Tris-HCI, pH 7.4, and ROX T8 standard (from PE Biosystems), diluted 1:2000 in the buffer.
4. The sample is then irradiated for 5 minutes at 680 nm using a light emitting diode to activate the sensitizer for cleavage.
5. The sample is centrifuiged again, and the supernatant is collected, which contains any tag molecules released during the assay.
6. Released tags are separated by capillary electrophoresis either on an ABI3100 capillary electrophoresis apparatus or on an ACLARA plastic LabCard™ device (ACLARA BioSciences, Inc. Mountain View, Calif.). Separation conditions of the released tags on an AB13100 are as follows: 50 µm capillary, 47 cm long and 36 cm end-to-detection; separation buffer, POP-4; injection 80 s at 3.0 kV; separation Voltage, 15 kV.

EXAMPLE 2

Analysis of Cell Lysates for Her-2 Heterodimerization and Receptor Phosphorylation In this example, Her1–Her2 and Her2–Her3 heterodimers and phosphorylation states are measured in cell lysates from several cell lines after treatment with various concentrations of epidermal growth factor (EGF) and heregulin (HRG). Measurements are made using three binding compounds and a cleaving probe as described below.

Sample Preparalion:
1. Serum-starve breast cancer cell line culture overnight before use.
2. Stimulate cell lines with EGF and/or HRG in culture media for 10 minutes at 37° C.
   Exemplary doses of EGF/HRG are 0, 0.032,0.16, 0.8,4, 20,100 nM for all cell lines (e.g. MCF-7, T47D, SKBR-3) except BT20 for which the maximal dose is increased to 500 nM because saturation is not achieved with 100 nM EGF.
3. Aspirate culture media, transfer onto ice, and add lysis buffer to lyse cells in situ.
4. Scrape and transfer lysate to microfuge tube. Incubate on ice for 30 min. Microfuge at 14,000 rpm, 4° C., for 10 min. (Centrifugation is optional.)
5. Collect supernatants as lysates and aliquot for storage at -80° C. until use.

Figure 9A:
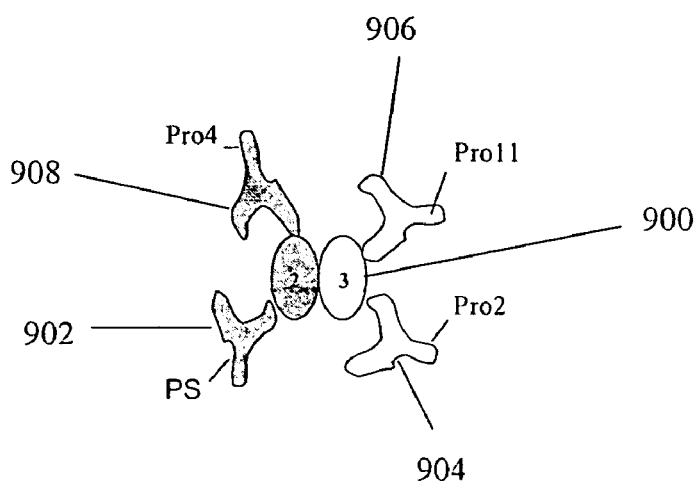
FIGS. 9A–9E illustrate data from assays on cell lysates for receptor heterodimers using a method of the invention.

Assay:
Assay design: As illustrated diagrammatically in FIG. 9A, Her2–Her3 heterodimers (900) are quantified ratiometrically based on the binding of cleaving probe (902) and binding compounds (904), (906), and (908). A photosensitizer indicated by "PS" is attached to cleaving probe (902) via an avidin-biotin linkage, and binding compounds (904), (906), and (908) are labeled with molecular tags Pro14, Pro10, and Pro11, respectively. Binding compound (904) is specific for a phosphorylation site on Her3.

The total assay volume is 40 ul. The lysate volume is adjusted to 30 ul with lysis buffer. The antibodies are diluted in lysis buffer up to 10 ul. Typically ~5000 to15000 cell-equivalent of lysates is used per reaction. The detection limit is ~1000 cell-equivalent of lysates.

Procedure: Final concentrations of pre-mixed binding compounds (i.e. molecular tag- or biotin-antibody conjugates) in reaction:

Pro4_anti-Her-2: 0.1 ug/ml
Pro10_Abil anti-Her-1: 0.05–0.1 ug/ml
Pro11_anti-Her-3: 0.1 ug/ml
Pro2_PT100 anti-phospho-Tyr: 0.1 ug/ml
Biotin_anti-Her-2: 1–2 ug/ml 1. To assay 96-well, add 10 ul antibody mix to 30 ul lysate and incubate for 1 hour at RT.
2. Add 2 ul streptavidin-derivatized cleaving probe (final 2 ug/well) to assay well and incubate for 45 min.
3. Add 150 ul of PBS with 1% BSA to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using an AB13100 CE instrument with a 22 cm capillary (injection conditions: 5 kV, 75 sec, 30° C.; run conditions: 600 sec, 30° C.).

Assay buffers are as follows:

| Lysis Buffer (made fresh and stored on ice) | | |
|---|---|---|
| Final | ul | Stock |
| 1% Triton X-100 | 1000 | 10% |
| 20 mM Tris-HCl (pH 7.5) | 200 | 1 M |
| 100 mM NaCl | 200 | 5 M |
| 50 mM NaF | 500 | 1 M |
| 50 mM Na beta-glycerophosphate | 1000 | 0.5 M |
| 1 mM $Na_3VO_4$ | 100 | 0.1 M |
| 5 mM EDTA | 100 | 0.5 M |
| 10 ug/ml pepstatin | 100 | 1 mg/ml |
| 1 tablet (per 10 ml) Roche Complete protease inhibitor (#1836170) | N/A | N/A |
| Water | 6500 | N/A |
| | 10 ml | Total |

| Wash buffer (stored at 4° C.) | | |
|---|---|---|
| Final | ml | Stock |
| 1% NP-40 | 50 | 10% |
| 1x PBS | 50 | 10x |
| 150 mM NaCl | 15 | 5 M |
| 5 mM EDTA | 5 | 0.5 M |
| Water | 380 | N/A |
| | 500 ml | Total |

| Illumination buffer: | | |
|---|---|---|
| Final | ul | Stock |
| 0.005x PBS | 50 | 1x |
| CE std | 3 | 100x |
| 10 mM Tris-HCl (pH 8.0) | | 0.1 M |
| 10 pM A160 | | 1 nM |
| 10 pM A315 | | 1 nM |
| 10 pM HABA | | 1 nM |
| Water | | 10,000 N/A |
| | 10 ml Total | |

Data Analysis:
1. Normalize relative fluorescence units (RFU) signal of each molecular tag against CE reference standard A3 15.
2. Subtract RFU of "no lysate" background control from corresponding molecular tag signals.
3. Report heterodimerization for Her-1 or Her-3 as the corresponding RFU ratiometric to RFU from Pro4_anti-Her-2 from assay wells using biotin-anti-Her-2.
4. Report receptor phosphorylation for Her-1,2,3 as RFU from Pro2_PT100 anti-phospho-Tyr ratiometric to RFU from Pro4_anti-Her-2 from assay wells using biotin-anti-Her-2.

Figure 9B:
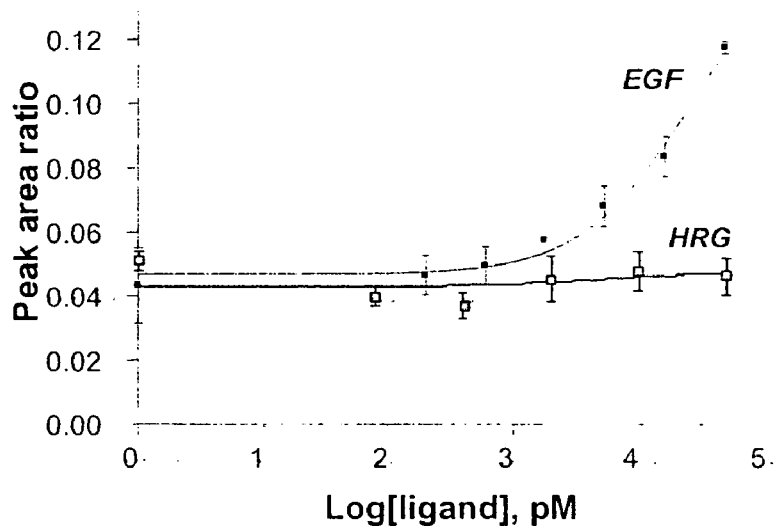
Figure 9C:
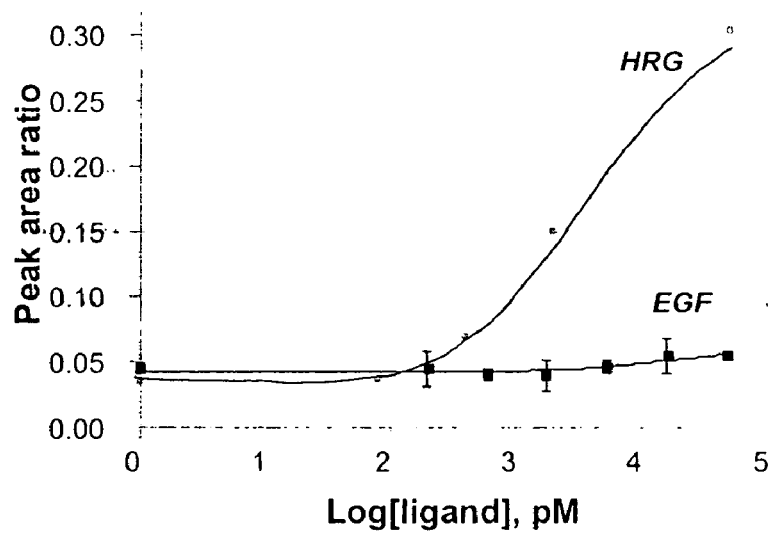
Figure 9D:
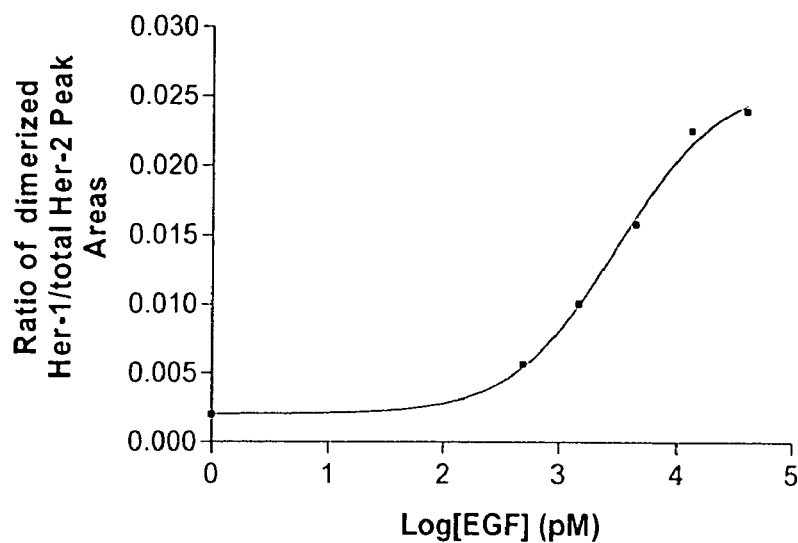
Figure 9E:
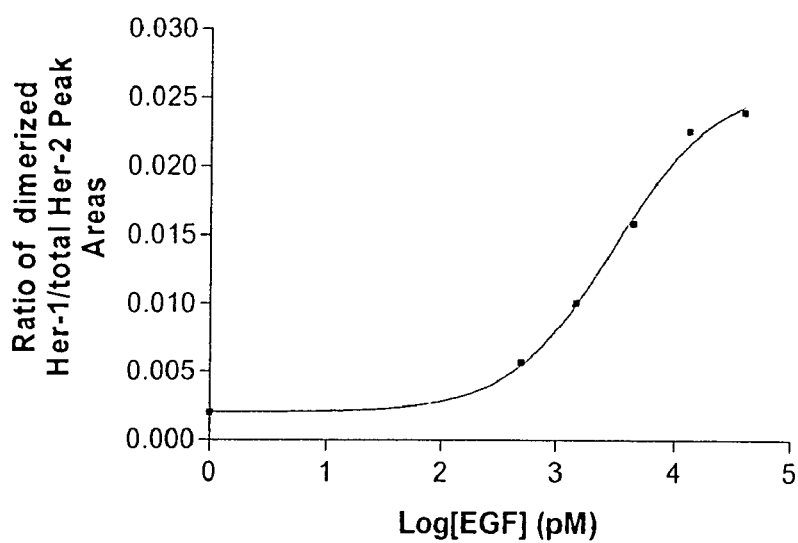

Results of the assays are illustrated in FIGS. 9B–9H. FIG. 9B shows the quantity of Her1–Her2 heterodimers increases on MCF-7 cells with increasing concentrations of EGF, while the quantity of the same dimer show essentially no change with increasing concentrations of HRG. FIG. 9C shows the opposite result for Her2–Her3 heterodimers. That is, the quantity of Her2–Her3 heterodimers increases on MCF-7 cells with increasing concentrations of HRG, while the quantity of the same dimer show essentially no change with increasing concentrations of EGF. FIGS. 9D and 9E show the quantity of Her1–Her2 heterodimers increases on SKPR-3 cells and BT-20 cells, respectively, with increasing concentrations of EGF.

EXAMPLE 3

Analysis of Tissue Lysates for Her2 Heterodimerization and Receptor Phosphorylation In this example, Her1–Her2 and Her2–Her3 heterodimers and phosphorylation states are measured in tissue lysates from human breast cancer specimens.

Sample Preparation:
1. Snap frozen tissues are mechanically disrupted at the frozen state by cutting.
2. Transfer tissues to microfuge tube and add 3× tissue volumes of lysis buffer (from appendix I) followed by vortexing to disperse tissues in buffer.
3. Incubate on ice for 30 min with intermittent vortexing to mix.
4. Centrifuge at 14,000 rpm, 4° C., for 20 min.
5. Collect supernatants as lysates and determine total protein concentration with BCA assay (Pierce) using a small aliquot.
6. Aliquot the rest for storage at -80C until use.

Assay design:
1. The total assay volume is 40 ul.
2. The lysates are tested in serial titration series of 40, 20, 10, 5,2.5, 1.25, 0.63, 0.31 ug total-equivalents and the volume is adjusted to 30 ul with lysis buffer. Data from the titration series confirm the specificity of the dimerization or phosphorylation signals.
3. A universal antibody mix comprising all eTag-antibodies diluted in lysis buffer is used at the following concentrations.
4. Individual biotin-antibody for each receptor is added separately to the reactions.
5. Three eTag assays are conducted with each tissue lysate, each using a different biotin-antibody corresponding to specific receptor dimerization to be measured.

6. Expression level of each receptor is determined from different assay containing the biotin-antibody specific to the receptor.
7. Dimerization and phosphorylation signals are determined ratiometrically only in the assay containing the biotin-anti-Her-2.

Assay controls: MCF-10A and MCF-7 cell lines are used as qualitative negative and positive controls, respectively. Cell lines are either unstimulated or stimulated with 100 nM EGF or 100 nM HRG. Lysis buffer is included as a background control when replacing the tissue samples.

Final concentrations of pre-mixed antibodies in reactions:
Universal antibody mix:
Pro4_anti-Her-2: 0.1 ug/ml
Pro10_anti-Her-1: 0.05 ug/ml
Pro1 I_anti-Her-3: 0.1 ug/ml
Pro2_anti-phospho-Tyr: 0.01 ug/ml
Individual biotin antibody:
Biotin_anti-Her-1: 2 ug/ml
Biotin_anti-Her-2: 2 ug/ml
Biotin_anti-Her-3: 2 ug/ml Procedure:
1. Prepare antibody reaction mix by adding biotin antibody to universal antibody mix.
2. To assay 96-well, add 10 ul universal reaction mix to 30 ul lysate and incubate for 1 hour at RT.
3. Add 2 ul streptavidin-derivatized cleaving probe (final 2 ug/well) to assay well and incubate for 45 min.
4. Add 150 ul of PBS with 1% BSA to 96-well filter plate (Millipore MAGVN2250) and incubate for 1 hr at RT for blocking.
5. Empty filter plate by vacuum suction. Transfer assay reactions to filter plate and apply vacuum to empty.
6. Add 200 ul wash buffer and apply vacuum to empty. Repeat one time.
7. Add 200 ul illumination buffer and apply vacuum to empty. Repeat one time.
8. Add 30 ul illumination buffer and illuminate for 20 min.
9. Transfer 10 ul of each reaction to CE assay plate for analysis using AB13100 capillary electrophoresis instrument with a 22 cm capillary (injection conditions: 5 kV, 75 sec, 30° C.; run conditions: 600 sec, 30° C.)

Data Analysis:
1. Normalize RFU signal of each molecular tag against CE reference standard A315.
2. Determine the cut-off values of RFU (each for dimerization or phosphorylation) below which ratios are not calculated because the signals are too low to be reliable. Below the cut-off values, the RFU signals are not titratable in the series of lysate dilution tested. The values can be determined with a large set of normal tissues where dimerization and phosphorylation signals are expected to be absent or at the lowest. These values also represent the basal level of dimerization or phosphorylation on the normal tissues to which tumor tissues will be compared.
3. For the minority of normal tissues, if present, with RFU values above the cut-off, determine the individual RFU level and ratiometric readouts of Her-1 or Her-3 heterodimerization or phosphorylation peaks detected. These samples represent outliers that should be used as matched donor controls for the corresponding tumor tissue samples while scoring.
4. For all tumor samples showing titratable RFU signals, use the lowest signal of each of Her-1, Her-2, Her-3, or phosphorylation from the tissue lysate titration series as the background. Subtract this background from the molecular tag signals of the high dose lysates (e.g. 40 ug) to yield the specific RFU signals. If there is no signal dose response in the titration series, all signals (which are usually very low) are considered background and no specific signals can be used for ratiometric analysis.
5. Report heterodimerization for Her-1 or Her-3 as the corresponding specific RFU ratiometric to the specific RFU from Pro4_anti-Her-2. If no specific RFU is obtained, the dimerization is negative.
6. Report receptor phosphorylation for Her-1,2,3 as specific RFU from Pro2_anti-phospho-Tyr ratiometric to the specific RFU from Pro4_anti-Her-2. If no specific RFU is obtained, the phosphorylation is negative.

Figure 10A:
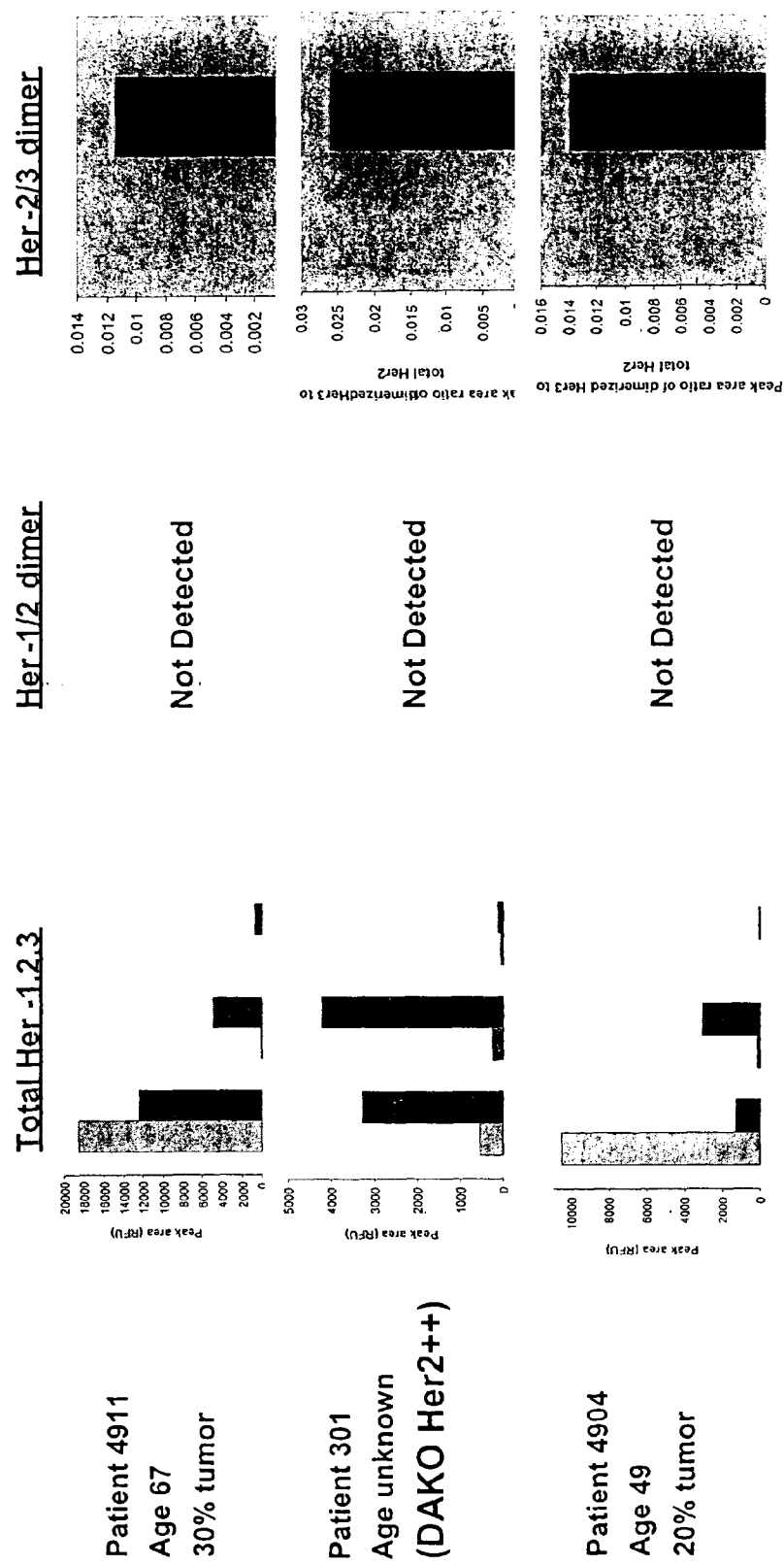
FIGS. 10A–10C illustrate data from assays on tissue samples for receptor heterodimers using a method of the invention.
Figure 10B:
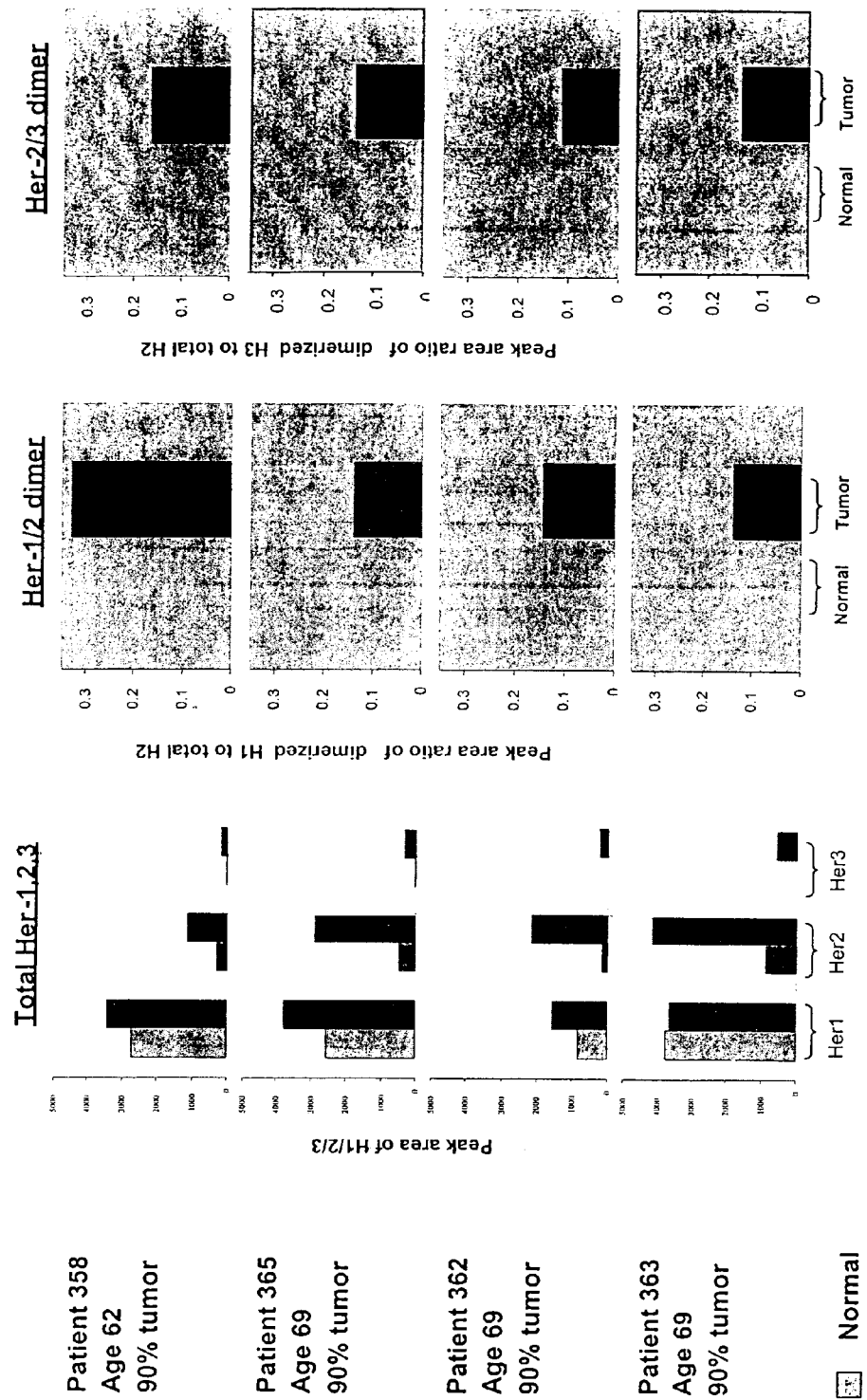
Figure 10C:
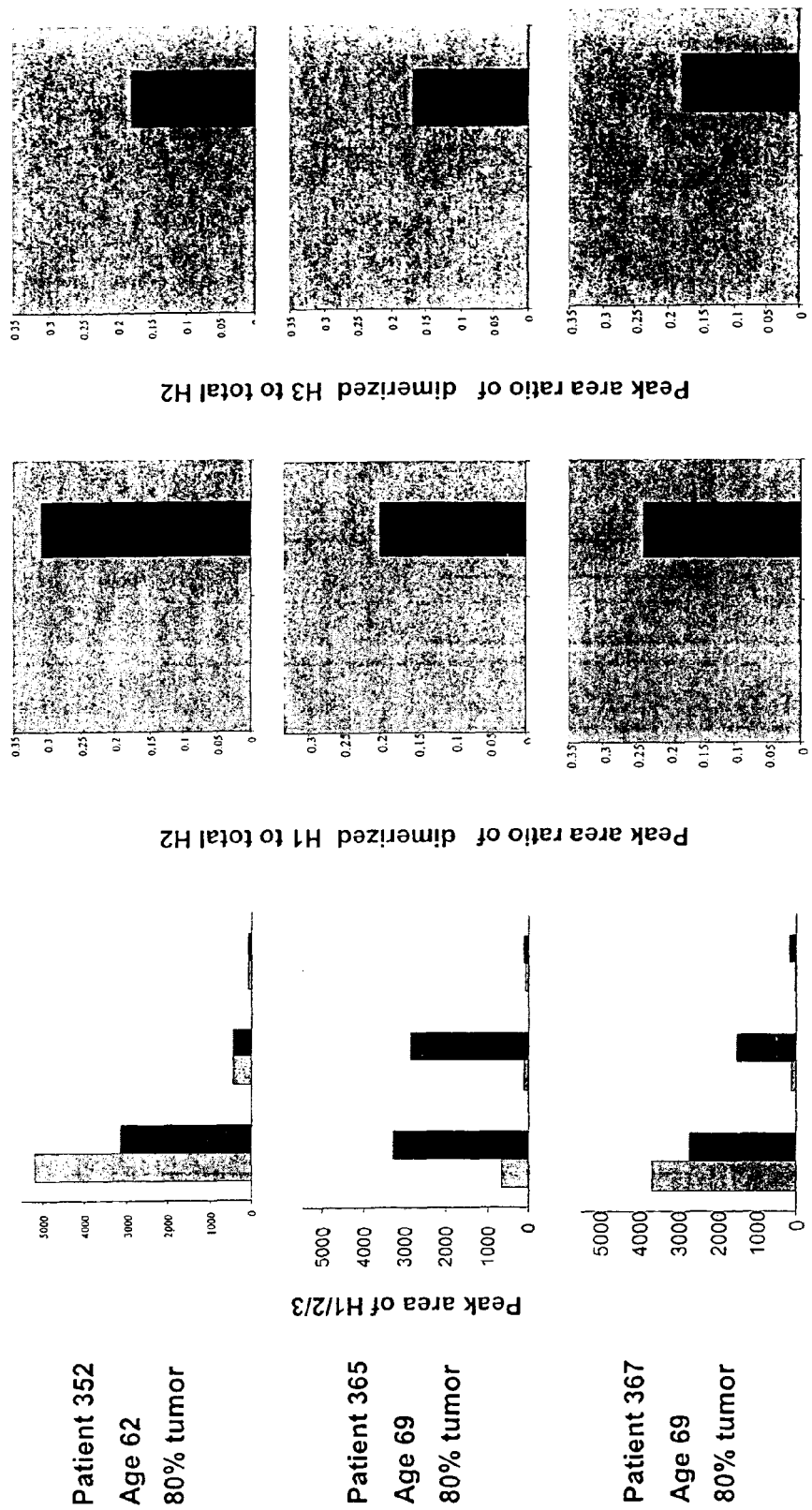

In FIGS. 10A–10C data shown are representative of multiple patients' breast tissue samples tested with assays of the invention. The clinical Her-2 status from immunohistochemistry (DAKO Herceptest) of 9 out of 10 tumor samples was negative, indicative of either undetectable Her-2 staining, or staining of less than 10% of the tumor cells, or a faint and barely perceptible staining on part of the cell membrane of more than 10% tumor cells. The assays of the invention determined the expression of Her-1, Her-2, and Her-3 on both normal and tumor tissues. The heterodimerization of Her1 and Her2 and of Her2 and Her3 was detected only in tumor tissues but not in any normal tissues.

EXAMPLE 4

Analysis of Cell Lysates for Her1 or Her2 Homodimerization and Receptor PhosDhorylation Sample preparation was carried out essentially as described in Example 2. Her1 homodimerization was induced by treating the cell lines with EGF or TGFα. For homodimerization of Her2 which does not have a ligand, unstimulated SKBR-3 or MDA-MD-453 cells that overexpress Her2 are compared to unstimulated MCF-7 cells that express a low level of Her2.

Assay design: A monoclonal antibody specific to the receptor is separately conjugated with either a molecular tag or biotin (that is then linked to a photosensitizer via an avidin bridge), so that the cleaving probe and a binding compound compete to bind to the same epitope in this example. Another binding compound is used that consists of a second anibody recognizing an overlapping epitope on the receptor, so that a ratiometric signal can be generated as a measure of homodimerization. The signal derived from the second antibody also provides a measure of the total amount of receptor in a sample. The total amount of receptor is determined in a separate assay well. Receptor phosphorylation can be quantified together with either homodimerization or total receptor amount.

Procedure: The assay volume is 40 ul and the general procedure is similar to that of Example 2. Two assay wells, A and B, are set up for each sample to quantify homodimerization and total amount of receptor separately.

For quantification of Her -Her1 homodimers: Final concentrations in antibody mix in assay well A:
Pro12_anti-Her-1: 0.05–0.1 ug/ml
Biotin_anti-Her-1: 1–2 ug/ml
Final concentrations in antibody mix in assay well B:
Pro10-anti-Her-1: 0.05–0.1 ug/ml
Pro2_anti-phospho-Tyr: 0.1 ug/ml
Biotin_anti-Her-1: 1–2 ug/ml For quantification of Her2—Her2 homodimers: Final concentrations in antibody mix in assay well A:
Pro4_anti-Her-1: 0.05–0.1 ug/ml
Biotin_anti-Her-1: 1–2 ug/ml
Final concentrations in antibody mix in assay well B:
Pro4_anti-Her-1: 0.05–0.1 ug/ml
Pro2_anti-phospho-Tyr: 0.1 ug/ml
Biotin_anti-Her-1: 1–2 ug/ml Data Analysis:
1. Normalize RFU signal of each molecular tag against CE reference standard A315.
2. Subtract RFU of "no lysate" background control from corresponding molecular tag signals.
3. Report homodimerization for Her-1 or Her-2 as the corresponding normalized RFU from assay well A as ratiometric to normalized RFU of total receptor amount from the corresponding assay well B.
4. Report receptor phosphorylation for Her-1 or Her-2 homodimer as normalized RFU from Pro2_PT100 anti-phospho-Tyr from assay well B as ratiometric to normalized RFU from total receptor amount from the same assay well B.

Figure 11A:
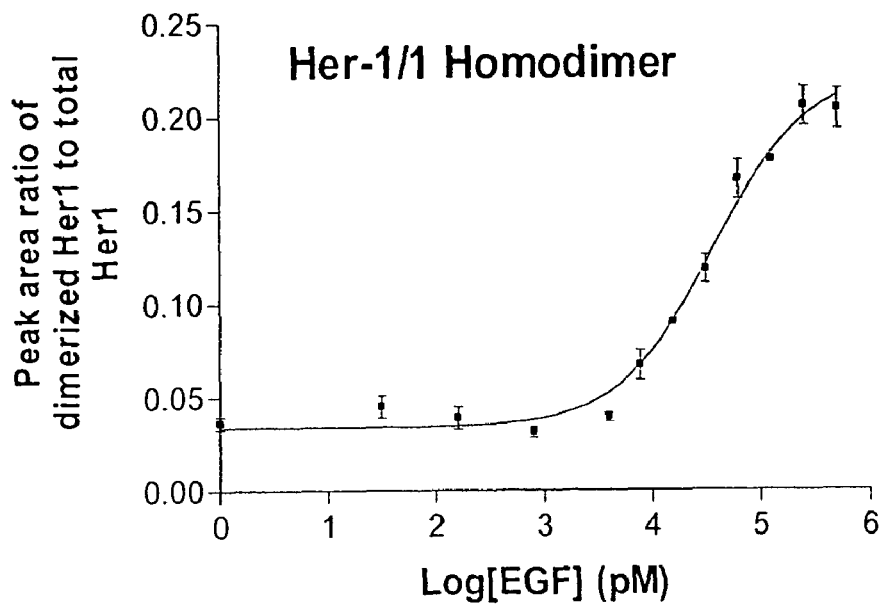
FIGS. 11A and 11B illustrate data from assays of the invention for detecting homodimers and phosphorylation of Her1.
Figure 11B:
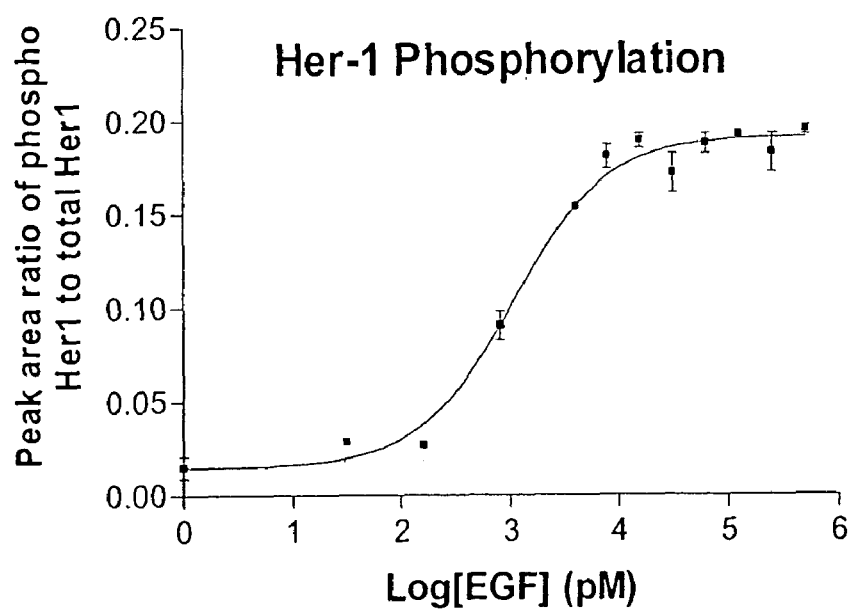
Figure 12:
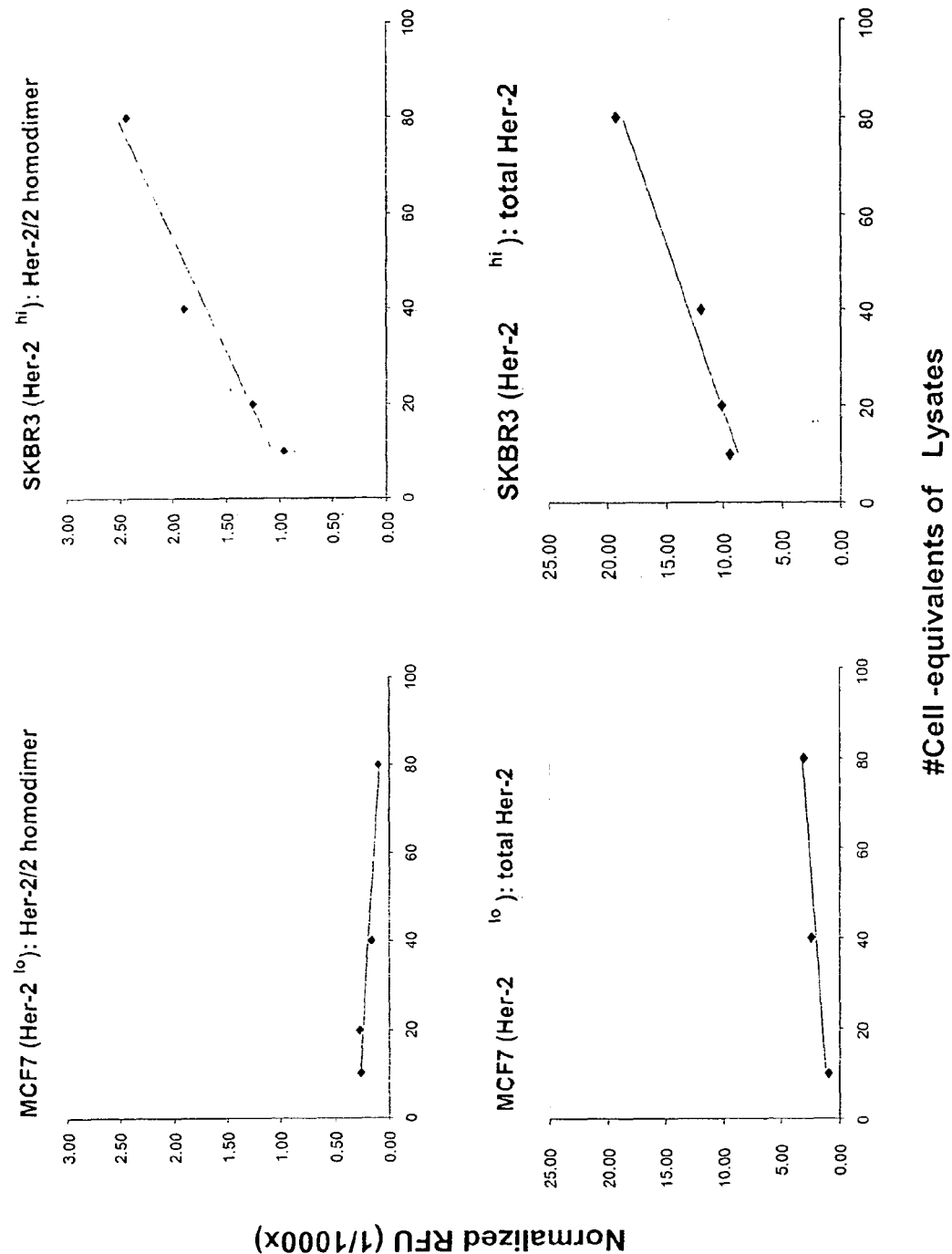
FIG. 12 shows data from assays of the invention that show Her2 dimer populations on two different cell lines.

Results of the assays are illustrated in FIGS. 11A–11B and FIG. 12. FIG. 11A shows that the quantity of Her1—Her1 homodimers on BT-20 cells increases with increasing concentration of EGF. FIG. 11B shows that the quantity of Her1 phosphorylation in BT-20 cells increases with increasing EGF concentration. The detection of Her2—Her2 homodimers was demonstrated by comparison of signals from SKBR-3 cells expressing Her2 with signals from MCF-7 cells that express reduced level of Her2 on the cell surface. As shown in the charts of FIG. 12, no specific titratable Her2—Her2 homodimer signals were detected with MCF-7 cells whereas Her2—Her2 homodimer signals from SKBR-3 cells were clearly above the signals from MCF-7 cells

EXAMPLE 5

Analysis of Cell Lysates for Her1—Her3 Heterodimerization and Receptor Phosphorylation Samples are prepared as follows:
1. Serum-starve breast cancer cell line culture overnight before use.
2. Stimulate cell lines with HRG in culture media for 10 minutes at 37° C. Exemplary doses of HRG are 0, 0.032, 0.16, 0.8, 4, 20, 100 nM for T47D.
3. Aspirate culture media, transfer onto ice, and add lysis buffer to lyse cells in situ.
4. Scrape and transfer lysate to microfuge tube. Incubate on ice for 30 min. Microfuge at 14,000 rpm, 4° C., for 10 min. (Centrifugation is optional.)
5. Collect supernatants as lysates and aliquot for storage at −80° C. until use.

Assay design: The total assay volume is 40 ul. The lysate volume is adjusted to 30 ul with lysis buffer. The antibodies are diluted in lysis buffer up to 5 ul. Typically ~5000 to 50000 cell-equivalent of lysates is used per reaction. Final concentrations of pre-mixed antibodies in reaction:
Pro10_Ab11 anti-Her-1: 0.05–0.1 ug/ml
Pro11_anti-Her-3: 0.1 ug/ml
Pro2_PT100 anti-phospho-Tyr: 0.1 ug/ml
Biotin_anti-Her-3: 1–2 ug/ml
1. To assay 96-well, add 5 ul antibody mix to 30 ul lysate and incubate for 1 hour at RT.
2. Add 5 ul streptavidin-derivatized molecular scissor (final 4 ug/well) to assay well and incubate for 45 min.
3. Add 150 ul of PBS with 1% BSA to 96-well filter plate (Millipore MAGVN2250) and incubate for 1 hr at RT for blocking.
4. Empty filter plate by vacuum suction. Transfer assay reactions to filter plate and apply vacuum to empty.
5. Add 200 ul wash buffer and apply vacuum to empty. Repeat one time.
6. Add 200 ul illumination buffer and apply vacuum to empty. Repeat one time.
7. Add 30 ul illumination buffer and illuminate for 20 min.
8. Transfer 10 ul of each reaction to CE assay plate for analysis using ABI3100 capillary electrophoresis instrument with a 22 cm capillary (injection conditions: 5 kV, 425 sec, 30OC; run conditions: 600 sec, 30° C.).

Data Analysis:
1. Normalize RFU signal of each eTag reporter against CE reference standard A315.
2. Subtract RFU of "no lysate" background control from corresponding eTag reporter signals.
3. Report heterodimerization as the Her-1 derived Pro10 RFU ratiometric to Pro11 RFU from anti-Her-3.
4. Report receptor phosphorylation for Her-1/3 as RFU from Pro2_PT1OO anti-phospho-Tyr ratiometric to RFU from Pro11_anti-Her-3 from assay wells using biotin-anti-Her-3.

Results of the assay are illustrated in FIGS. 13A and 13B. The data show that both Her1—Her3 heterodimerization and dimer phosphorylation increase with increasing concentrations of HRG.

What is claimed is:

1. A method for detecting a dimer in a sample, the method comprising: mixing (i) a sample, which contains a dimer comprising a first membrane-associated analyte and a second membrane-associated analyte; (ii) a cleaving probe, which is capable of binding the first membrane-associated analyte and has a cleavage-inducing moiety with an effective proximity; and (iii) one or more binding compounds, at least one of which is capable of binding the second membrane-associated analyte, and each binding compound has one or more molecular tags attached thereto by a cleavable linkage, wherein cleavage of the cleavable linkage(s) within the effective proximity of the cleavage-inducing moiety of the cleaving probe releases the molecular tag(s);
wherein detecting the released molecular tag(s) detects the dimer.

2. The method of claim 1, wherein the first membrane-associated analyte and the second membrane associated analyte are both cell surface receptors.

3. The method of claim 2, wherein the first membrane-associated analyte and the second membrane associated analyte are the same receptor type.

4. The method of claim 2, wherein the first membrane-associated analyte and the second membrane associated analyte are different receptor types.

5. The method of claim 2, wherein the cell surface receptors are selected from the group consisting of epidermal growth factor receptors and G-protein coupled receptors.

6. The method of claim 5, wherein the cell surface receptors are selected from the group consisting of Her1, Her2, Her3 and Her4.

7. The method of claim 6, wherein the dimer is selected from the group consisting of a Her1—Her1 homodimer, a Her1–Her2 heterodimer, a Her1–Her3 heterodimer and a Her2–Her3 heterodimer.

8. The method of claim 1, wherein the cleaving probe comprises an antibody binding composition.

9. The method of claim 8, wherein the antibody binding composition comprises a monoclonal antibody.

10. The method of claim 8, wherein the antibody binding composition binds an antigenic determinant of the first membrane-associated analyte.

11. The method of claim 1, wherein the cleavage-inducing moiety of the cleaving probe is a sensitizer.

12. The method of claim 11, further comprising inducing the sensitizer to generate an active species that cleaves the cleavable linkage(s) of the binding compound(s) within the effective proximity.

13. The method of claim 11, wherein the sensitizer is a photosensitizer.

14. The method of claim 13, further comprising illuminating the photosensitizer to generate an active species that cleaves the cleavable linkage(s) of the binding compound(s) within the effective proximity.

15. The method of claim 12 or 14, wherein the active species is singlet oxygen.

16. The method of claim 15, wherein the cleavable linkage of the binding compound is an oxidation-labile linkage.

17. The method of claim 16, wherein the cleavable linkage of the binding compound is selected from the group consisting of a thioether, an olefin, a thiazole, and an oxazole.

18. The method of claim 1, wherein the one or more molecular tags have a separation characteristic.

19. The method of claim 18, further comprising separating the released molecular tags.

20. The method of claim 19, wherein the separation characteristic of said one or more molecular tags is electrophoretic mobility and the step of separating comprises electrophoretically separating the released molecular tags in a separation buffer.

21. The method of claim 1, wherein the one or more molecular tags are capable of generating an electrochemical, fluorescent or chromogenic signal.

22. The method of claim 21, wherein the one or more molecular tags are capable of generating a fluorescent signal.

23. The method of claim 1, wherein the one or more binding compounds comprise an antibody binding composition.

24. The method of claim 23, wherein the antibody binding composition comprises a monoclonal antibody.

25. The method of claim 1, wherein at least two binding compounds are mixed.

26. The method of claim 25, wherein the at least two binding compounds comprise at least two different binding compounds which bind different antigenic determinants of the first or second membrane-associated analyte.

27. The method of claim 25, wherein at least one of the binding compounds binds a phosphorylation site of the first or second membrane-associated analyte.

28. The method of claim 25, wherein at least two of the molecular tags attached to the at least two binding compounds have different separation characteristics.

29. The method of claim 28, wherein the method further comprises separating the released molecular tags from the at least two binding compounds.

30. The method of claim 29, wherein the molecular tags from the at least two binding compounds have different electrophoretic mobility and are separated electrophoretically.

31. The method of claim 30, further comprising incubating the cleaving probe, the at least two binding compounds and the sample in a binding buffer, and exchanging the binding buffer with a separation buffer, wherein said steps of incubating and exchanging are performed prior to said step of separating.

* * * * *